(12) United States Patent
Kayyem et al.

(10) Patent No.: US 9,957,553 B2
(45) Date of Patent: May 1, 2018

(54) INTEGRATED MULTIPLEX TARGET ANALYSIS

(71) Applicant: GENMARK DIAGNOSTICS, INC., Carlsbad, CA (US)

(72) Inventors: Jon Faiz Kayyem, Boulder, CO (US); Jayashankar Srinivasan, Vernon Hills, IL (US); Sean Ford, Oceanside, CA (US)

(73) Assignee: GENMARK DIAGNOSTICS, INC., Carlsbad, CA (US)

( * ) Notice: Subject to any disclaimer, the term of this patent is extended or adjusted under 35 U.S.C. 154(b) by 0 days. days.

(21) Appl. No.: 14/062,865

(22) Filed: Oct. 24, 2013

(65) Prior Publication Data
US 2014/0194305 A1 Jul. 10, 2014

Related U.S. Application Data

(60) Provisional application No. 61/717,887, filed on Oct. 24, 2012, provisional application No. 61/798,091, filed on Mar. 15, 2013.

(51) Int. Cl.
*C12Q 1/68* (2018.01)
*B01L 3/00* (2006.01)
*B01L 7/00* (2006.01)
*B01L 9/00* (2006.01)

(52) U.S. Cl.
CPC ...... *C12Q 1/6825* (2013.01); *B01L 3/502715* (2013.01); *B01L 3/502738* (2013.01); *B01L 3/502784* (2013.01); *B01L 3/523* (2013.01); *B01L 7/52* (2013.01); *B01L 9/527* (2013.01); *B01L 2200/025* (2013.01); *B01L 2200/10* (2013.01); *B01L 2200/16* (2013.01); *B01L 2300/021* (2013.01); *B01L 2300/0672* (2013.01); *B01L 2300/0816* (2013.01); *B01L 2300/0867* (2013.01); *B01L 2300/1822* (2013.01); *B01L 2300/1827* (2013.01);
(Continued)

(58) Field of Classification Search
None
See application file for complete search history.

(56) References Cited

U.S. PATENT DOCUMENTS 3,641,909 A 2/1972 Baker
3,687,051 A 8/1972 Baker et al.
3,776,425 A 12/1973 Baker et al.
(Continued)

FOREIGN PATENT DOCUMENTS

CN 101715428 A 5/2010
EP 0173547 A2 3/1986
(Continued)

OTHER PUBLICATIONS

The definition of "oleophobic" provided by the online dictionary at merriam-webster.com [retrieved on Dec. 7, 2017]. Retrieved from the Internet: <URL: www.merriamwebster.com/medical/oleophobic>. (Year: 2017).*
(Continued)

*Primary Examiner* — Robert T. Crow
(74) *Attorney, Agent, or Firm* — Rothwell, Figg, Ernst & Manbeck, P.C.

(57) ABSTRACT

This invention provides biochip cartridges and instrument devices for the detection and/or analysis of target analytes from patient samples.

20 Claims, 42 Drawing Sheets

(52) U.S. Cl.
CPC ............... *B01L 2400/0427* (2013.01); *B01L 2400/0481* (2013.01); *B01L 2400/0683* (2013.01)

(56) References Cited

U.S. PATENT DOCUMENTS

| | | |
|---|---|---|
| 3,820,149 A | 6/1974 | Baker et al. |
| 4,007,010 A | 2/1977 | Woodbridge, III |
| 4,182,447 A | 1/1980 | Kay |
| 4,469,863 A | 9/1984 | Ts'o et al. |
| 4,769,333 A | 9/1988 | Dole et al. |
| 4,859,603 A | 8/1989 | Dole et al. |
| 4,887,455 A | 12/1989 | Payne et al. |
| 4,978,502 A | 12/1990 | Dole et al. |
| 5,034,506 A | 7/1991 | Summerton et al. |
| 5,089,233 A | 2/1992 | Devaney, Jr. et al. |
| 5,098,660 A | 3/1992 | Devaney, Jr. |
| 5,154,888 A | 10/1992 | Zander et al. |
| 5,216,141 A | 6/1993 | Benner |
| 5,229,297 A | 7/1993 | Schnipelsky et al. |
| 5,234,809 A | 8/1993 | Boom et al. |
| 5,235,033 A | 8/1993 | Summerton et al. |
| 5,254,479 A | 10/1993 | Chemelli |
| 5,288,463 A | 2/1994 | Chemelli |
| 5,290,518 A | 3/1994 | Johnson |
| 5,374,395 A | 12/1994 | Robinson et al. |
| 5,386,023 A | 1/1995 | Sanghvi et al. |
| 5,422,271 A | 6/1995 | Chen et al. |
| 5,460,780 A | 10/1995 | Devaney, Jr. et al. |
| 5,468,366 A | 11/1995 | Wegner et al. |
| 5,512,439 A | 4/1996 | Hornes et al. |
| 5,529,188 A | 6/1996 | Coggswell |
| 5,591,578 A | 1/1997 | Meade et al. |
| 5,593,804 A | 1/1997 | Chemelli et al. |
| 5,602,240 A | 2/1997 | De Mesmaeker et al. |
| 5,637,684 A | 6/1997 | Cook et al. |
| 5,644,048 A | 7/1997 | Yau |
| 5,652,149 A | 7/1997 | Mileaf et al. |
| 5,674,653 A | 10/1997 | Chemelli et al. |
| 5,681,702 A | 10/1997 | Collins et al. |
| 5,692,644 A | 12/1997 | Gueret |
| 5,705,348 A | 1/1998 | Meade et al. |
| 5,705,628 A | 1/1998 | Hawkins |
| 5,714,380 A | 2/1998 | Neri et al. |
| 5,716,852 A | 2/1998 | Yager et al. |
| 5,726,404 A | 3/1998 | Brody |
| 5,726,751 A | 3/1998 | Altendorf et al. |
| 5,747,349 A | 5/1998 | Van Den Engh et al. |
| 5,748,827 A | 5/1998 | Holl et al. |
| 5,770,365 A | 6/1998 | Lane et al. |
| 5,807,701 A | 9/1998 | Payne et al. |
| 5,824,473 A | 10/1998 | Meade et al. |
| 5,849,486 A * | 12/1998 | Heller ............... B01J 19/0046 257/E21.43 |
| 5,851,536 A | 12/1998 | Yager et al. |
| 5,873,990 A | 2/1999 | Wojciechowski et al. |
| 5,876,187 A | 3/1999 | Afromowitz et al. |
| 5,882,497 A | 3/1999 | Persaud et al. |
| 5,898,071 A | 4/1999 | Hawkins |
| 5,932,100 A | 8/1999 | Yager et al. |
| 5,948,684 A | 9/1999 | Weigl et al. |
| 5,955,028 A | 9/1999 | Chow |
| 5,971,158 A | 10/1999 | Yager et al. |
| 5,972,710 A | 10/1999 | Weigl et al. |
| 5,973,138 A | 10/1999 | Collis |
| 5,974,867 A | 11/1999 | Forster et al. |
| 6,007,775 A | 12/1999 | Yager |
| 6,013,170 A | 1/2000 | Meade |
| 6,013,459 A | 1/2000 | Meade |
| 6,033,601 A | 3/2000 | Persaud et al. |
| 6,039,897 A | 3/2000 | Lochhead et al. |
| 6,063,573 A | 5/2000 | Kayyem |
| 6,067,157 A | 5/2000 | Altendorf |
| 6,071,478 A | 6/2000 | Chow |
| 6,090,933 A | 7/2000 | Kayyem et al. |
| 6,091,502 A | 7/2000 | Weigl et al. |
| 6,096,273 A | 8/2000 | Kayyem et al. |
| 6,110,354 A | 8/2000 | Saban et al. |
| 6,134,950 A | 10/2000 | Forster et al. |
| 6,136,272 A | 10/2000 | Weigl et al. |
| 6,159,739 A | 12/2000 | Weigl et al. |
| 6,167,910 B1 | 1/2001 | Chow |
| 6,171,865 B1 | 1/2001 | Weigl et al. |
| 6,180,064 B1 | 1/2001 | Persaud et al. |
| 6,180,114 B1 | 1/2001 | Yager et al. |
| 6,190,858 B1 | 2/2001 | Persaud et al. |
| 6,192,351 B1 | 2/2001 | Persaud |
| 6,235,501 B1 | 2/2001 | Gautsch et al. |
| 6,221,583 B1 | 4/2001 | Kayyem et al. |
| 6,221,677 B1 | 4/2001 | Wu et al. |
| 6,227,809 B1 | 5/2001 | Forster et al. |
| 6,232,062 B1 | 5/2001 | Kayyem et al. |
| 6,236,951 B1 | 5/2001 | Payne et al. |
| 6,248,229 B1 | 6/2001 | Meade |
| 6,255,477 B1 | 7/2001 | Kleiber et al. |
| 6,264,825 B1 | 7/2001 | Blackburn et al. |
| 6,265,155 B1 | 7/2001 | Meade et al. |
| 6,268,136 B1 | 7/2001 | Shuber et al. |
| 6,277,641 B1 | 8/2001 | Yager |
| 6,290,839 B1 | 9/2001 | Kayyem et al. |
| 6,297,061 B1 | 10/2001 | Wu et al. |
| 6,300,138 B1 | 10/2001 | Gleason et al. |
| 6,321,791 B1 | 11/2001 | Chow |
| 6,361,958 B1 | 3/2002 | Shieh et al. |
| 6,366,924 B1 | 4/2002 | Parce |
| 6,376,232 B1 | 4/2002 | Payne et al. |
| 6,387,290 B1 | 5/2002 | Brody et al. |
| 6,391,558 B1 | 5/2002 | Henkens et al. |
| 6,399,023 B1 | 6/2002 | Chow |
| 6,399,025 B1 | 6/2002 | Chow |
| 6,403,338 B1 | 6/2002 | Knapp et al. |
| 6,404,493 B1 | 6/2002 | Altendorf |
| 6,406,857 B1 | 6/2002 | Shuber et al. |
| 6,408,884 B1 | 6/2002 | Kamholz et al. |
| 6,409,832 B2 | 6/2002 | Wiegl et al. |
| 6,415,821 B2 | 7/2002 | Kamholz et al. |
| 6,426,230 B1 | 7/2002 | Feistel |
| 6,431,016 B1 | 8/2002 | Payne |
| 6,431,212 B1 | 8/2002 | Hayenga et al. |
| 6,431,476 B1 | 8/2002 | Taylor et al. |
| 6,432,720 B2 | 8/2002 | Chow |
| 6,432,723 B1 | 8/2002 | Plaxco et al. |
| 6,433,160 B1 | 8/2002 | Collis |
| 6,440,725 B1 | 8/2002 | Pourahmadi et al. |
| 6,443,307 B1 | 9/2002 | Burridge |
| 6,451,606 B1 | 9/2002 | Konig et al. |
| 6,454,945 B1 | 9/2002 | Weigl et al. |
| 6,479,240 B1 | 11/2002 | Kayyem et al. |
| 6,482,306 B1 | 11/2002 | Yager et al. |
| 6,488,896 B2 | 12/2002 | Weigl et al. |
| 6,494,230 B2 | 12/2002 | Chow |
| 6,495,104 B1 | 12/2002 | Unno et al. |
| 6,495,323 B1 | 12/2002 | Kayyem et al. |
| 6,503,757 B1 | 1/2003 | Chow |
| 6,518,024 B2 | 2/2003 | Choong et al. |
| 6,524,456 B1 | 2/2003 | Ramsey et al. |
| 6,537,501 B1 | 3/2003 | Holl et al. |
| 6,541,213 B1 | 4/2003 | Weigl et al. |
| 6,541,617 B1 | 4/2003 | Bamdad et al. |
| 6,557,427 B2 | 5/2003 | Weigl et al. |
| 6,562,568 B1 | 5/2003 | Kleiber et al. |
| 6,565,727 B1 | 5/2003 | Shenderov |
| 6,575,188 B2 | 6/2003 | Parunak |
| 6,576,194 B1 | 6/2003 | Holl et al. |
| 6,581,899 B2 | 6/2003 | Williams |
| 6,582,963 B1 | 6/2003 | Weigl et al. |
| 6,596,483 B1 | 7/2003 | Choong et al. |
| 6,600,026 B1 | 7/2003 | Yu |
| 6,602,400 B1 | 8/2003 | Choong et al. |
| 6,627,412 B1 | 9/2003 | Manning et al. |
| 6,642,046 B1 | 11/2003 | McGarry et al. |
| 6,645,758 B1 | 11/2003 | Schnipelsky et al. |
| 6,647,397 B2 | 11/2003 | Parce |
| 6,648,015 B1 | 11/2003 | Chow |

(56) References Cited

U.S. PATENT DOCUMENTS

| | | |
|---|---|---|
| 6,655,010 B1 | 12/2003 | Hatfield et al. |
| 6,656,431 B2 | 12/2003 | Holl et al. |
| 6,660,480 B2 | 12/2003 | Ramsey et al. |
| 6,664,104 B2 | 12/2003 | Pourahmadi et al. |
| 6,674,525 B2 | 1/2004 | Bardell et al. |
| 6,686,150 B1 | 2/2004 | Blackburn et al. |
| 6,695,147 B1 | 2/2004 | Yager et al. |
| 6,706,498 B2 | 3/2004 | Gautsch et al. |
| 6,712,925 B1 | 3/2004 | Holl et al. |
| 6,739,531 B2 | 5/2004 | Taylor |
| 6,740,518 B1 | 5/2004 | Duong et al. |
| 6,742,661 B1 | 6/2004 | Schulte et al. |
| 6,743,399 B1 | 6/2004 | Weigl et al. |
| 6,753,143 B2 | 6/2004 | Tao et al. |
| 6,761,816 B1 | 7/2004 | Blackburn et al. |
| 6,773,566 B2 | 8/2004 | Shenderov |
| 6,783,647 B2 | 8/2004 | Culbertson et al. |
| 6,790,341 B1 | 9/2004 | Saban et al. |
| 6,824,669 B1 | 11/2004 | Li et al. |
| 6,830,729 B1 | 12/2004 | Holl et al. |
| 6,833,267 B1 | 12/2004 | Kayyem |
| 6,852,284 B1 | 2/2005 | Holl et al. |
| 6,857,449 B1 | 2/2005 | Chow |
| 6,875,619 B2 | 4/2005 | Blackburn |
| 6,878,540 B2 | 4/2005 | Pourahmadi et al. |
| 6,881,541 B2 | 4/2005 | Petersen et al. |
| 6,887,693 B2 | 5/2005 | McMillan et al. |
| 6,893,879 B2 | 5/2005 | Petersen et al. |
| 6,914,137 B2 | 7/2005 | Baker |
| 6,919,444 B2 | 7/2005 | Harttig et al. |
| 6,942,771 B1 | 9/2005 | Kayyem |
| 6,951,759 B2 | 10/2005 | Travers et al. |
| 6,960,437 B2 | 11/2005 | Enzelberger et al. |
| 6,960,467 B2 | 11/2005 | Shieh et al. |
| 6,968,978 B1 | 11/2005 | Matthews |
| 6,977,151 B2 | 12/2005 | Kayyem et al. |
| 6,979,424 B2 | 12/2005 | Northrup et al. |
| 7,010,391 B2 | 3/2006 | Handique et al. |
| 7,011,791 B2 | 3/2006 | Weigl et al. |
| 7,014,992 B1 | 3/2006 | Kayyem et al. |
| 7,018,523 B2 | 3/2006 | Meade |
| 7,030,989 B2 | 4/2006 | Yager et al. |
| 7,045,285 B1 | 5/2006 | Kayyem et al. |
| 7,056,475 B2 | 6/2006 | Lum et al. |
| 7,056,669 B2 | 6/2006 | Kayyem et al. |
| 7,087,148 B1 | 8/2006 | Blackburn et al. |
| 7,090,804 B2 | 8/2006 | Kayyem et al. |
| 7,119,194 B2 | 10/2006 | Uematsu et al. |
| 7,125,668 B2 | 10/2006 | Kayyem et al. |
| 7,141,429 B2 | 11/2006 | Munson et al. |
| 7,155,344 B1 | 12/2006 | Parce et al. |
| 7,160,678 B1 | 1/2007 | Kayyem et al. |
| 7,163,612 B2 | 1/2007 | Sterling et al. |
| 7,169,358 B2 | 1/2007 | Henkens et al. |
| 7,172,897 B2 | 2/2007 | Blackburn et al. |
| 7,192,557 B2 | 3/2007 | Wu et al. |
| 7,201,881 B2 | 4/2007 | Cox et al. |
| 7,208,271 B2 | 4/2007 | Bost et al. |
| 7,223,371 B2 | 5/2007 | Hayenga et al. |
| 7,226,562 B2 | 6/2007 | Holl et al. |
| 7,238,268 B2 | 7/2007 | Ramsey et al. |
| 7,255,780 B2 | 8/2007 | Shenderov |
| 7,258,837 B2 | 8/2007 | Yager et al. |
| 7,267,939 B2 | 9/2007 | Meade |
| 7,270,786 B2 | 9/2007 | Parunak et al. |
| 7,271,007 B2 | 9/2007 | Weigl et al. |
| 7,312,087 B2 | 12/2007 | Duong et al. |
| 7,323,140 B2 | 1/2008 | Handique et al. |
| 7,343,248 B2 | 3/2008 | Parce et al. |
| 7,364,886 B2 | 4/2008 | Hasenbank et al. |
| 7,371,830 B2 | 5/2008 | Kleiber et al. |
| 7,381,525 B1 | 6/2008 | Kayyem et al. |
| 7,381,533 B2 | 6/2008 | Kayyem et al. |
| 7,384,749 B2 | 6/2008 | Kayyem et al. |
| 7,393,645 B2 | 7/2008 | Kayyem et al. |
| 7,405,054 B1 | 7/2008 | Hasenbank et al. |
| 7,416,791 B1 | 8/2008 | Carlson et al. |
| 7,416,892 B2 | 8/2008 | Battrell et al. |
| 7,419,575 B2 | 9/2008 | Culbertson et al. |
| 7,419,638 B2 | 9/2008 | Saltsman et al. |
| 7,439,014 B2 | 10/2008 | Pamula et al. |
| 7,473,397 B2 | 1/2009 | Griffin et al. |
| 7,491,495 B2 | 2/2009 | Zielenski et al. |
| 7,514,228 B2 | 4/2009 | Meade |
| 7,534,331 B2 | 5/2009 | Kayyem |
| 7,544,506 B2 | 6/2009 | Breidford et al. |
| 7,550,267 B2 | 6/2009 | Hawkins et al. |
| 7,560,237 B2 | 7/2009 | O'Connor et al. |
| 7,566,534 B2 | 7/2009 | Meade |
| 7,569,346 B2 | 8/2009 | Petersen et al. |
| 7,579,145 B2 | 8/2009 | Meade |
| D599,832 S | 9/2009 | Chapin et al. |
| 7,582,419 B2 | 9/2009 | Meade |
| 7,595,153 B2 | 9/2009 | Meade |
| 7,601,507 B2 | 10/2009 | O'Connor et al. |
| 7,648,835 B2 | 1/2010 | Breidford et al. |
| 7,655,129 B2 | 2/2010 | Blackburn et al. |
| 7,655,190 B2 | 2/2010 | Satou et al. |
| 7,659,089 B2 | 2/2010 | Hasenbank et al. |
| 7,669,597 B2 | 3/2010 | Sullivan et al. |
| 7,713,711 B2 | 5/2010 | O'Connor et al. |
| 7,727,723 B2 | 6/2010 | Pollack et al. |
| 7,731,906 B2 | 6/2010 | Handique et al. |
| 7,736,891 B2 | 6/2010 | Nelson et al. |
| 7,759,073 B2 | 6/2010 | O'Connor et al. |
| 7,763,453 B2 | 7/2010 | Clemmens et al. |
| 7,763,471 B2 | 7/2010 | Pamula et al. |
| 7,789,270 B2 | 9/2010 | Tanaami et al. |
| 7,794,669 B2 | 9/2010 | Gyonouchi et al. |
| 7,815,871 B2 | 10/2010 | Pamula et al. |
| 7,816,121 B2 | 10/2010 | Pollack et al. |
| 7,820,030 B2 | 10/2010 | Althaus et al. |
| 7,820,391 B2 | 10/2010 | Chunlin |
| 7,822,510 B2 | 10/2010 | Paik et al. |
| 7,833,708 B2 | 11/2010 | Enzelberger et al. |
| 7,851,184 B2 | 12/2010 | Pollack et al. |
| 7,854,897 B2 | 12/2010 | Tanaami et al. |
| 7,858,045 B2 | 12/2010 | Tanaami et al. |
| 7,863,035 B2 | 1/2011 | Clemens et al. |
| 7,867,757 B2 | 1/2011 | Karlsen et al. |
| 7,901,947 B2 | 3/2011 | Pollack et al. |
| 7,910,294 B2 | 3/2011 | Karlsen |
| 7,914,994 B2 | 3/2011 | Petersen et al. |
| 7,919,330 B2 | 4/2011 | De Guzman et al. |
| 7,935,316 B2 | 5/2011 | Gyonouchi et al. |
| 7,935,481 B1 | 5/2011 | Umek et al. |
| 7,935,537 B2 | 5/2011 | Haley |
| 7,939,021 B2 | 5/2011 | Smith et al. |
| 7,943,030 B2 | 5/2011 | Shenderov |
| 7,955,836 B2 | 6/2011 | Clemmens et al. |
| 7,987,022 B2 | 7/2011 | Handique et al. |
| 7,998,436 B2 | 8/2011 | Pollack et al. |
| 7,998,708 B2 | 8/2011 | Handique et al. |
| 8,007,739 B2 | 8/2011 | Pollack et al. |
| 8,012,743 B2 | 9/2011 | Bamdad et al. |
| 8,017,340 B2 | 9/2011 | Collier et al. |
| 8,041,463 B2 | 10/2011 | Pollack et al. |
| 8,048,628 B2 | 11/2011 | Pollack et al. |
| 8,053,239 B2 | 11/2011 | Wheeler et al. |
| 8,088,578 B2 | 1/2012 | Hua et al. |
| 8,093,062 B2 | 1/2012 | Winger |
| 8,101,403 B2 | 1/2012 | Yager et al. |
| 8,101,431 B2 | 1/2012 | McDevitt et al. |
| 8,105,477 B2 | 1/2012 | Althaus et al. |
| 8,105,783 B2 | 1/2012 | Handique |
| 8,105,849 B2 | 1/2012 | McDevitt et al. |
| 8,110,392 B2 | 2/2012 | Battrell et al. |
| 8,114,661 B2 | 2/2012 | O'Connor et al. |
| 8,129,118 B2 | 3/2012 | Weindel et al. |
| 8,133,671 B2 | 3/2012 | Williams et al. |
| 8,133,703 B2 | 3/2012 | Ching et al. |
| 8,137,917 B2 | 3/2012 | Pollack et al. |
| 8,168,442 B2 | 5/2012 | Petersen et al. |
| 8,187,864 B2 | 5/2012 | Wheeler et al. |

(56) References Cited

U.S. PATENT DOCUMENTS

| | | |
|---|---|---|
| 8,201,765 B2 | 6/2012 | Ratagopal et al. |
| 8,202,686 B2 | 6/2012 | Pamula et al. |
| 8,202,736 B2 | 6/2012 | Mousa et al. |
| 8,208,146 B2 | 6/2012 | Srinivasan et al. |
| 8,216,529 B2 | 7/2012 | Ade et al. |
| 8,216,832 B2 | 7/2012 | Battrell et al. |
| 8,222,023 B2 | 7/2012 | Battrell et al. |
| 8,247,176 B2 | 8/2012 | Petersen et al. |
| 8,247,191 B2 | 8/2012 | Ritzen et al. |
| 8,268,246 B2 | 9/2012 | Srinivasan et al. |
| 8,273,308 B2 | 9/2012 | Handique et al. |
| 8,304,253 B2 | 11/2012 | Yi et al. |
| 8,313,698 B2 | 11/2012 | Pollack et al. |
| 8,313,895 B2 | 11/2012 | Pollack et al. |
| 8,317,990 B2 | 11/2012 | Pamula et al. |
| 8,318,109 B2 | 11/2012 | Saltsman et al. |
| 8,318,439 B2 | 11/2012 | Battrell et al. |
| 8,323,900 B2 | 12/2012 | Handique et al. |
| 8,329,453 B2 | 12/2012 | Battrell et al. |
| 8,338,166 B2 | 12/2012 | Beer et al. |
| 8,343,636 B2 | 1/2013 | Jen et al. |
| 8,349,276 B2 | 1/2013 | Pamula et al. |
| 8,356,763 B2 | 1/2013 | Rajagopal et al. |
| 8,364,315 B2 | 1/2013 | Sturmer et al. |
| 8,367,370 B2 | 2/2013 | Wheeler et al. |
| 8,372,340 B2 | 2/2013 | Bird et al. |
| 8,388,909 B2 | 3/2013 | Pollack et al. |
| 8,389,297 B2 | 3/2013 | Pamula et al. |
| 8,394,608 B2 | 3/2013 | Ririe et al. |
| 8,394,641 B2 | 3/2013 | Winger |
| 8,404,440 B2 | 3/2013 | Solli et al. |
| 8,426,213 B2 | 4/2013 | Eckhardt et al. |
| 8,426,214 B2 | 4/2013 | Stayton et al. |
| 8,431,389 B2 | 4/2013 | Battrell et al. |
| 8,440,392 B2 | 5/2013 | Pamula et al. |
| 8,454,905 B2 | 6/2013 | Pope et al. |
| 8,460,528 B2 | 6/2013 | Pollack et al. |
| 8,470,606 B2 | 6/2013 | Srinivasan et al. |
| 8,481,125 B2 | 7/2013 | Yi et al. |
| 8,492,168 B2 | 7/2013 | Srinivasan et al. |
| 8,506,908 B2 | 8/2013 | Benn et al. |
| 8,518,662 B2 | 8/2013 | Ritzen et al. |
| 8,541,176 B2 | 9/2013 | Pamula et al. |
| 8,551,424 B2 | 10/2013 | Abraham-Fuchs et al. |
| 8,557,198 B2 | 10/2013 | Saltsman et al. |
| 8,562,807 B2 | 10/2013 | Srinivasan et al. |
| 8,580,209 B2 | 11/2013 | Kurowski et al. |
| 8,591,830 B2 | 11/2013 | Sudarsan et al. |
| 8,592,217 B2 | 11/2013 | Eckhardt |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,658,111 B2 | 2/2014 | Srinivasan et al. |
| 8,685,344 B2 | 4/2014 | Sudarsan et al. |
| 8,685,754 B2 | 4/2014 | Pollack et al. |
| 8,951,781 B2 | 2/2015 | Reed et al. |
| 9,211,538 B2 | 12/2015 | Weber |
| 2002/0006643 A1 | 1/2002 | Kayyem et al. |
| 2002/0068357 A1* | 6/2002 | Mathies ............... B01J 19/0093 435/287.2 |
| 2003/0025129 A1 | 2/2003 | Hahn et al. |
| 2003/0034271 A1 | 2/2003 | Burridge |
| 2003/0038040 A1 | 2/2003 | Bertl et al. |
| 2003/0048631 A1 | 3/2003 | Ladyjensky |
| 2003/0197139 A1 | 10/2003 | Williams |
| 2004/0037739 A1* | 2/2004 | McNeely et al. ............... 422/58 |
| 2004/0053290 A1 | 3/2004 | Terbrueggen et al. |
| 2004/0137607 A1 | 7/2004 | Tanaami et al. |
| 2004/0185551 A1* | 9/2004 | Niehaus ..................... 435/287.2 |
| 2004/0229378 A1 | 11/2004 | Schulte et al. |
| 2004/0254559 A1 | 12/2004 | Tanaami et al. |
| 2005/0003399 A1* | 1/2005 | Blackburn et al. ............... 435/6 |
| 2005/0064423 A1 | 3/2005 | Higuchi et al. |
| 2005/0164373 A1 | 7/2005 | Oldham et al. |
| 2005/0201903 A1 | 9/2005 | Weigl et al. |
| 2005/0205816 A1 | 9/2005 | Hayenga et al. |
| 2005/0233440 A1 | 10/2005 | Scurati et al. |
| 2005/0244308 A1 | 11/2005 | Tanaami et al. |
| 2006/0057581 A1 | 3/2006 | Karlsen et al. |
| 2006/0079834 A1 | 4/2006 | Tennican et al. |
| 2006/0166233 A1 | 7/2006 | Wu et al. |
| 2006/0183216 A1 | 8/2006 | Handique et al. |
| 2006/0246575 A1 | 11/2006 | Lancaster et al. |
| 2006/0264782 A1 | 11/2006 | Holmes et al. |
| 2006/0275813 A1 | 12/2006 | Tanaami et al. |
| 2006/0275852 A1 | 12/2006 | Montagu et al. |
| 2007/0013733 A1 | 1/2007 | Katsurai et al. |
| 2007/0017927 A1 | 1/2007 | D'Amore et al. |
| 2007/0042427 A1 | 2/2007 | Gerdes et al. |
| 2007/0098600 A1 | 5/2007 | Kayyem |
| 2007/0178529 A1 | 8/2007 | Breidford et al. |
| 2007/0184547 A1 | 8/2007 | Handique et al. |
| 2007/0219480 A1 | 9/2007 | Kamen et al. |
| 2007/0241068 A1 | 10/2007 | Pamula et al. |
| 2007/0242105 A1 | 10/2007 | Srinivasan et al. |
| 2007/0275415 A1 | 11/2007 | Srinivasan et al. |
| 2007/0292941 A1* | 12/2007 | Handique ............... B01L 3/5027 435/288.7 |
| 2008/0038810 A1 | 2/2008 | Pollack et al. |
| 2008/0050287 A1 | 2/2008 | Araragi et al. |
| 2008/0182301 A1 | 7/2008 | Handique et al. |
| 2008/0227185 A1 | 9/2008 | Schonfeld et al. |
| 2008/0230386 A1 | 9/2008 | Srinivasan et al. |
| 2008/0248590 A1 | 10/2008 | Gulliksen et al. |
| 2008/0274513 A1 | 11/2008 | Shenderov et al. |
| 2008/0283439 A1 | 11/2008 | Sullivan et al. |
| 2008/0314167 A1* | 12/2008 | Kahl .................. B01L 3/502707 73/864.91 |
| 2009/0022624 A1 | 1/2009 | Saltsman et al. |
| 2009/0061450 A1 | 3/2009 | Hunter |
| 2009/0148847 A1 | 6/2009 | Kokoris et al. |
| 2009/0155902 A1 | 6/2009 | Pollack et al. |
| 2009/0180931 A1 | 7/2009 | Silbert et al. |
| 2009/0182575 A1 | 7/2009 | Warner et al. |
| 2009/0197778 A1 | 8/2009 | Lepschi et al. |
| 2009/0221059 A1 | 9/2009 | Williams et al. |
| 2009/0221091 A1 | 9/2009 | Mogi et al. |
| 2009/0223989 A1 | 9/2009 | Gelardi |
| 2009/0263834 A1 | 10/2009 | Sista et al. |
| 2009/0298059 A1 | 12/2009 | Gumbach et al. |
| 2009/0304944 A1 | 12/2009 | Sudarsan et al. |
| 2009/0325276 A1 | 12/2009 | Battrell et al. |
| 2010/0025250 A1 | 2/2010 | Pamula et al. |
| 2010/0032293 A1 | 2/2010 | Pollack et al. |
| 2010/0035349 A1 | 2/2010 | Bau et al. |
| 2010/0048410 A1 | 2/2010 | Shenderov et al. |
| 2010/0068764 A1 | 3/2010 | Sista et al. |
| 2010/0087012 A1 | 4/2010 | Shenderov |
| 2010/0116640 A1 | 5/2010 | Pamula et al. |
| 2010/0120130 A1 | 5/2010 | Srinivasan et al. |
| 2010/0130369 A1 | 5/2010 | Shenderov et al. |
| 2010/0150783 A1 | 6/2010 | Araragi et al. |
| 2010/0151475 A1 | 6/2010 | Tanaami et al. |
| 2010/0178697 A1 | 7/2010 | Doebler et al. |
| 2010/0190263 A1 | 7/2010 | Srinivasan et al. |
| 2010/0194408 A1 | 8/2010 | Sturmer et al. |
| 2010/0206094 A1 | 8/2010 | Shenderov |
| 2010/0224511 A1 | 9/2010 | Boatner |
| 2010/0226199 A1 | 9/2010 | Mogi et al. |
| 2010/0233824 A1* | 9/2010 | Verhoeckx ........ B01L 3/502715 436/501 |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0288789 A1 | 11/2010 | Tanaami et al. |
| 2010/0291578 A1 | 11/2010 | Pollack et al. |
| 2010/0291588 A1 | 11/2010 | McDevitt et al. |
| 2010/0297754 A1 | 11/2010 | Solli et al. |
| 2010/0304986 A1* | 12/2010 | Chen ................. B01L 3/502715 506/9 |
| 2010/0307917 A1 | 12/2010 | Srinivasan et al. |

(56) References Cited

U.S. PATENT DOCUMENTS

| | | |
|---|---|---|
| 2010/0307922 A1 | 12/2010 | Wu |
| 2010/0308051 A1 | 12/2010 | Weber |
| 2010/0311599 A1 | 12/2010 | Wheeler et al. |
| 2010/0317093 A1 | 12/2010 | Turewicz et al. |
| 2010/0323405 A1 | 12/2010 | Pollack et al. |
| 2010/0331522 A1 | 12/2010 | Irvine et al. |
| 2011/0048951 A1 | 3/2011 | Wu |
| 2011/0053289 A1 | 3/2011 | Lowe et al. |
| 2011/0076692 A1 | 3/2011 | Sista et al. |
| 2011/0086377 A1 | 4/2011 | Thwar et al. |
| 2011/0091989 A1* | 4/2011 | Sista et al. ............ 436/174 |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0143339 A1* | 6/2011 | Wisniewski ...... B01L 3/5023 435/6.1 |
| 2011/0159578 A1 | 6/2011 | Godsey et al. |
| 2011/0180571 A1 | 7/2011 | Srinivasan et al. |
| 2011/0186433 A1 | 8/2011 | Pollack et al. |
| 2011/0186466 A1 | 8/2011 | Kurowski et al. |
| 2011/0203930 A1 | 8/2011 | Pamula et al. |
| 2011/0207621 A1 | 8/2011 | Montagu et al. |
| 2011/0209998 A1 | 9/2011 | Shenderov |
| 2011/0240471 A1 | 10/2011 | Wheeler et al. |
| 2011/0303542 A1 | 12/2011 | Srinivasan et al. |
| 2011/0311980 A1 | 12/2011 | Pollack et al. |
| 2011/0318824 A1 | 12/2011 | Tanaami et al. |
| 2011/0319279 A1 | 12/2011 | Montagu et al. |
| 2012/0018306 A1 | 1/2012 | Srinivasan et al. |
| 2012/0022695 A1 | 1/2012 | Handique et al. |
| 2012/0044299 A1 | 2/2012 | Winger |
| 2012/0064597 A1 | 3/2012 | Clemmens et al. |
| 2012/0071342 A1 | 3/2012 | Lochhead et al. |
| 2012/0083046 A1 | 4/2012 | Watson et al. |
| 2012/0085645 A1 | 4/2012 | Mousa et al. |
| 2012/0107811 A1 | 5/2012 | Kelso et al. |
| 2012/0122108 A1 | 5/2012 | Handique et al. |
| 2012/0132528 A1 | 5/2012 | Shenderov et al. |
| 2012/0142070 A1 | 6/2012 | Battrell et al. |
| 2012/0156112 A1 | 6/2012 | Sprague et al. |
| 2012/0156750 A1 | 6/2012 | Battrell et al. |
| 2012/0160826 A1 | 6/2012 | Handique |
| 2012/0164627 A1 | 6/2012 | Battrell et al. |
| 2012/0165238 A1 | 6/2012 | Pamula et al. |
| 2012/0171759 A1 | 7/2012 | Williams et al. |
| 2012/0177543 A1 | 7/2012 | Battrell et al. |
| 2012/0187117 A1 | 7/2012 | Weber |
| 2012/0196280 A1 | 8/2012 | Karlsen et al. |
| 2012/0252008 A1 | 10/2012 | Brown et al. |
| 2012/0261264 A1 | 10/2012 | Srinivasan et al. |
| 2012/0270305 A1* | 10/2012 | Reed et al. ............ 435/287.2 |
| 2012/0271127 A1 | 10/2012 | Battrell et al. |
| 2012/0329142 A1 | 12/2012 | Battrell et al. |
| 2013/0011912 A1 | 1/2013 | Battrell et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |
| 2013/0118901 A1 | 5/2013 | Pollack et al. |
| 2013/0130262 A1 | 5/2013 | Battrell et al. |
| 2013/0130936 A1 | 5/2013 | Eckhardt |
| 2013/0142708 A1 | 6/2013 | Battrell et al. |
| 2013/0146461 A1 | 6/2013 | Pamula et al. |
| 2013/0164742 A1 | 6/2013 | Pollack et al. |
| 2013/0178374 A1 | 7/2013 | Eckhardt et al. |
| 2013/0178968 A1 | 7/2013 | Sturmer et al. |
| 2013/0203606 A1 | 8/2013 | Pollack et al. |
| 2013/0217103 A1 | 8/2013 | Bauer |
| 2013/0217113 A1 | 8/2013 | Srinivasan et al. |
| 2013/0225450 A1 | 8/2013 | Pollack et al. |
| 2013/0225452 A1 | 8/2013 | Pollack et al. |
| 2013/0230875 A1 | 9/2013 | Pamula et al. |
| 2013/0233425 A1 | 9/2013 | Srinivasan et al. |
| 2013/0233712 A1 | 9/2013 | Pamula et al. |
| 2013/0252262 A1 | 9/2013 | Srinivasan et al. |
| 2013/0302787 A1 | 11/2013 | Agarwal et al. |
| 2013/0327672 A1 | 12/2013 | Kurowski et al. |
| 2013/0331298 A1 | 12/2013 | Rea |
| 2013/0341231 A1 | 12/2013 | Lange et al. |
| 2014/0000223 A1 | 1/2014 | Osterloh et al. |
| 2014/0000735 A1 | 1/2014 | Weber et al. |
| 2014/0045275 A1 | 2/2014 | Rothacher et al. |
| 2014/0160877 A1 | 6/2014 | Lange et al. |
| 2014/0170641 A1 | 6/2014 | Macemon |
| 2014/0194305 A1 | 7/2014 | Kayyem et al. |
| 2014/0220702 A1 | 8/2014 | Johnson et al. |
| 2014/0255275 A1 | 9/2014 | Barry et al. |
| 2014/0261708 A1 | 9/2014 | Wright et al. |
| 2014/0263439 A1 | 9/2014 | Wright et al. |
| 2014/0322706 A1 | 10/2014 | Kayyem et al. |
| 2015/0024436 A1 | 1/2015 | Eberhart et al. |
| 2015/0132860 A1 | 5/2015 | Cook et al. |
| 2015/0298118 A1 | 10/2015 | Chard et al. |
| 2015/0323555 A1 | 11/2015 | Kayyem et al. |
| 2015/0346097 A1 | 12/2015 | Battrell et al. |
| 2016/0129437 A1 | 5/2016 | Kayyem et al. |
| 2016/0129445 A1 | 5/2016 | Corey et al. |
| 2016/0130640 A1 | 5/2016 | Wright et al. |
| 2016/0146803 A1 | 5/2016 | Allen et al. |

FOREIGN PATENT DOCUMENTS

| | | | |
|---|---|---|---|
| EP | 0583833 A2 | 2/1994 | |
| EP | 0694483 B1 | 9/1998 | |
| EP | 0870541 A2 | 10/1998 | |
| JP | 2002518690 A | 6/2002 | |
| JP | 2002542461 A | 12/2002 | |
| JP | 2009134512 A | 6/2009 | |
| JP | 2009-161187 A | 7/2009 | |
| JP | 2009199617 A | 9/2009 | |
| JP | 2009534653 A | 9/2009 | |
| JP | 2010169693 A | 8/2010 | |
| JP | 2011520449 A | 7/2011 | |
| JP | 2011252768 A | 12/2011 | |
| JP | 2012055321 A | 3/2012 | |
| WO | WO 1999037819 | 7/1999 | |
| WO | WO 9967425 A2 | 12/1999 | |
| WO | WO 2000/062931 A1 | 10/2000 | |
| WO | WO 0062931 A1 | 10/2000 | |
| WO | WO 2001/010729 A1 | 2/2001 | |
| WO | WO 2004/011148 A2 | 2/2004 | |
| WO | WO 2004034028 A2 | 4/2004 | |
| WO | WO 2007044917 A2 | 4/2007 | |
| WO | WO 2007112114 A2 | 10/2007 | |
| WO | WO 2007120241 A2 | 10/2007 | |
| WO | WO 2009/089466 A2 | 7/2009 | |
| WO | WO 2009/140373 A2 | 11/2009 | |
| WO | WO 2009140373 A2 | 11/2009 | |
| WO | WO 2010/025302 A2 | 3/2010 | |
| WO | WO 2010069977 A1 | 6/2010 | |
| WO | WO 2010/151705 A2 | 12/2010 | |
| WO | WO 2011034668 A1 | 3/2011 | |
| WO | WO 2011106314 A2 | 9/2011 | |
| WO | WO 2011127040 A2 | 10/2011 | |
| WO | WO-2012054588 A2 * | 4/2012 | ........ G01R 33/281 |
| WO | WO 2012/080190 A2 | 6/2012 | |
| WO | WO 2012084615 A1 | 6/2012 | |
| WO | WO 2012117029 A1 | 9/2012 | |
| WO | WO 2012151192 A2 | 11/2012 | |
| WO | WO 2013059750 A1 | 4/2013 | |
| WO | WO 2014049371 A2 | 4/2014 | |
| WO | WO 2014066704 A1 | 5/2014 | |

OTHER PUBLICATIONS

Beaucage et al., "Tetrahedron Report No. 329: The Functionalization of Oligonucleotides via Phosphoramidite Derivatives," *Tetrahedron* vol. 49, No. 10, pp. 1925-2963 (1993).

Bolli et al., "α-Bicyclo-DNA: Synthesis, Characterization, and Pairing Properties of α-DNA-Analogues with Restricted Conformational Flexibility in the Sugar-Phosphate Backbone," *American Chemical Society*, pp. 100-117 (1994).

(56) References Cited

OTHER PUBLICATIONS

Brill et. al., "Synthesis of Oligodeoxynucleoside Phosphorodithioates via Thioamidites," *J. Am. Chem. Soc.*, pp. 2321-2322 (1989).
Carlsson et al., "Screening for Genetic Mutations" *Letters to Nature*, vol. 380, p. 207 (Mar. 1996).
Dempcy et al., "Synthesis of a Thymidyl Pentamer of Deoxyribonucleic Guanidine and Binding Studies with DNA Homopolynucleotides," *Proc. Natl. Acad. Sci. USA*, vol. 92, pp. 6097-6101 (Jun. 1995).
Egholm et al., "Peptide Nucleic Acids (PNA). Oligonucleotide Analogues with an Achiral Peptide Backbone," *J.Am.Chem.Soc.*, pp. 1895-1897 (1992).
Egholm et al., "PNA hybridizes to complementary oligonucleotides obeying the Watson-Crick hydrogen-bonding rules," *Letters to Nature*, pp. 566-568 (1993).
Herdewijn et al., "Hexopyranosyl-Like Oligonucleotides," *American Chemical Society*, pp. 80-99 (1994).
Horn et al., "Oligonucleotides with Alternating Anionic and Cationic Phosphoramidate Linkages: Synthesis and Hybridization of Stereo-Uniform Isomers," *Tetrahedron Letters*, vol. 37, No. 6, pp. 743-746 (1996).
Jeffs et al., "Unusual Confirmation of a 3-Thioformacetal Linkage in a DNA Duples," *Journal of Biomedecular NMR*, pp. 17-34 (1994).
Jenkins et al., "The Biosynthesis of Carbocyclic Nucleosides," *Chemical Society Reviews*, pp. 169-176 (Jan. 1995).
Kiedrowski et al., "Parabolic Growth of a Self-Replicating Hexadeoxynucleotide Bearing a 3'-5' Phosphoamidate Linkage," *Angew Chem. Intl. Ed. English 30*, pp. 423-426 (1991).
Koshkin et al., "LNA (Locked Nucleic Acid): An RNA Mimic Forming Exceedingly Stable LNA: LNA Duplexes," *J. Am. Chem. Soc.*, vol. 120, pp. 13252-13253 (1998).
Letsinger et al., "Phosphoramidate Analogues of Oligonucleotides," *J. Org. Chem*, vol. 35, No. 1, pp. 3800-3803 (1970).
Letsinger et al., "Effects of Pendant Groups at Phosphorus on Binding Properties of d-APA Analogues," *Nucleic Acids Research* vol. 14, No. 8, pp. 3487-3499 (1986).
Letsinger et al., "Caionic Oligonucleotides," *J. Am. Chem. Soc.*, pp. 4470-4471 (1988).
Letsinger et al., "Hybridization of Alternating Cationic/ Anionic Oligonucleotides to RNA Segments," *Nucleosides & Nucleotides* vol. 13, No. 6&7, pp. 1597-1605 (1994).
Maddry et al., "Synthesis of Nonionic Oligonucleotide Analogues," *American Chemical Society*, pp. 40-51 (1994).
Mag et al., "Synthesis and Selective Clevage of a Oligodeoxynucleotide Containing a Bridged Internucleotide 5 Phosphorothioate Linkage," *Nucleic Acids Research*, vol. 19 No. 7, pp. 1437-1441 (1991).
Meier et al., "Peptide Nucleic Acids (PNA's)—Unusual Properties of Nonionic Oligonucleotide Analogues," *Angew Intl. Ed. English 31*, No. 8, pp. 1008-1010 (1992).
Mesmaeker et al., "Comparison of Rigid and Flexible Backbones in Antisense Oligonucleotides," *Bioorganic & Medicinal Chem. Letters*, vol. 4, No. 3, pp. 395-398 (1994).
Mesmaeker et al., "Novel Backbone Replacements for Oligonucleotides," *American Chemical Society*, pp. 24-39 (1994).
Pauwels et al., "Biological Activity of New 2-5A Analogues," *Chemica Scripta*, vol. 26, pp. 141-145 (1986).
Rawls "Optomistic About Antisense," *C&EN*, pp. 35-39 (Jun. 1997).
Sawai, "Synthesis and Properties of Oligoadenylic Acids Containing 2'-5' Phosphoramide Linkage," *Chemistry Letters*, pp. 805-808 (1984).
Sprinzl et al., "Enzymatic Incorporation of ATP and CTP Analogues into the 3' end of RNA," *Eur. J Biochem 81*, pp. 579-589 (1977).
Notice of Allowance issued in U.S. Appl. No. 14/206,867, 52 pages (dated Jun. 10, 2015).
Supplemental Notice of Allowability issued in U.S. Appl. No. 14/206,867, 5 pages (dated Jul. 13, 2015).

International Search Report and Written Opinion issued in International Application No. PCT/US2013/06617, 35 pages (dated Feb. 3, 2014).
International Preliminary Report on Patentability and Written Opinion issued in International Application No. PCT/US2013/06617, 15 pages (dated Apr. 28, 2015).
Non-final Office Action issued in U.S. Appl. No. 14/062,860, 67 pages (dated Jul. 23, 2015).
International Search Report and Written Opinion issued in corresponding Application No. PCT/US2013/066717, 35 pages, (dated Feb. 3, 2014).
V. Ryan, "Flat Plate Cam / Linear Cam" [retrieved on Aug. 5, 2014] http://web.archive.org/web/20110302093447/http://www.technologystudent.com/cams/flat1.htm, 3 pages.
Notice of Allowance issued in U.S. Appl. No. 14/206,867, 43 pages (dated Aug. 7, 2015).
International Preliminary Report on Patentability issued in International Application No. PCT/US2014/024499, 9 pages (dated Sep. 24, 2015).
Non-final Office Action issued in U.S. Appl. No. 14/206,817, 44 pages (dated Oct. 8, 2015).
Extended European Search Report issued in European Patent Application No. 138496757, 5 pages (dated Oct. 12, 2015).
International Search Report and Written Opinion issued in International Patent Application No. PCT/US2014/024499, 14 pages (dated Dec. 11, 2014).
Dobson et al., "Emerging Technologies for Point-of-Care Genetic Testing," *Future Drugs Ltd* (www.future-drugs.com), 10.1586/14737159.7.4.359, Expert Rev. Mol. Diagn., pp. 359-370 (2007).
Doebler et al., "Continuous-Flow, Rapid Lysis Devices for Biodefense Nucleic Acid Diagnostic Systems," *The Association for Laboratory Automation* (JALA), pp. 119-125 (Jun. 2009).
Erickson et al., "Integrated Microfluidic Devices," *Elsevier B.V.*, 16 pages (2003).
Findlay et al., "Automated Closed-Vessel System for in Vitro Diagnostics Based on Polymerase Chain Reaction," *Clinical Chemistry*, 39:9, pp. 1927-1933, 1993).
Focke et al., "Lab-on-a-Foil: Microfluidics on Thin and Flexible Films," *The Royal Society of Chemistry*, pp. 1365-1386 (2010).
Malic et al., "Current State of Intellectual Property in Microfluidic Nucleic Acid Analysis," McGill University, *Bentham Science Publishers*, 18 pages (2007).
Vandeventer et al., "Mechanical Disruption of Lysis-Resistant Bacterial Cells by Use of a Miniature, Low-Power, Disposable Device," American Society for Microbiology, *Journal of Clinical Microbiology*, 49:7, pp. 2533-2539 (Jul. 2011).
Office Action issued in U.S. Appl. No. 14/206,867, 22 pages (dated Nov. 7, 2014).
Extended European Search Report issued in European Patent Application No. 16151365.0, 4 pages (dated May 23, 2016).
International Search Report and Written Opinion issued in International Patent Application No. PCT/US2015/059978, 23 pages (dated Jun. 27, 2016).
Notice of Allowance issued in U.S. Appl. No. 14/206,903, 16 pages (dated May 11, 2016).
Wolf et al., "Single-Tube Nested PCR with Room-Temperature-Stable Reagents," Cold Spring Harbor Laboratory Press ISSN, 1054-9803/95, vol. 4, pp. 376-379 and source page (1995).
Non-final Office Action issued in U.S. Appl. No. 14/206,903, 47 pages (dated Jan. 21, 2016).
Final Office Action issued in U.S. Appl. No. 14/062,860, 32 pages (dated Feb. 11, 2016).
Notice of Allowance issued in U.S. Appl. No. 14/206,817, 20 pages (dated Feb. 19, 2016).
Invitation to Pay Additional Fees and, Where Applicable, Protest Fee, including partial international search results, issued by the International Searching Authority in International Patent Application No. PCT/US2015/059947, 13 pages (Feb. 23, 2016).
Invitation to Pay Additional Fees and, Where Applicable, Protest Fee, including partial international search results, issued by the International Searching Authority in International Patent Application No. PCT/US2015/059978, 10 pages (Feb. 23, 2016).

(56) References Cited

OTHER PUBLICATIONS

European Patent Office Communication Pursuant to Article 94(3) EPC in European Patent Application No. 15168733.2, 3 pages (dated Feb. 19, 2016).
Extended European Search Report issued in European Patent Application No. 15168733.2, 3 pages (dated Dec. 15, 2015).
Notice of Allowance issued in U.S. Appl. No. 14/538,565, 55 pages (dated Jul. 11, 2016).
Supplemental Notice of Allowance issued in U.S. Appl. No. 14/206,817, 3 pages (dated Jul. 12, 2016).
Corrected Notice of Allowance issued in U.S. Appl. No. 14/538,565, 10 pages (dated Jul. 29, 2016).
Advisory Action issued in U.S. Appl. No. 14/062,860, 7 pages (dated Jul. 21, 2016).
Office Action (and English translation) issued in Chinese Patent Application No. 201480027615.1, 9 pages (dated Aug. 11, 2016).
Communication 94(3) EPC issued in European Patent Application No. 13849675.7, 3 pages (dated Oct. 6, 2016).
Office Action (with English translation) issued in Chinese Patent Application No. 2014800227615.1, 11 pages (dated Feb. 14, 2017).
Notice of Allowance issued in U.S. Appl. No. 14/538,533, 59 pages (dated Nov. 10, 2016).
Advisory Action issued in U.S. Appl. No. 14/062,860, 6 pages (dated Jan. 19, 2017).
International Search Report and Written Opinion issued in International Patent Application No. PCT/US2015/059947, 31 pages (dated Apr. 21, 2017).
Non-final Office Action issued in U.S. Appl. No. 14/807,000, 69 pages (dated May 1, 2017).
Non-final Office Action issued in U.S. Appl. No. 14/538,506, (dated Jun. 14, 2017), 68 pages.
International Preliminary Report on Patentability issued in International Patent Application No. PCT/US2015/059947, (dated May 26, 2017), 12 pages.
International Preliminary Report on Patentability issued in International Patent Application No. PCT/US20152015/059978), (dated May 26, 2017), 17 pages.
Notice of Reasons for Rejection (with English translation) issued in Japanese Patent Application No. 2015539818, (dated Jul. 4, 2017) 8 pages.
Non-final Office Action issued in U.S. Appl. No. 14/948,819, (dated Sep. 14, 2017), 70 pages.
Non-final Office Action issued in U.S. Appl. No. 15/227,188, (dated Oct. 10, 2017), 13 pages.
Examination Report issued in Australian Patent Application No. 2014235532, 3 pages (dated Aug. 28, 2017).
Examination Report issued in Australian Patent Application No. 2013334189, 4 pages (dated Sep. 11, 2017).
Office Action (Japanese language) issued in Japanese Patent Application No. 2016-501554, 3 pages (dated Nov. 28, 2017). Concise Explanation of Relevance attached.
Office Action (Japanese language) issued in Japanese Patent Application No. 2017-039634, 2 pages (dated Nov. 29, 2017). Concise Explanation of Relevance attached.
Office Action (Japanese language) issued in Japanese Patent Application No. 2017-039635, 4 pages (dated Jan. 15, 2018). Concise Explanation of Relevance attached.
Corrected Notice of Allowability issued in U.S. Appl. No. 14/538,506, (dated Feb. 9, 2018), 9 pages.
Final Office Action issued in U.S. Appl. No. 14/807,000, (dated Feb. 6, 2018), 38 pages.
Final Office Action issued in U.S. Appl. No. 14/948,819, (dated Feb. 7, 2018), 11 pages.
The definition of "paddle" provided by the online dictionary at dictionary.com [retrieved on Jan. 31, 2018]. Retrieved from the Internet: <URL: www.dictionary.com/browse/paddle>.

* cited by examiner

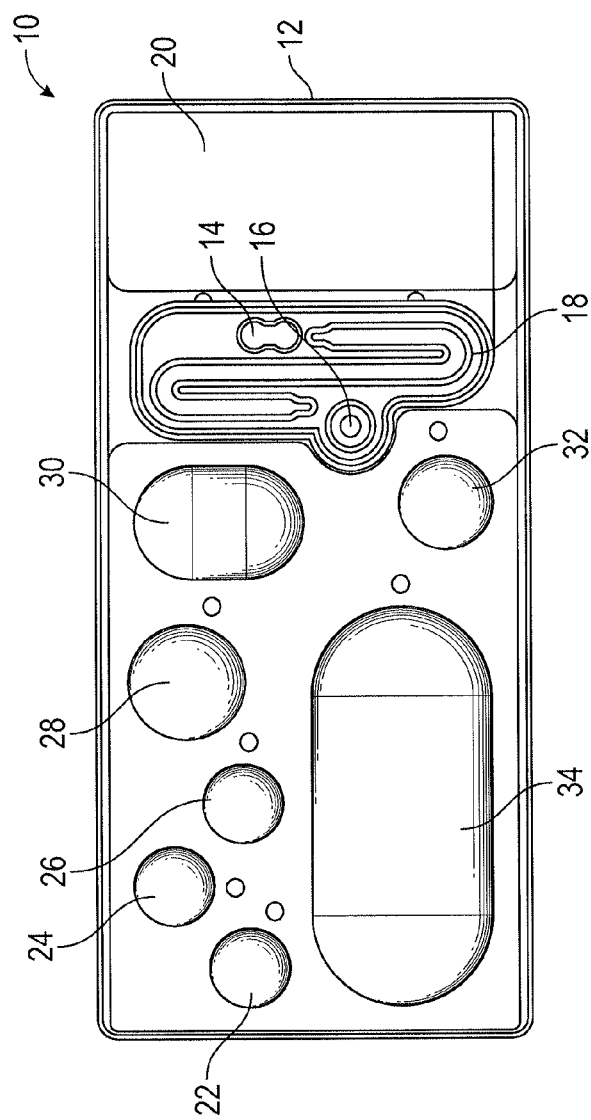
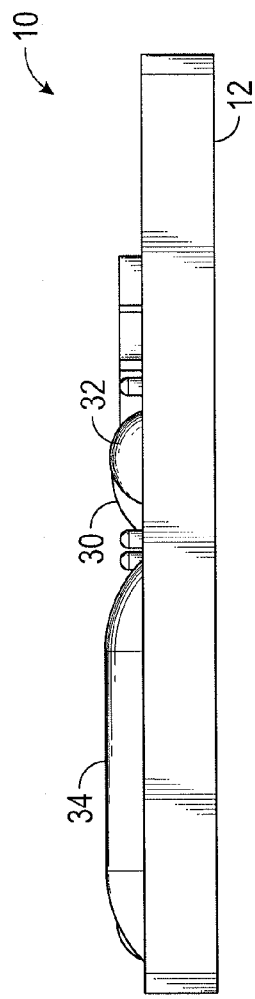
FIG. 1A
FIG. 1B

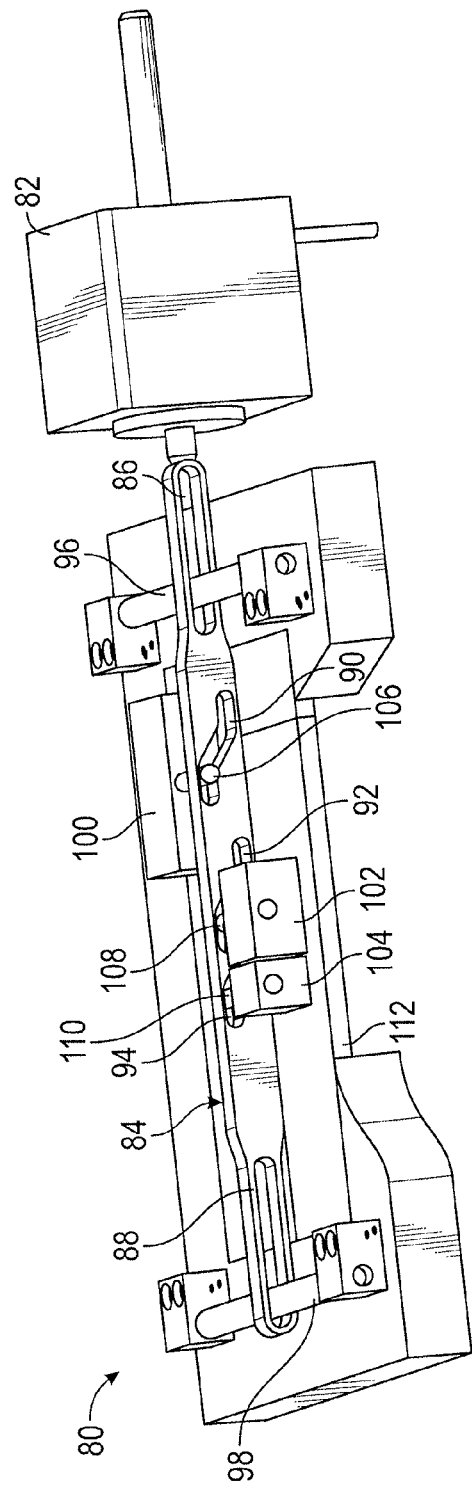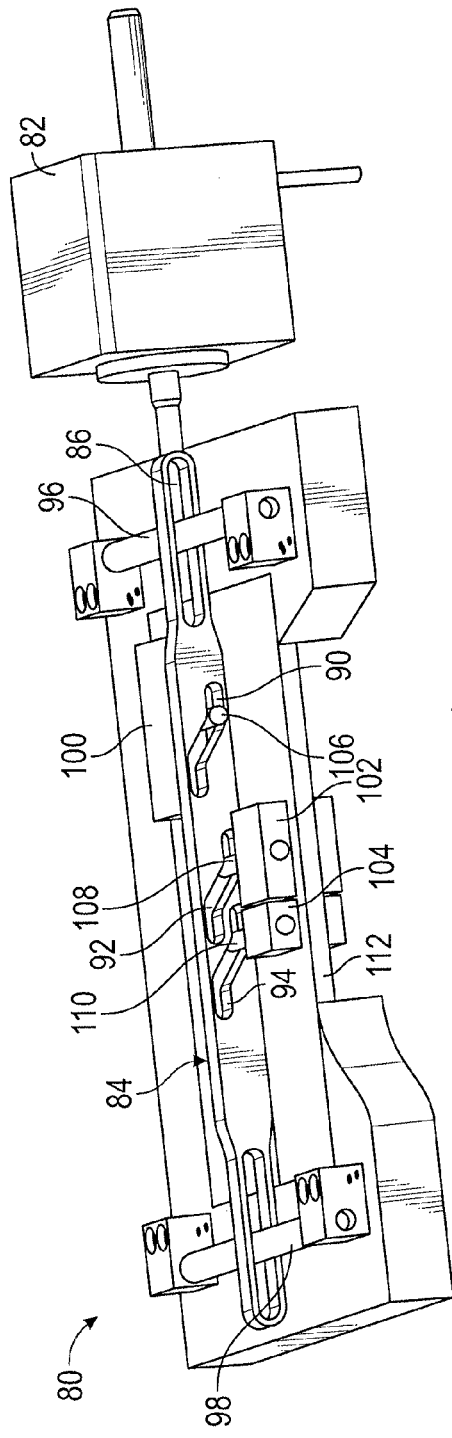
FIG. 7A
FIG. 7B

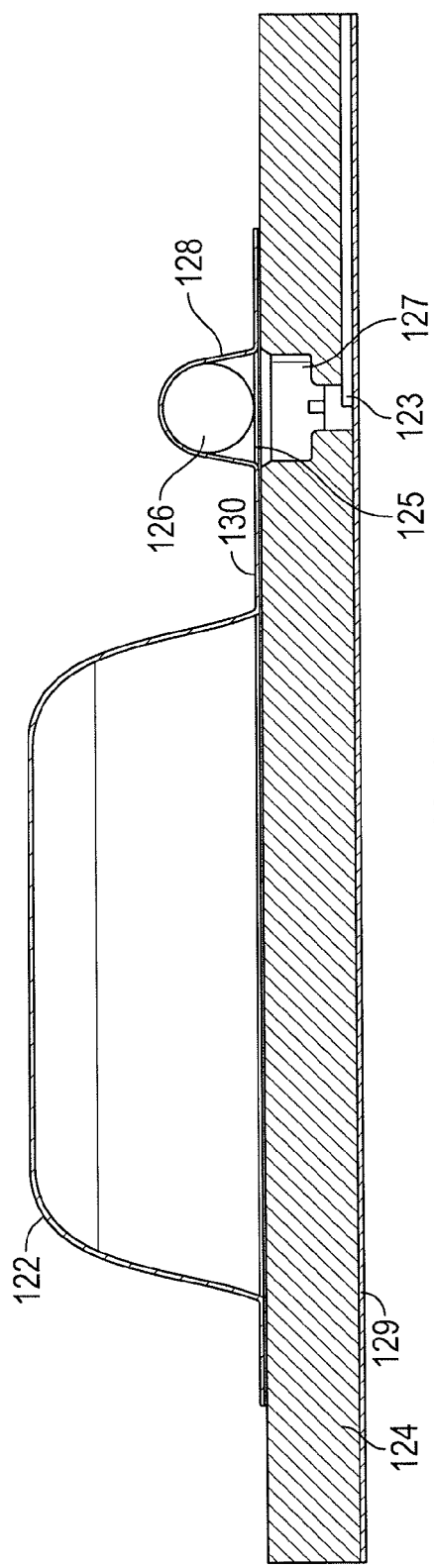
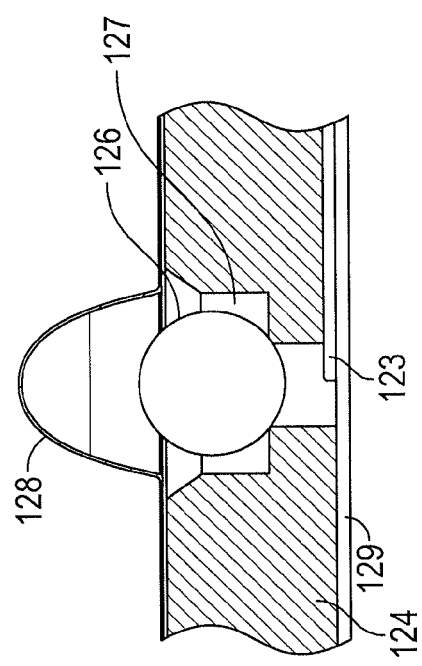

| ACTOR | CATEGORY | ACTION | VOLUME |
|---|---|---|---|
| Operator | Sample Introdution | Load sample, cap, insert consumable into system | |
| LRM | Sample Prep | Add lysis buffer to sample | Lysis buffer- 300μl |
| LRM | Sample Prep | Mix sample and lysis buffer | |
| LRM | Sample Prep | Actuate mixed sample and lysis buffer through bead beater | |
| LRM | Sample Prep | Add binding buffer and mag particles to lysed sample | |
| LRM | Sample Prep | Mix lysed sample with binding buffer and mag particles | Binding buffer - 500 μl |
| LRM | Sample Prep | Filler fluid delivered to cartridge | 3 mL |
| LRM | Sample Prep | Capture of magnetic particles | |
| LRM | Sample Prep | Washing of magnetic particles | Wash buffer-- 200 μl |
| LRM | Sample Prep | Release magnetic particles | |
| LRM | Sample Prep | Magnetic particles delivered to sample prep chamber on cartridge | Wash buffer-- 200 μl |
| ... | ... | ... | ... |

FIG. 33A

| ... | ... | ... | ... |
|---|---|---|---|
| LRM | Sample Prep | Wash buffer delivered to wash buffer dispenser on cartridge | Wash buffer-- 100µl |
| LRM | Sample Prep | Reconstitution buffer delivered elution buffer dispenser to cartridge | Reconst/Elution buffer- 200 µl |
| CART | Sample Prep | Magnetic particles mixed in sample prep chamber | 200µl |
| CART | Sample Prep | Magnetic particles captured | N/A |
| CART | Sample Prep | Wash buffer dispensed, transported and combined with magnetic particles | 12 µl |
| CART | Sample Prep | Magnetic particles with wash buffer transported back and forth | 12 µl |
| CART | Sample Prep | Magnetic particle captured | |
| CART | Sample Prep | Wash buffer removed from magnetic particles | 12 µl |
| CART | Sample Prep | Elution buffer dispensed, transported and combined with magnetic particles | 6 µl |
| CART | Sample Prep | Elution buffer with magnetic beads moved around for elution | 6 µl |
| CART | Sample Prep | Magnetic particles removed from elution volume | 6 µl |
| ... | ... | ... | ... |

FIG. 33B

| ... | ... | ... | ... |
|---|---|---|---|
| CART | RT-PCR | Elution buffer dispensed and transported to dried RT/PCR buffer | 6 μl |
| CART | RT-PCR | Dried RT/PCR buffer rehydrated | 6 μl |
| CART | RT-PCR | Reconstituted RT/PCR buffer transported to dried PCR enzyme | 6 μl |
| CART | RT-PCR | Dried PCR enzyme reconstituted | 6 μl |
| CART | RT-PCR | Dispense 6 1 μl aliquots of master mix and transport to appropriate dried primer cocktail | 6 x 1 μl |
| CART | RT-PCR | Split 6 1 μl aliquots of eluted DNA and combine with 1μl master mix aliquots | 6 x 1 μl |
| CART | RT-PCR | RT/PCR performed | 6 x 2 μl |
| CART | EXO | Elution buffer dispensed and transported to dried to exonuclease | 6 μl |
| CART | EXO | Dried exonuclease rehydrated | 6 μl |
| CART | EXO | 1 μl aliquots of rehydrated EXO dispensed and transported to each PCR reaction | 6 x 1 μl |
| CART | EXO | Exonuclease performed | 6 x 3 μl |
| ... | | | ... |

FIG. 33C

| | | | |
|---|---|---|---|
| ... | ... | ... | ... |
| CART | Detection | Elution buffer dispensed and transported to dried detection buffer | 75 |
| CART | Detection | Rehydrated detection buffer aliquoted and transported to dried signal probes | 3 x 15 µl |
| CART | Detection | Dried signal probes rehydrated | 3 x 15 µl |
| CART | Detection | ExoD PCR reactions transported to rehydrated signal probe detection buffer | 6 x 3 µl |
| CART | Detection | ExoD PCR reactions mixed with rehydrated detection buffer | 3 x 21 µl |
| CART | Detection | Detection solution dumped into eSensor zones | 3 x 21 µl |
| CART | Detection | Hybridization mixing | 3 x 21 µl |
| CART | Detection | Detection scanning | 3 x 21 µl |

FIG. 33D

INTEGRATED MULTIPLEX TARGET ANALYSIS

CROSS-REFERENCE TO RELATED APPLICATIONS

This application claims the benefit of provisional patent applications Ser. No. 61/717,887, filed Oct. 24, 2012, and Ser. No. 61/798,091, filed Mar. 15, 2013, both of which are hereby incorporated by reference in their entirety, and particularly for the Figures and Legends contained therein.

BACKGROUND OF THE INVENTION

One major challenge in the area of clinical and molecular diagnostics is the ability to have a "sample to answer" system that allows minimal sample handling and preparation, rapid assays as well as no requirement for highly trained laboratory personnel. While many systems have been proposed, to date there are virtually no such commercial systems. The present invention provides such an integrated, multiplex system.

BRIEF SUMMARY OF THE INVENTION

The present invention provides biochip cartridges and instrument devices for the detection and/or analysis of target analytes from patient samples.

Accordingly, in one aspect, the present invention provides biochip cartridges generally comprising a bottom substrate and a top plate. The bottom substrate comprises a printed circuit board (PCB) comprising an electrowetting grid of electrodes forming a droplet pathway, an array of detection electrodes accessible to the droplet pathway, each comprising a self-assembled monolayer and a capture probe, and a plurality of interconnections from the electrowetting grid and the detection electrodes. The top plate comprises a conductive surface substantially parallel to the bottom substrate and mated thereto to form a reaction chamber. In a further aspect, the bottom substrate further comprises a plurality of amplification pathways of electrowetting pads. In an additional aspect, some of the pads of the electrowetting grid comprise dried assay reagents. These can include, but are not limited to, deoxyribonucleotide triphosphates (dNTPs; usually a mixture of dCTP, dTTP, dGTP and dATP); sets of PCR primers, label probes, enzymes (reverse transcriptase (in the case where the target nucleic acid is RNA), exonucleases, polymerases (particularly heat stable enzymes such as Taq polymerase and variants thereof, as well as "Hot Start" embodiments).

In a further aspect, the array of detection electrodes in is fluid communication with the droplet pathway.

In a further aspect, the top plate can comprise fluid passageways spatially corresponding to the intended receiving pads of the electrowetting grid.

In an additional aspect, the cartridge further comprises a liquid regent module (LRM) comprising a plurality of blisters comprising assay reagents, fluid passageways connecting each of said blisters to one of the fluid holes of the top plate, and a sample inlet port in fluid connection with the reaction chamber. In some aspects, the LRM further comprises an aliquot of capture beads, particularly magnetic capture beads. In an additional aspect, the fluid passageways of the LRM allow the assay reagents stored in the blisters to be dispensed at a location remote from the blister upon rupture of the blister. In a further aspect, the blisters of the LRM can contain an immiscible fluid, particularly immiscible oil, lysis buffer, binding buffer and/or elution buffer.

In a further aspect, the biochip cartridge further comprises an external housing comprising a latched cover for irreversibly sealing the sample inlet port. In some aspects, the external housing further comprises electronic connections from the edge interconnectors of the bottom substrate and/or from the thermal zone connections. In an additional aspect, the external housing is asymmetrically shaped to facilitate only one insertion orientation into the bays of the devices herein. In a further aspect, the external housing can further comprise a barcode.

The present invention further provides methods of using the biochips of the invention. Thus, in one aspect, the invention provides methods of detecting a plurality of target nucleic acids in a sample comprising adding sample to the biochips of the invention, executing steps to lyse the cells of the sample, purify the sample, amplify the sample, and detect the sample, with optional washing steps at any or all operations.

In one aspect, the methods provide adding the sample to a biochip cartridge of the invention and executing assay operations comprising mixing the sample with lysis buffer, adding binding buffer and capture beads to the sample, mixing the beads and sample, optionally washing the beads, eluting the target nucleic acids from the beads, adding amplification reagents to the target nucleic acids to amplifying the target nucleic acids to form amplicons, optionally digesting one strand of the amplicon using exonuclease, adding signaling probes to the amplicons to form hybridization complexes, binding the hybridization complexes to the capture probes on the detection electrodes to form assay complexes, optionally washing the detection electrodes, and electrochemically detecting the assay complexes.

In a further aspect, the invention provides an apparatus for the detection of target analytes comprising: a) an instrument bank comprising a plurality of biochip cartridge bays for insertion and analysis of a biochip cartridge; b) a touch screen display having a plurality of bay icons, each icon uniquely corresponding to one of the plurality of bays; wherein when a biochip cartridge is inserted into one of said bays the corresponding icon is enlarged and/or exhibited.

In an additional aspect, the invention provides an apparatus for the detection of target analytes comprising: a) an instrument bank comprising a plurality of biochip cartridge bays for insertion and analysis of a biochip cartridge; b) a touch screen display having a plurality of bay icons, each bay icon uniquely corresponding to one of the plurality of bays; wherein when one of said bay icons is touched a panel of first options about the corresponding bay is enlarged and/or exhibited.

In a further aspect the plurality of biochip cartridge bays are arranged in at least one vertically disclosed bank of bays, and the bay icons are similarly displayed. Similarly, the plurality of biochip cartridge bays can be arranged in at least two vertically disclosed banks of bays, and the bay icons are similarly displayed. Additionally, the plurality of biochip cartridge bays can be arranged in at least three vertically disclosed banks of bays, and the bay icons are similarly displayed. Similarly, the plurality of biochip cartridge bays can be arranged in at least four vertically disclosed banks of bays, and the bay icons are similarly displayed.

In an additional aspect, the panel of first options comprises a plurality of secondary icons each selected from the group consisting of: an icon to review biochip cartridge data; an icon for status of a biochip cartridge assay; an icon depicting the time remaining in a biochip cartridge assay; an icon to generate a data report of biochip cartridge data; an icon to print a data report of biochip cartridge data; an icon to email a data report of biochip cartridge data; an icon to export a data report of biochip cartridge data to another computer device; and an icon to display a virtual keyboard.

In a further aspect, the apparatus further comprises a lighting component associated with each biochip cartridge bays. The lighting component indicates the status of the bay, which status can independently and optionally be selected from the group consisting of empty, cartridge present, cartridge assay underway, cartridge assay complete, and error.

In an additional aspect, the apparatus further comprises a barcode reader and/or one or more USB ports. In some cases a barcode scanner is attached via a USB port.

In a further aspect, each biochip cartridge bay is independently controlled.

In an additional aspect, each biochip cartridge is ejected upon completion of the assay protocol.

In a further aspect, the touch screen display further comprises a row of function icons. These function icons can independently and optionally be selected from the group consisting of: a function icon to display a virtual keyboard, a preventative maintenance icon; a dashboard icon, a print icon; an email icon, and an icon to export data to a remote device. The preventative maintenance icon can be a dashboard icon, which, when pressed will display a plurality of graphs each selected from the group consisting of [number of assays run], [number of assays for one or more bays], [number and/or type of assays run for each bay], [time since last maintenance for each bay] and [number of errors per bay]. The graphs can be selected from bar graphs and pie chart graphs.

In an additional aspect, each bay comprises at least a first off resistive chip heater and/or a second off chip Peltier heater. In some cases, each bay comprises three resistive heaters configured to facilitate PCR reactions on the chip. In some cases, the Peltier heater services the detection electrodes.

In a further aspect, the memory of the apparatus stores user profiles, which can optionally include the retention of the preferred height of the virtual keyboard display.

In an additional aspect, the invention provides biochip cartridges comprising: a housing comprising a plurality of physical force contacts; a first bottom substrate comprising printed circuit board (PCB) comprising: a plurality of detection electrodes comprising capture binding ligands; a plurality of electrowetting electrodes; interconnects for the detection and electrowetting electrodes; a second top substrate comprising plastic comprising: a plurality of reactant wells, optionally containing reagent well inlet ports; at least one sample inlet port; wherein the first and second substrate form at least one chamber (which can be varying heights in different locations due to the top plate configuration).

In a further aspect, the detection electrodes each comprise a capture binding ligand (including nucleic acids and proteins).

In an additional aspect, the detection electrodes further comprise a self-assembled monolayer (SAM).

In a further aspect, one of the reagent wells/locations contains a solution binding ligand comprising at least one electron transfer moiety (ETM), which can be a metallocene, including ferrocenes, which includes ferrocene derivative.

In an additional aspect, the target analytes are target nucleic acids and at least one of the reagent wells comprises a set of PCR primers for a plurality of the target nucleic acids.

In a further aspect, the first substrate comprises at least a first identification tag such as an EPROM, an EEPROM, an RFID, a barcode, a 2D barcode, etc., that identifies the biochip and/or the assay on the biochip.

In an additional aspect, the housing comprises a location to add a patient barcode. The housing can be asymmetrically configured such that it can only be inserted into the bays in one direction.

In a further aspect, the inlet port has an associated sealable lid, which can be reversibly or irreversibly sealable.

In an additional aspect, the invention provides methods of diagnosis based on detecting at least one target analyte of a plurality of target analytes comprising: providing an apparatus according to any claim herein, providing a patient sample; providing a biochip cartridge according to any of the cartridge claims herein; adding the patient sample to the inlet port; sealing said inlet port; adding a patient barcode to said housing; scanning said patient barcode into said apparatus; inserting said cartridge into one of said bays; initiating the appropriate assay; and generating a report showing the diagnosis.

As described herein, in one aspect the invention provides an apparatus for processing a fluid module including a collapsible vessel supported on a planar substrate by applying a force compressing the vessel against the substrate, said apparatus comprising: a first actuator component configured to be movable in a first direction that is generally parallel to the plane of the substrate; a second actuator component configured to be movable in a second direction having a component that is generally normal to the plane of the substrate; and a motion conversion mechanism coupling the first actuator component with the second actuator component and constructed and arranged to convert movement of the first actuator component in the first direction into movement of the second actuator component in the second direction.

In one aspect, the first actuator component comprises an actuator plate configured to be movable in the first direction and including a cam follower element; the second actuator component comprises a platen configured to be movable in the second direction; and the motion conversion mechanism comprises a cam body having a cam surface, said cam body being coupled to said platen and being configured such that the cam follower element of the actuator plate engages the cam surface of the cam body as the actuator plate moves in the first direction thereby causing movement of the cam body that results in movement of the platen in the second direction.

In an additional aspect, the cam follower element of the actuator plate comprises a roller configured to rotate about an axis of rotation that is parallel to the actuator plate and normal to the first direction; and the motion conversion mechanism further comprises a chassis, and the cam body is pivotally attached at one portion thereof to the chassis and at another portion thereof to the platen.

In a further aspect, the cam surface of the cam body comprises an initial flat portion and a convexly-curved portion, and movement of the roller from the initial flat portion to the convexly-curved portion causes the movement of the cam body that results in movement of the platen in the second direction.

In an additional aspect, the first actuator component comprises a cam rail configured to be movable in the first direction; the second actuator component comprises a platen configured to be movable in the second direction; and the motion conversion mechanism comprises a cam surface and a cam follower coupling the cam rail to the platen and configured to convert motion of the cam rail in the first direction into movement of the platen in the second direction.

In a further aspect, the cam surface comprises a cam profile slot formed in the cam rail; and the cam follower comprises a follower element coupling the platen to the cam profile slot such that movement of the cam rail in the first direction causes movement of the cam follower within the cam profile slot that results in the movement of the platen in the second direction.

In an additional aspect, the invention provides an apparatus for displacing fluid from a fluid container including a first vessel and a second vessel connected or connectable to the first vessel and including a sealing partition preventing fluid flow from the second vessel, wherein the fluid container further includes an opening device configured to be contacted with the sealing partition to open the sealing partition and permit fluid flow from the second vessel, said apparatus comprising: a first actuator configured to be movable with respect to the first vessel to compress the first vessel and displace fluid contents thereof; and a second actuator movable with respect to the opening device and configured to contact the opening device and cause the opening device to open the sealing partition, wherein the second actuator is releasably coupled to the first actuator such that the second actuator moves with the first actuator until the second actuator contacts the opening device and causes the opening device to open the sealing partition, after which the second actuator is released from the first actuator and the first actuator moves independently of the second actuator to displace fluid from the first vessel.

In a further aspect, the invention provides a fluid container comprising: a first vessel; a second vessel connected or connectable to the first vessel; a sealing partition preventing fluid flow from the second vessel; and a spherical opening element initially supported within the second vessel by the sealing partition and configured to be contacted with the sealing partition to open the sealing partition and permit fluid flow from the second vessel.

In an additional aspect, the apparatus further comprises a fluid channel extending between the first and second vessels.

In a further aspect, the apparatus further comprises a seal within the fluid channel, the seal being configured to be breakable upon application of sufficient force to the seal to thereby connect the first and second vessels via the fluid channel.

In an additional aspect, the invention provides a fluid container comprising: a first vessel; a second vessel connected or connectable to the first vessel; a sealing partition preventing fluid flow from the second vessel; and a cantilevered lance having a piercing point and disposed with the piercing point adjacent to the sealing partition and configured to be deflected until the piercing point pierces the sealing partition to permit fluid flow from the second vessel.

In a further aspect, the fluid container further comprises a fluid channel extending between the first and second vessels.

In a further aspect, the apparatus further comprises a seal within the fluid channel, the seal being configured to be breakable upon application of sufficient force to the seal to thereby connect the first and second vessels via the fluid channel.

In an additional aspect, the invention provides a fluid container comprising: a first vessel; a second vessel connected or connectable to the first vessel; a sealing partition preventing fluid flow from the second vessel; and a cantilevered lance having a piercing point and being fixed at an end thereof opposite the piercing point, said cantilevered lance being disposed with the piercing point adjacent to the sealing partition and configured to be deflected until the piercing point pierces the sealing partition to permit fluid flow from the second vessel.

In a further aspect, the fluid container further comprises a substrate on which the first and second vessels are supported and which includes a chamber formed therein adjacent said sealing partition, wherein an end of the cantilevered lance is secured to the substrate and the piercing point of the lance is disposed within the chamber.

In an additional aspect, the fluid container further comprises a fluid channel extending between the first and second vessels.

In a further aspect, the fluid container further comprises a seal within the fluid channel, the seal being configured to be breakable upon application of sufficient force to the seal to thereby connect the first and second vessels via the fluid channel.

In an additional aspect, the invention provides a fluid container comprising: a first vessel; a second vessel connected or connectable to the first vessel; a sealing partition preventing fluid flow from the second vessel; and a lancing pin having a piercing point and disposed with the piercing point adjacent to the sealing partition and configured to be moved with respect to the sealing partition until the piercing point pierces the sealing partition to permit fluid flow from the second vessel.

In a further aspect, the lancing pin has a fluid port formed therethrough to permit fluid to flow through the lancing pin after the sealing partition is pierced by the piercing point.

In an additional aspect, the fluid container further comprises a substrate on which the first and second vessels are supported and which includes a chamber formed therein adjacent said sealing partition within which the lancing pin is disposed.

In a further aspect, the chamber comprises a segmented bore defining a hard stop within the chamber and said lancing pin includes a shoulder that contacts the hard stop to prevent further movement of the lancing pin after the piercing point pierces the sealing partition.

In an additional aspect, the fluid container further comprises a fluid channel extending between the first and second vessels.

In an additional aspect, the fluid container further comprises a seal within the fluid channel, the seal being configured to be breakable upon application of sufficient force to the seal to thereby connect the first and second vessels via the fluid channel.

In a further aspect, the invention provides a fluid container comprising: a first vessel; a second vessel disposed within the first vessel; a substrate on which the first and second vessels are supported and having a cavity formed therein adjacent said second vessel; a fixed spike formed within the cavity; and a fluid exit port extending from the cavity, wherein said first and second vessels are configured such that external pressure applied to the first vessel will collapse the second vessel and cause the second vessel to contact and be pierced by the fixed spike, thereby allowing fluid to flow from the first vessel through the cavity and the fluid exit port.

In an additional aspect, the invention provides a fluid container comprising: a collapsible vessel configured to be collapsed upon application of sufficient external pressure to displace fluid from the vessel; a housing surrounding at least a portion of the collapsible vessel; and a floating compression plate movably disposed within said housing, wherein said housing includes an opening configured to permit an external actuator to contact the floating compression plate within the housing and press the compression plate into the collapsible vessel to collapse the vessel and displace the fluid contents therefrom.

BRIEF DESCRIPTION OF THE DRAWINGS

FIG. 1A is a top plan view of a liquid reagent module, according to one of the embodiments of the present invention.

FIG. 1B is a side view of the liquid reagent module shown in FIG. 1A.

FIG. 7A is a perspective view of an alternative embodiment of a blister compressing actuator mechanism in an unactuated state.

FIG. 7B is a perspective view of the blister compressing actuator mechanism of FIG. 7A in the fully actuated state.

FIG. 8A is a partial, cross-sectional side view of a collapsible fluid vessel configured to facilitate opening of the vessel.

FIG. 8B is an enlarged partial, cross-sectional side view of a vessel opening feature of the collapsible fluid vessel.

FIGS. 33A, 33B, 33C, and 33D are portions of a table showing an overview of the operation steps for an exemplary assay run on the system of the invention.

DETAILED DESCRIPTION OF THE INVENTION

I. Introduction

Figure 2:
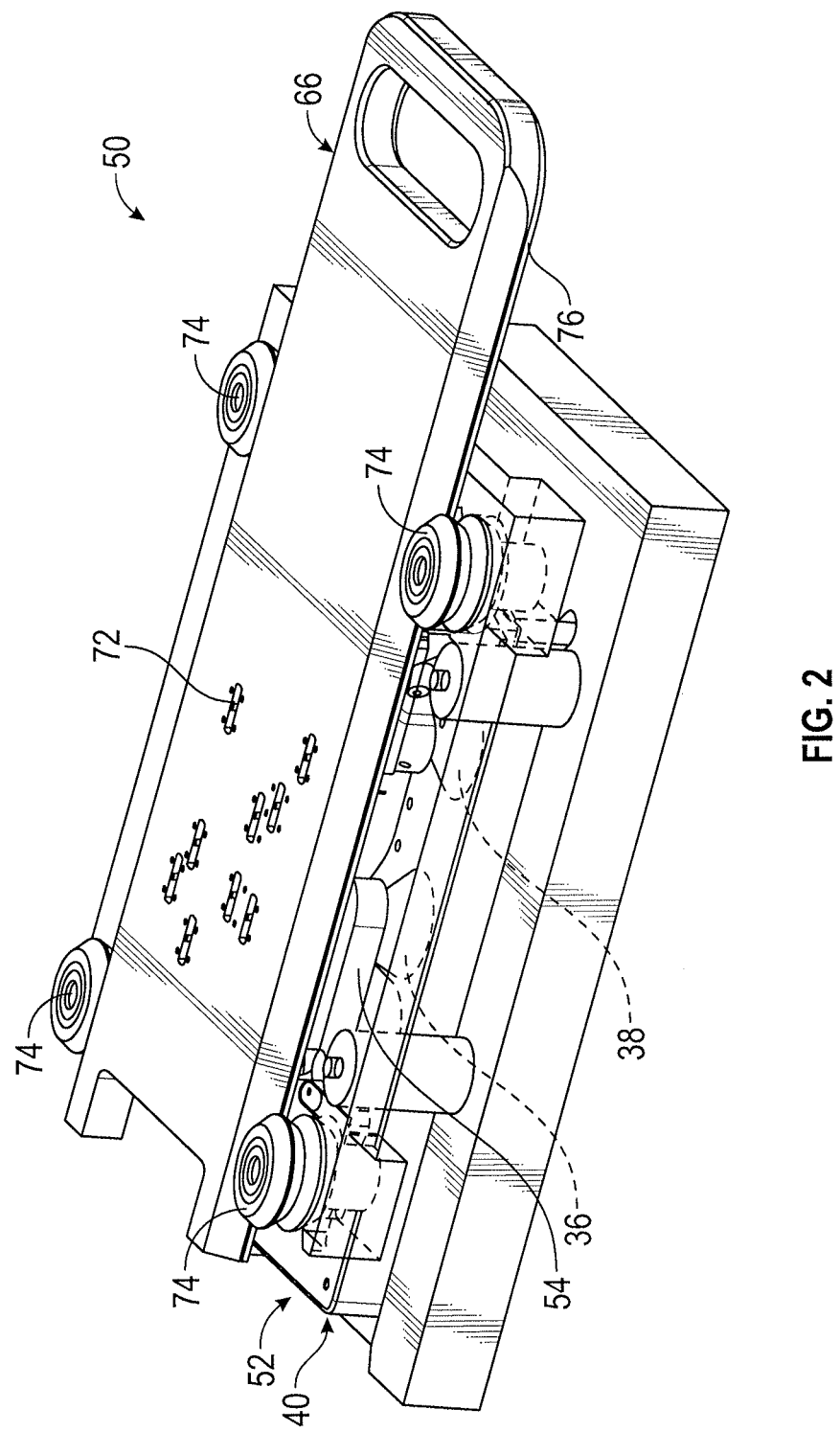
FIG. 2 is a perspective view of a blister compressing actuator mechanism embodying aspects of the present invention.

One major challenge in the area of clinical and molecular diagnostics is the ability to have a "sample to answer" system that allows minimal sample handling and preparation as well as no requirement for trained clinical lab personnel. While many systems have been proposed, to date there are virtually no such commercial systems. The present invention provides such an integrated, multiplex system. One of the significant benefits of the present system is that in many embodiments, the chip itself needs no moving parts, such as valves or pumps, due to the unique transport properties of the electrowetting system described below.

The present invention provides molecular diagnostic methods and compositions based on the detection of target analytes, including nucleic acids. The systems described herein are complete integrated "sample to answer" systems, in contrast with current commercial systems that require some off chip handling of the sample, generally including sample extraction (cell lysis, for example), and sample preparation prior to detection. Thus, in the current system, a patient sample is loaded onto the cartridges of the invention and the target analyte sample is extracted, amplified as necessary (for example, when the target analyte is a nucleic acid using polymerase chain reaction (PCR) techniques, although isothermal amplification methods can be utilized as well), and then detected using electrochemical detection, all on a microfluidic platform, generally referred to herein as an "integrated biochip cartridge", "biochip" or "cartridge".

In general, the system relies on two components: the cartridge, into which the sample is loaded and processed, and the apparatus into which the cartridge is inserted to result in the sample processing and final detection of the target analytes and the generation of a report to such.

The basic microfluidic platform used herein is based on systems developed by Advanced Liquid Logic (ALL, currently a subsidiary of Illumina, Inc.), as more fully described below. In general, these technologies rely on the formation of microdroplets and the ability to independently transport, merge, mix and/or process the droplets, using electrical control of surface tension (i.e., electrowetting). In general, liquid samples are contained within a microfluidic device between two parallel plates. One plate contains etched drive electrodes on its surface while the other plate contains either etched electrodes or a single, continuous plane electrode that is grounded or set to a reference potential ("biplanar electrowetting"). Hydrophobic insulation covers the electrodes and an electric field is generated between electrodes on opposing plates. This electric field creates a surface-tension gradient that causes a droplet overlapping the energized electrode to move towards that electrode. In some embodiments, the active electrowetting electrodes may be adjacent and on the same plane as the neighboring ground reference electrode, which is referred to as "coplanar electrowetting"). Through proper arrangement and control of the electrodes, a droplet can be transported by successively transferring it between adjacent electrodes. The patterned electrodes can be arranged in a two dimensional array so as to allow transport of a droplet to any location covered by that array. The space surrounding the droplets may be filled with a gas such as air or an immiscible fluid such as oil, with immiscible oils being preferred in many embodiments of the present invention.

As the droplets containing the target analytes move across the surface, they can pick up reagents and buffers. For example, when dried reagents are placed on the bottom substrate (generally described herein as printed circuit board, although as will be appreciated by those in the art, additional substrates can be used), a droplet moving through that zone will pick up and dissolve the reagent for use in a biological process such as PCR amplification. In addition, as more fully described below, addition from the liquid reagent module ("LRM"), positioned above the substrate, allows for specific addition of buffers and other reagents such as wash buffers, etc. to droplets captured at specific locations.

One of the significant benefits of the present system is that in many embodiments, the chip itself needs no moving parts, such as valves or pumps, due to the unique transport properties of the electrowetting system.

The electrowetting technology integrates well with the electrochemical detection of target analytes as the addition of electrodes for detection and the lack of any optical requirements allows for superior and less expensive results. Suitable electrochemical detection systems are described in U.S. Pat. Nos. 4,887,455; 5,591,578; 5,705,348; 5,770,365; 5,807,701; 5,824,473; 5,882,497; 6,013,170; 6,013,459; 6,033,601; 6,063,573; 6,090,933; 6,096,273; 6,180,064; 6,190,858; 6,192,351; 6,221,583; 6,232,062; 6,236,951; 6,248,229; 6,264,825; 6,265,155; 6,290,839; 6,361,958; 6,376,232; 6,431,016; 6,432,723; 6,479,240; 6,495,323; 6,518,024; 6,541,617; 6,596,483; 6,600,026; 6,602,400; 6,627,412; 6,642,046; 6,655,010; 6,686,150; 6,740,518; 6,753,143; 6,761,816; 6,824,669; 6,833,267; 6,875,619; 6,942,771; 6,951,759; 6,960,467; 6,977,151; 7,014,992; 7,018,523; 7,045,285; 7,056,669; 7,087,148; 7,090,804; 7,125,668; 7,160,678; 7,172,897; 7,267,939; 7,312,087; 7,381,525; 7,381,533; 7,384,749; 7,393,645; 7,514,228; 7,534,331; 7,560,237; 7,566,534; 7,579,145; 7,582,419; 7,595,153; 7,601,507; 7,655,129; 7,713,711; 7,759,073; 7,820,391; 7,863,035; 7,935,481; 8,012,743; 8,114,661 and U.S. Pub. No. 2012/0181186, all of which are expressly incorporated herein by reference. Specific reference is made to the structure and synthesis of the ETMs, the different assay methods and assay components (particularly the structure and synthesis of label probes), the methods of making the PCB component and detection electrodes, etc.

Accordingly, the processed target analyte droplets are transported to a detection zone on the substrate, where they are specifically captured on individual detection electrodes, using systems described in numerous patents above with specific reference to U.S. Pat. No. 7,935,481, hereby expressly incorporated by reference and more fully described below. This detection system relies on the use of label probes (in the case of nucleic acids) containing electrochemically active labels, such that the presence of the target analyte results in a positive signal, allowing detection of the pathogen, disease state, etc.

The cartridge is then inserted into an apparatus, more fully described below, that receives the cartridge(s) and detects the presence or absence of the labels at each electrode, allowing the detection of the target analytes of interest, and reporting on the disease state, etc.

A particular utility of the present system is the ease and rapidity of this integrated system. For example, there are no more than 2 operations required before introduction of the sample to the system, which allows for both ease of use and no requirement for highly trained lab personnel. A significant benefit to the present system is also the speed from sample to answer, which is generally no more than about 45-90 minutes from sample introduction to reporting of assay results, with most results being reported in roughly 60-70 minutes or less. This represents a significant advantage to both labs and doctors relying on quick analyses for diagnosis and start of appropriate treatments. In addition, as outlined below, the ability of running not only multiple tests which are highly multiplexed on a single cartridge but the ability to analyze multiple cartridges in a completely random access way is a significant advantage in a clinical lab setting. A further advantage of the present system is that it can be used for point-of-care (POC) diagnostics. Each bay can be autonomously operated with minimal user operations, power requirements, and easy portability. A single bay can run multiple cartridge and assay combinations. Furthermore, some of the components (e.g., heaters and sensors) can be incorporated into the cartridge at minimal cost, thus allowing for easy and rapid assay development without altering the bay structure.

It should be noted that any and all components of the apparatus, biochip cartridge, methods, etc., can be individually included or excluded in each composition or method. That is, biochip cartridges without liquid reagents can be made, without heaters, etc.

Accordingly, the present invention is directed to integrated biochip systems that allow for the detection of target analytes from samples.

Samples

The invention provides apparatus (also referred to herein as "devices" or "systems") for the detection of target analytes in samples to diagnose disease, infection by pathogens (e.g. bacteria, virus, fungi, etc.). As will be appreciated by those in the art, the sample solution may comprise any number of things, including, but not limited to, bodily fluids (including, but not limited to, blood, urine, serum, plasma, cerebrospinal fluid, lymph, saliva, nasopharyngeal samples, anal and vaginal secretions, feces, tissue samples including tissues suspected of containing cancerous cells, perspiration and semen of virtually any organism, with mammalian samples being preferred and human samples being particularly preferred); environmental samples (including, but not limited to, air, agricultural, water and soil samples, environmental swabs and other collection kits); biological warfare agent samples; food and beverage samples, research samples (i.e. in the case of nucleic acids, the sample may be the products of an amplification reaction, including both target and signal amplification as is generally described in PCT/US99/01705 (WO 99/037819), such as PCR amplification reaction); purified samples, such as purified genomic DNA, RNA, proteins, etc.; raw samples (bacteria, virus, genomic DNA, etc.); as will be appreciated by those in the art, virtually any experimental manipulation may have been done on the sample.

The biochip cartridges of the invention are used to detect target analytes in patient samples. By "target analyte" or "analyte" or grammatical equivalents herein is meant any molecule or compound to be detected and that can bind to a binding species, defined below. Suitable analytes include, but not limited to, small chemical molecules such as environmental or clinical chemical or pollutant or biomolecule, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including prokaryotic (such as pathogenic bacteria) and eukaryotic cells, including mammalian tumor cells), viruses, spores, etc.

In one embodiment, the target analyte is a protein ("target protein"). As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants. Particularly preferred target proteins include enzymes; drugs; cells; antibodies; antigens; cellular membrane antigens and receptors (neural, hormonal, nutrient, and cell surface receptors) or their ligands.

In a preferred embodiment, the target analyte is a nucleic acid ("target nucleic acid"). The present system finds use in the diagnosis of specific pathogens exogenous to a patient such as bacteria and viruses, as well as the diagnosis of genetic disease, such as single nucleotide polymorphisms (SNPs) that cause disease (e.g. cystic fibrosis) or are present in disease (e.g. tumor mutations).

As will be appreciated by those in the art, the present invention relies on both target nucleic acids and other nucleic acid components like capture probes and label probes used in the detection of the target nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs can be included as primers or probes that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Left. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); those with bicyclic structures including locked nucleic acids, Koshkin et al., J. Am. Chem. Soc. 120:13252-3 (1998); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention, in general for use as capture and label probes. In addition, mixtures of naturally occurring nucleic acids and analogs can be made (e.g. in general, the label probes contain a mixture of naturally occurring and synthetic nucleotides).

The nucleic acids may be single stranded or double stranded, as specified, or contain portions of both double stranded or single stranded sequence. The nucleic acids (particularly in the case of the target nucleic acids) may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleoside analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As will be appreciated by those in the art, a large number of analytes may be detected using the present methods; basically, any target analyte for which a binding ligand, described below, may be made may be detected using the methods of the invention.

Thus, the systems of the invention are used in assays of target analytes that then allow the diagnosis, prognosis or treatment options of disease based on the presence or absence of the target analytes. For example, the systems of the invention find use in the diagnosis or characterization of pathogen infection (including bacteria (both gram positive and gram negative bacteria, and/or the ability to distinguish between them), viruses (including the presence or absence of viral nucleic acid as well as the isotypes of the virus, for example in the case of hepatitis C virus (HCV) or respiratory viruses), fungal infection, genetic diseases (including cystic fibrosis, sickle cell anemia, etc.). Included in the definition of genetic disease for the purposes of this invention are genetic conditions that do not necessarily cause disease but can result in an alternative treatment options. For example, single nucleotide polymorphisms (SNPs) in many cytochrome p450 enzymes cause different therapeutic drug processing, such as in the case of warfarin testing, where a patient may be diagnosed as a "slow", "normal" or "fast" processor, leading to different dosage regimes, or where a drug may be contraindicated for a particular patient based on the patient's genetics, or where selection between two or more drugs is aided by the knowledge of patient's genetics.

The present invention provides cartridges comprising several components, including a bottom substrate, a top plate, a liquid reagent module (LRM), and a housing that keeps the components together.

II. Biochip Cartridges

Figure 20:
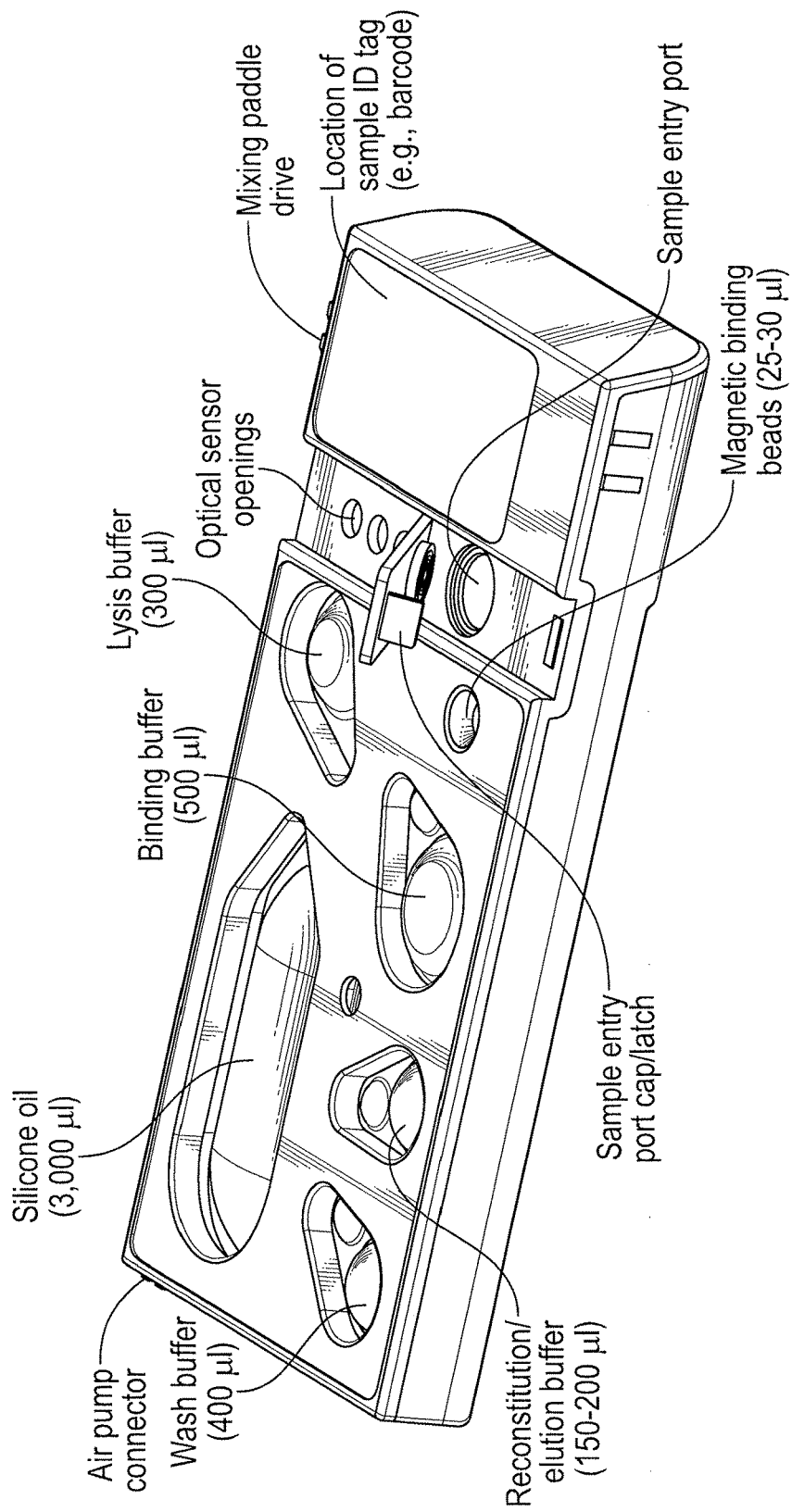
FIG. 20 is an annotated, top perspective view of one embodiment of the cartridge.

FIG. 20 is an annotated, top perspective view of one embodiment of the biochip cartridge. As shown in FIG. 20, a cartridge may include compartments, or blisters, containing silicone oil, binding buffer, lysis buffer, magnetic binding beads, reconstitution/elution buffer, and wash buffer. The cartridge may further include an air pump connector, optical sensor openings, a mixing paddle, as sample entry port, and a sample ID label area.

Figure 21:
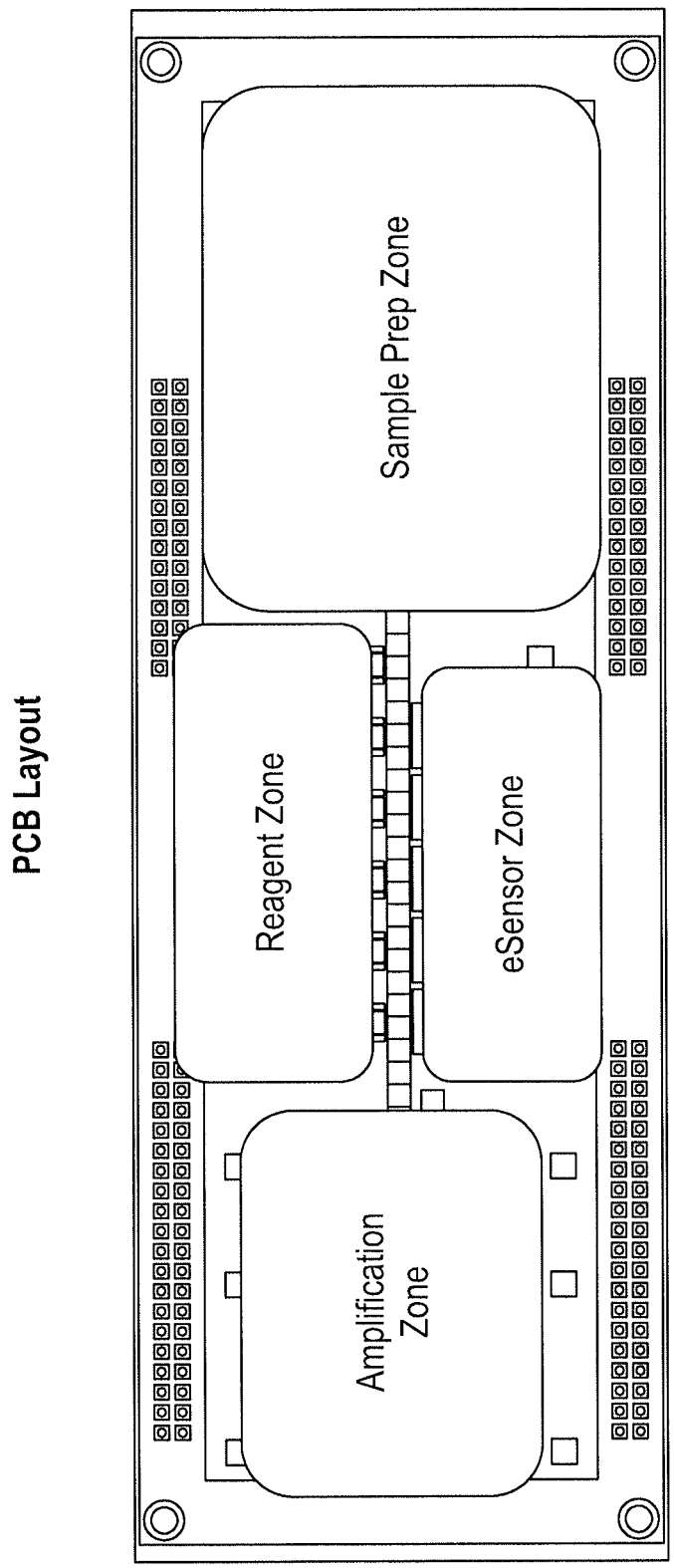
FIG. 21 is a schematic view of a PCB of one biochip of the invention.

FIG. 21 shows a PCB layout of one biochip bottom substrate of the invention, depicting four general "zones" of this embodiment. The sample preparation zone is connected to a housing inlet port to allow the introduction of sample. The sample preparation zone optionally includes lysis buffer for the lysis of cells and/or viruses in the patient sample, or the lysis buffer can be contained in the LRM, described herein. Magnetic beads are optionally included (again in the LRM), optionally coated such that the target analytes adsorb to the beads. For example, in the case of nucleic acids, the beads are coated such that the negatively charged nucleic acids absorb, and then can be optionally washed (e.g. by holding the beads in place using a magnetic actuator as described herein and flowing wash buffer past this holding zone) and optionally eluted (again, generally by holding the beads in place and flowing a high salt concentration buffer past the beads). Optionally, the washed beads can just be flowed into the system to be included in droplets. The Reagent zone is where reagents (enzymes, binding ligands, labels, primers, probes, buffers, wash buffers, etc.) are stored, either as dried reagents or as confined liquids or in blister packages above the surface, which, when burst, release the reagents into these zones, or both. The processing zone (labeled herein as the amplification zone as the target analytes are nucleic acids in this particular embodiment) is where the electrowetting fluidic technology allows the microdroplets to travel over different thermal zones (in this case, provided by resistive heaters in the bottom bay where the chip contacts the bay, although in some embodiments, on-chip heaters and sensors, such as resistive copper traces or thin-film thermocouples, could be utilized) to facilitate PCR. The eSensor™ zone is where the detection occurs as described herein. In some embodiments, as described herein, a Peltier element or a resistive heater is included (again, preferably within the bay, but in some embodiments could on-chip as well).

Figure 22:
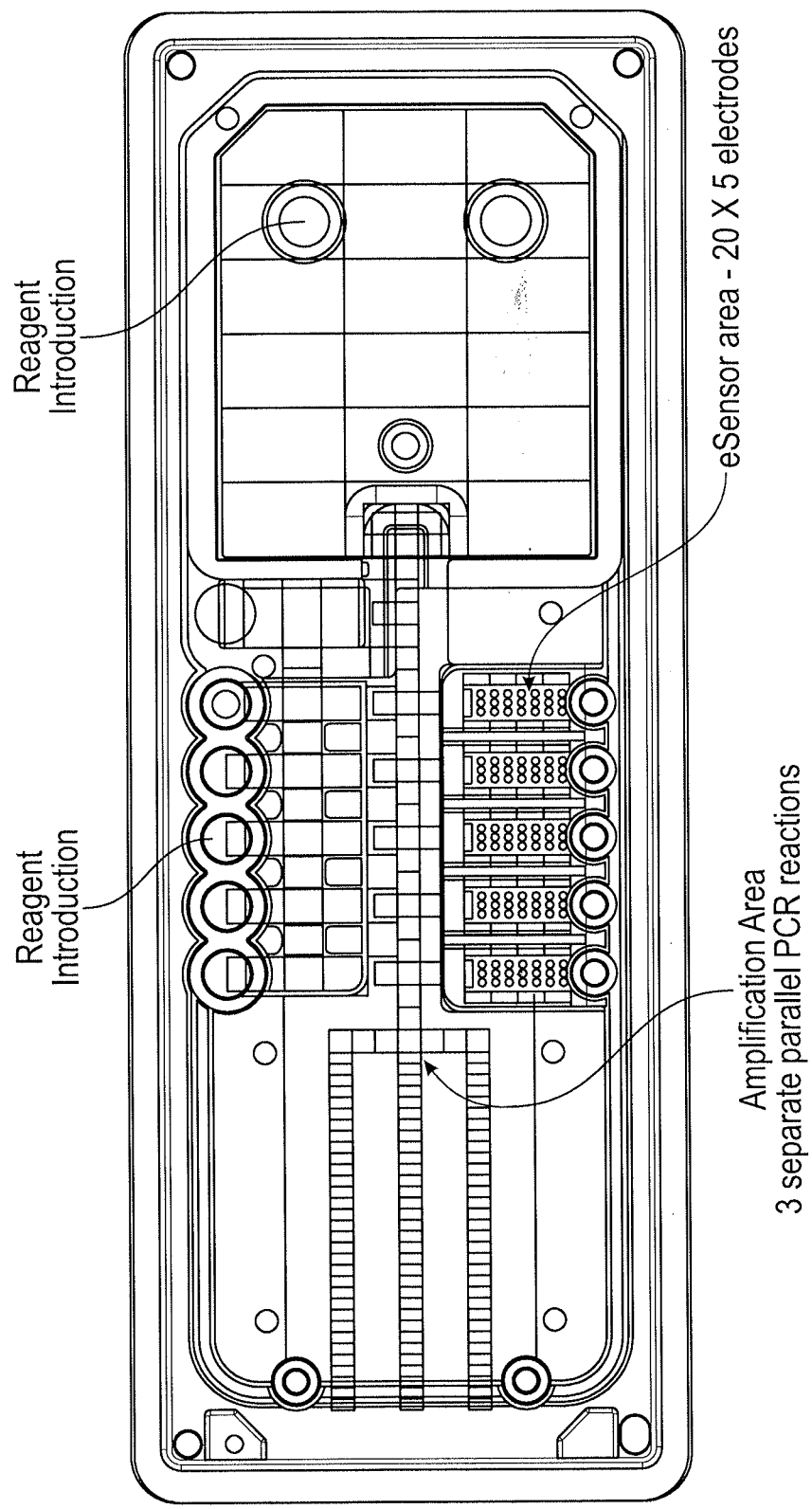
FIG. 22 is top plan view of one embodiment of the biochip of the invention.
Figure 30B:
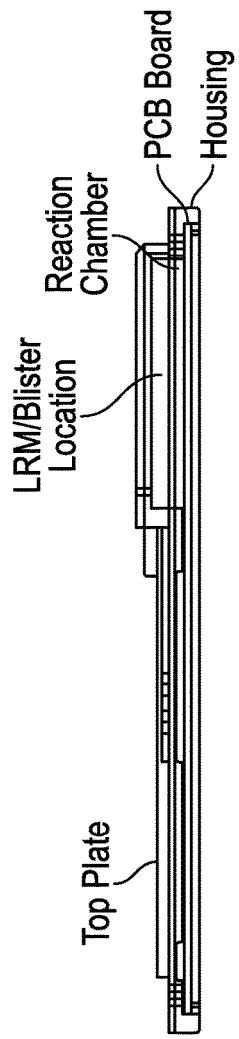
FIG. 30B is a side view of an embodiment of a biochip of the invention.
Figure 30A:
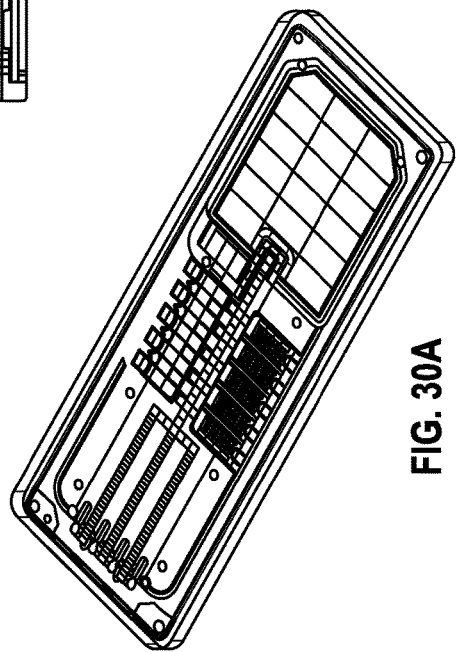
FIG. 30A is a top perspective view of an embodiment of a biochip of the invention.
Figure 30C:
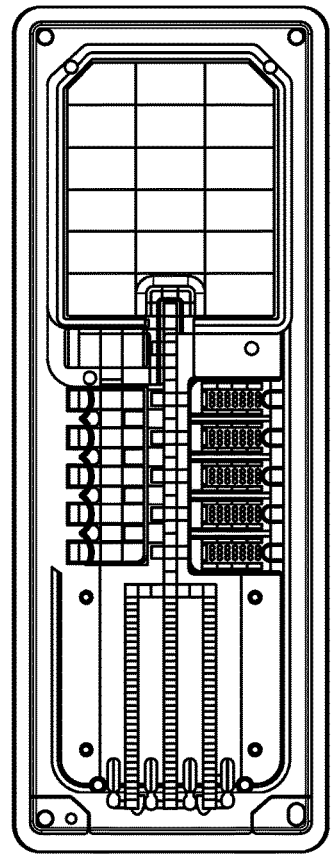
FIG. 30C is a top plan view of an embodiment of a biochip of the invention.

FIG. 22 is another rendering of one of the embodiments of the present biochip invention. Several optional manual reagent introduction ports are shown. As shown in FIGS. 30A, 30B, and 30C, the introduction ports may have blister packages (or other methods of storing reagents) above the zones, resident in the LRM and accessible to the chamber formed by the substrate and the top plate using holes or vias in the top plate, which optionally include one way valves to prevent sample from entering the LRM. As shown in FIG. 22, the amplification area is divided into three zones, that can be used individually (e.g. three droplets are processed essentially simultaneously) or together (e.g. one droplet is processed on the three tracks). This can allow, for example, one 21-plex reaction to be run as a group, or as 3×7-plex reactions; in some cases, particularly when multiplex PCR reactions are done, lowering the multiplexity of the reactions (e.g. primer sets, etc.) can give better results. It will also be appreciated by those in the art that multiple droplets may be used in each PCR track, e.g., 2, 3, 4 or more droplets per track (for example which may be combined together either prior to or during dispersement on the detection zone. In addition, as noted herein, these amplification areas need not be PCR reactions, isothermal amplification techniques can also be used.

Figure 35A:
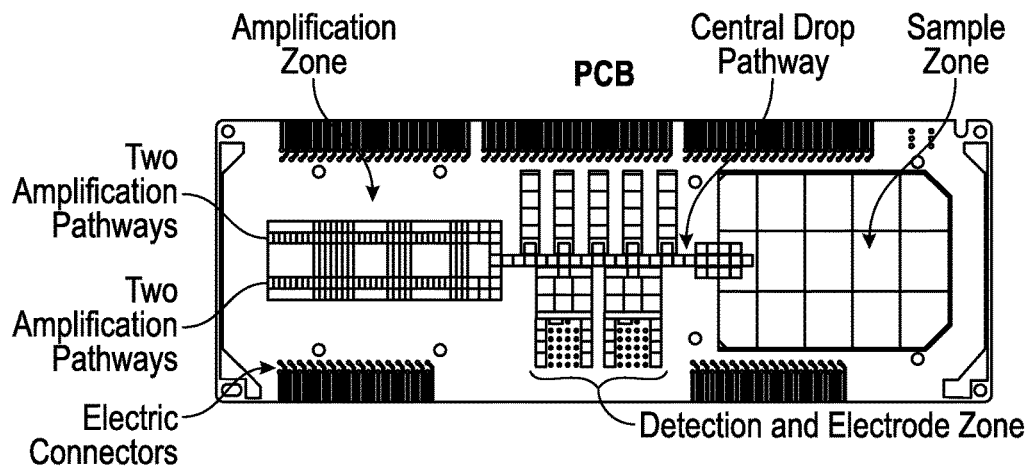
FIG. 35A is a top plan view of one embodiment of the PCB of the biochip cartridge.
Figure 35B:
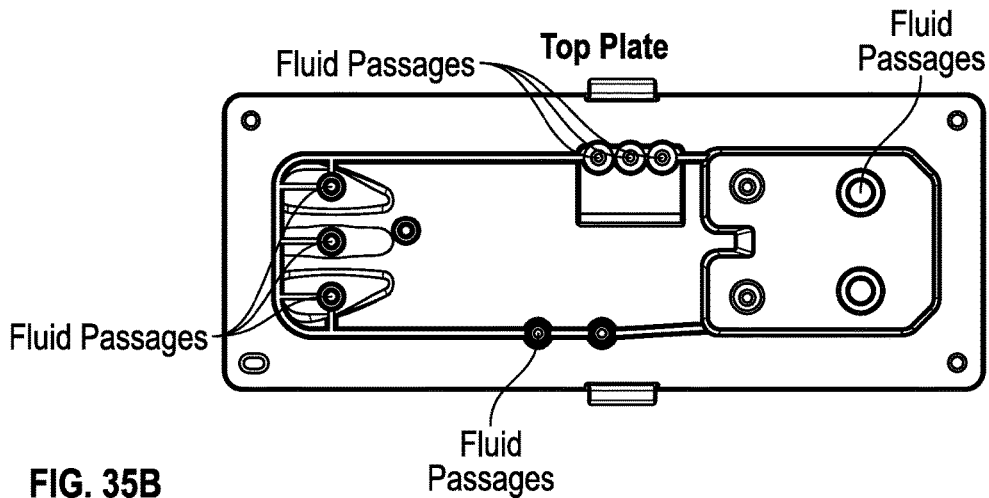
FIG. 35B is a top plan view of one embodiment of the top plate the biochip cartridge.
Figure 35C:
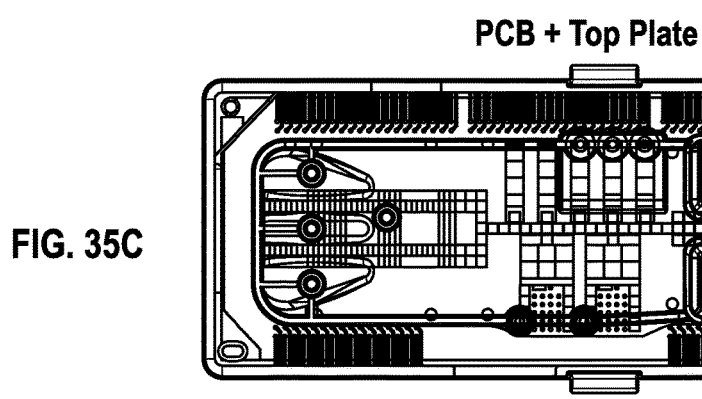
FIG. 35C is a top plan view of one embodiment of the PCB and the top mated together.

FIGS. 35A, 35B and 35C show a schematic of one embodiment of the PCB, the top plate, and the two mated together. FIG. 35B shows that the top plate has ridges such that the chamber height is different at different locations on the substrate.

Figure 23A:
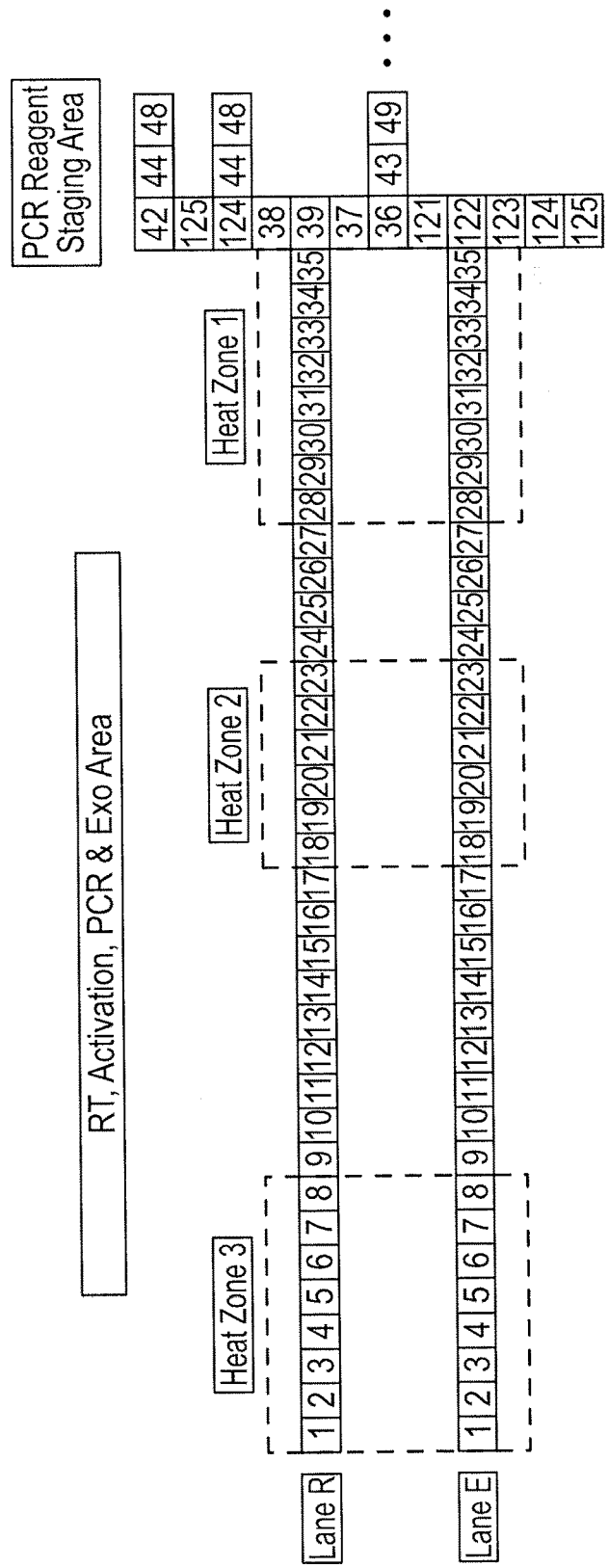
FIG. 23A schematically depicts a portion of an electrowetting grid of one configuration of the bottom substrate of the cartridge of the invention.
Figure 23B:
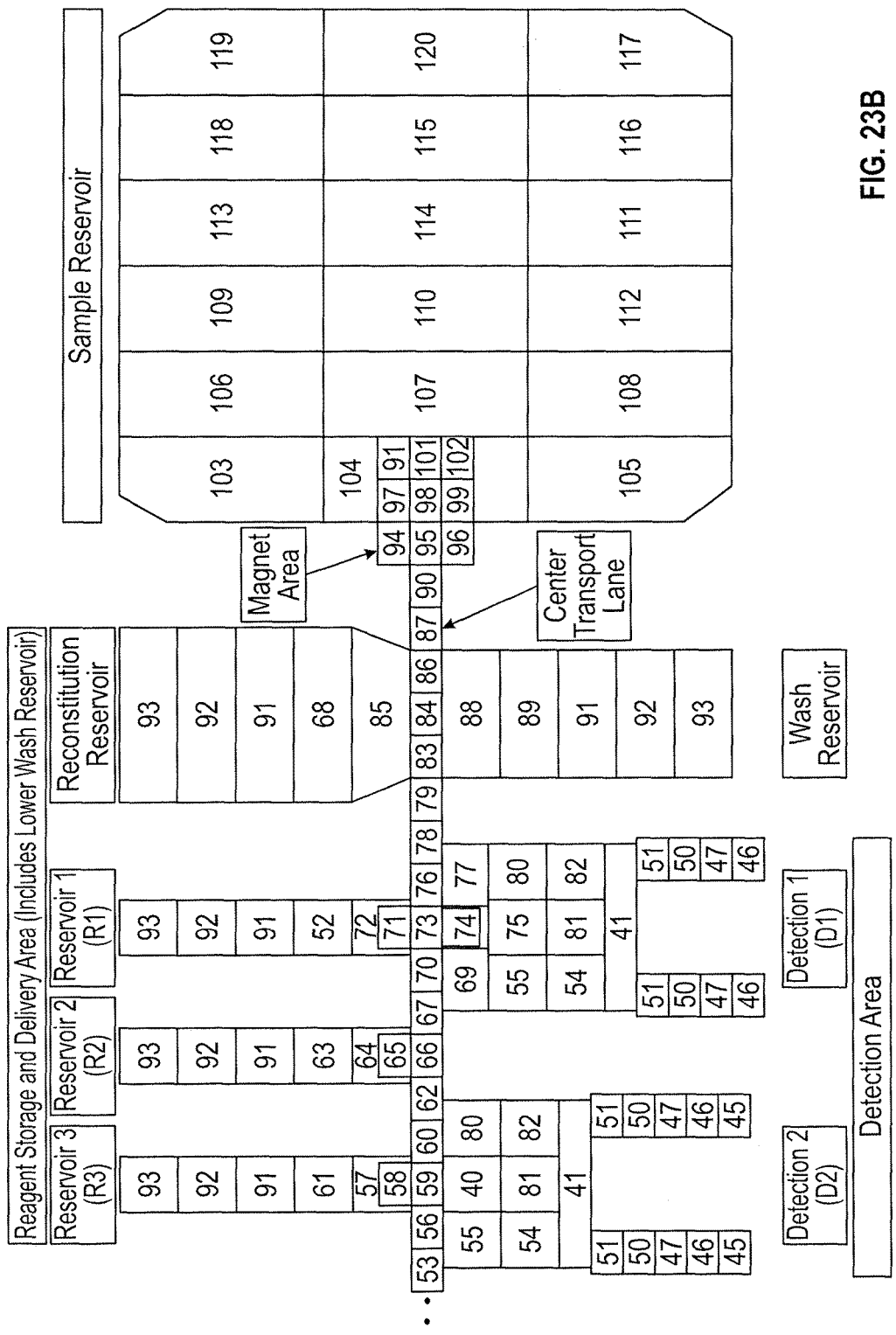
FIG. 23B schematically depicts another portion of an electrowetting grid of one configuration of the bottom substrate of the cartridge of the invention.

FIGS. 23A and 23B depict a general schematic of one configuration the bottom substrate of the cartridge of the invention. As shown in FIG. 23B, the substrate is divided into the sample reservoir, showing the larger pads of the electrowetting electrode grid that are used in sample preparation, based on the volume of the sample and the amount of lysis buffer, binding buffer and elution buffers needed for sample preparation. FIG. 23B also depicts a magnet area, where the capture beads are mixed with lysed sample (usually with the addition of binding buffer), washed, and eluted (using elution buffer). From there, in FIG. 23B, the droplets are loaded onto the Center Transport Lane, and moved into the reagent storage and delivery area. Moving through this area (as more fully described below), the droplet(s) move to the PCR reagent staging area shown in FIG. 23A, where they pick up the required reagents, primers, probes, enzymes, etc. for PCR. FIG. 23A depicts two amplification pad pathways and three heat zones for the PCR thermocycling. The droplets travel back and forth through these heat zones for an appropriate number of cycles, and then move back along the center transport lane to pick up detection reagents, signaling probes, etc., to be moved onto the detection electrode array. Also shown are a plurality of reservoirs, including the reconstitution reservoir (for use when the dried reagents are to be reconstituted by buffer and not by using the sample droplet to resuspend the reagents), a wash reservoir, and three additional reservoirs for the storage of buffers, etc. as needed.

Figure 24:
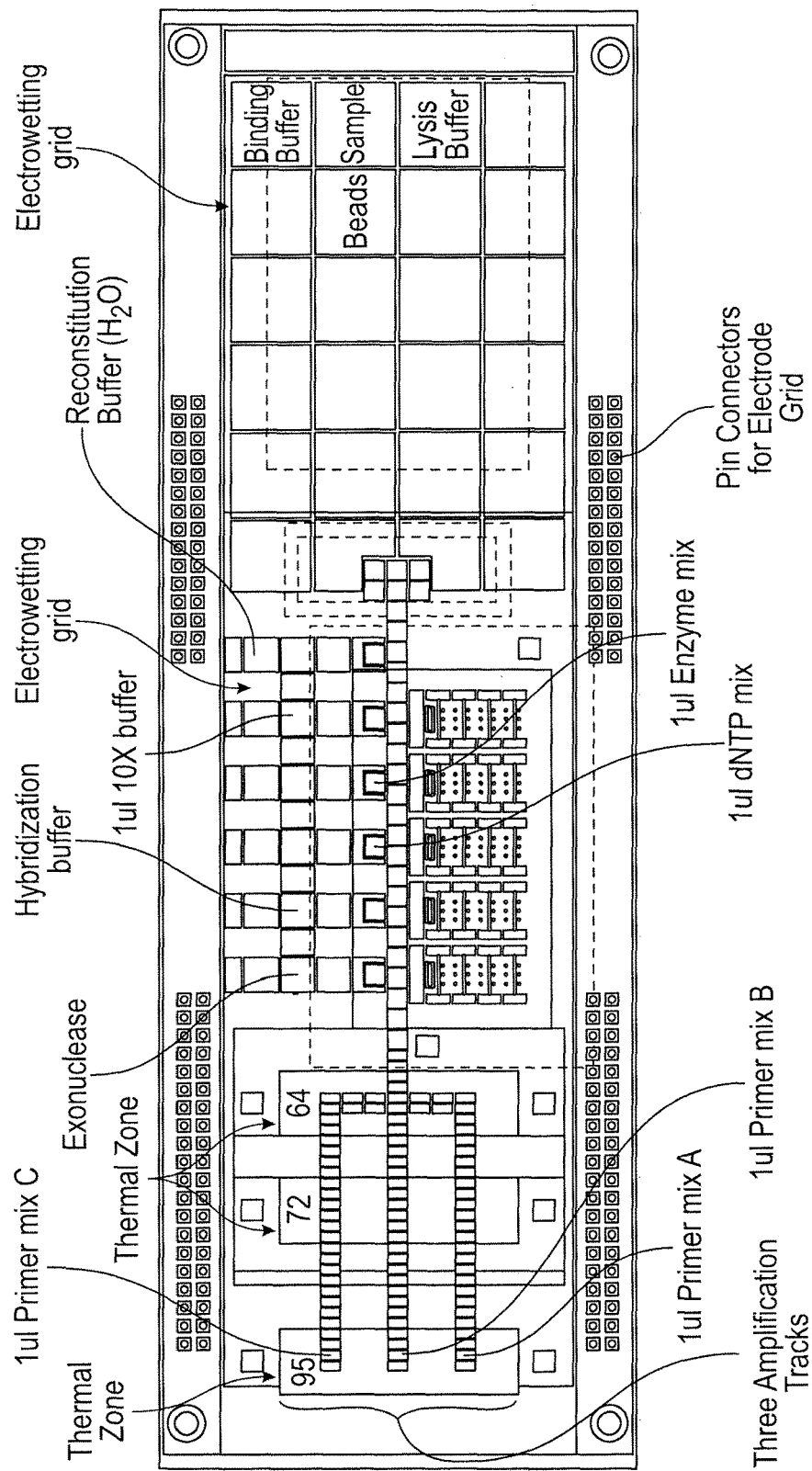
FIG. 24 is a top plan view of an embodiment of the bottom substrate showing the locations of optional dry reagents overlaid on a configuration of an electrowetting grid.

FIG. 24 shows the optional addition of dry reagents on the overlay of one general embodiment of the bottom substrate configuration. These can be used alone or in combination with liquid reagents as described herein, and the placement of either type of reagent should not be considered limiting. The bottom substrate of FIG. 24 depicts three amplification tracks, which as described herein can be used for three separate PCR reactions or for one reaction done along multiple pad pathways. The three amplification tracks are shown on the right, with three perpendicular thermal zones, depicted as 95C, 72C and 64C (although these can be adjusted based on the individual primer/probe PCR reactions as is well known in the art). The interconnects (herein shown as pin connectors) are at the edges of some sides of the substrate. The electrowetting electrode grid on the right are larger pads, allowing for sample handling, including lysis, capture bead mixing (in binding buffer), etc. The electrowetting grid on the left hand side contains smaller pads for smaller droplet size.

FIGS. 25A, 25B, 25C, 25D and 25E show a number of possible configurations of the electrowetting electrode grid, the dried reagent pad locations and the reagent pathways.

"XT-1" and "XT-2" refer to solutions comprising the appropriate label ligands (e.g. signal probes) for the detection of the analytes.

Bottom Substrate

The biochip cartridges of the present invention include a solid substrate containing a number of functionalities for use in the present invention. By "substrate" or "solid support" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, ceramics, mica, plastic (including acrylics, polystyrene and copolymers of styrene and other materials, polypropylene, polyethylene, polybutylene, polyimide, polycarbonate, polyurethanes, Teflon®, and derivatives thereof, etc.), GETEK (a blend of polypropylene oxide and fiberglass), etc., polysaccharides, nylon or nitrocellulose, resins, silica or silica-based materials including silicon and modified silicon, carbon, metals, inorganic glasses and a variety of other polymers, with printed circuit board (PCB) materials being particularly preferred. This substrate is referred to herein as a "bottom substrate", although as will be appreciated in the art, in some embodiments this substrate could be on "top" or the "side", relative to the ground.

The substrate is divided into a number of distinct functional areas or zones, which can be both spatially overlapping and spatially distinct, as outlined herein. As will be appreciated by those in the art, some of these zones, for example the sample preparation zone, may be optionally included or excluded depending on the assay and/or sample.

In general, as discussed above, the microfluidic platform used herein is based on the use of electrowetting techniques to form microdroplets that can be manipulated both spatially and biochemically as further described below.

Electrowetting techniques are the basis of the microfluidic cartridges herein. Electrowetting is the modification of the wetting properties of a hydrophobic surface (such as PCB) with an applied electric field. In an electrowetting system, the change in the substrate-electrolyte contact angle due to an applied potential difference results in the ability to move the electrolyte on the surface. Essentially, as described in U.S. Pat. No. 6,565,727 in the Summary of the Invention (hereby expressly and specifically incorporated by reference), by applying an electric potential to an electrode (or group of electrodes) adjacent to a droplet of polar liquid (e.g. one containing a target analyte), the surface on these electrodes becomes more hydrophilic and the droplet is pulled by the surface tension gradient to increase the area overlap with the charged electrodes. This causes the droplet to spread on the surface, and by subsequently removing the potential, or activating different electrodes, the substrate returns to a hydrophobic state, resulting in the droplet moving to a new hydrophilic area on the substrate. In this way, the droplets can be physically and discretely moved on the planar surface of the substrate to different zones, for processing, handling and detection. The droplets can be moved at varied speeds, split (e.g. a single droplet can be split into two or more droplets), pulsed and/or mixed (two or more droplets merged onto the same location and then either split or moved as one). In addition, electrowetting can instigate mixing within a single droplet. As described in more detail below, droplets can also be used to rehydrate dry reagents stored at different locations on the PCB substrate. A key advantage of electrowetting is precise manipulation of very small volumes. For example, isolated target nucleic acid can be eluted at a very high concentration in less than 10 μl prior to PCR amplification, compared to 100 μl elution volumes and much lower target analyte concentrations featured in other systems. In addition, electrowetting allows altering fluid paths in development and in the product via software, without the need to make any changes to the physical interface (e.g., new valves, fluid paths, etc.).

Microfluidic systems utilizing these techniques have been pioneered by Advanced Liquid Logic, and are described in U.S. Patent Pub. Nos. 2013/0252262, 2013/0233712, 2013/0233425, 2013/0230875, 2013/0225452, 2013/0225450, 2013/0217113, 2013/0217103, 2013/0203606, 2013/0178968, 2013/0178374, 2013/0164742, 2013/0146461, 2013/0130936, 2013/0118901, 2013/0059366, 2013/0018611, 2013/0017544, 2012/0261264, 2012/0165238, 2012/0132528, 2012/0044299, 2012/0018306, 2011/0311980, 2011/0303542, 2011/0209998, 2011/0203930, 2011/0186433, 2011/0180571, 2011/0114490, 2011/0104816, 2011/0104747, 2011/0104725, 2011/0097763, 2011/0091989, 2011/0086377, 2011/0076692, 2010/0323405, 2010/0307917, 2010/0291578, 2010/0282608, 2010/0279374, 2010/0270156, 2010/0236929, 2010/0236928, 2010/0206094, 2010/0194408, 2010/0190263, 2010/0130369, 2010/0120130, 2010/0116640, 2010/0087012, 2010/0068764, 2010/0048410, 2010/0032293, 2010/0025250, 2009/0304944, 2009/0263834, 2009/0155902, 2008/0274513, 2008/0230386, 2007/0275415, 2007/0242105, 2007/0241068, U.S. Pat. Nos. 8,541,176, 8,492,168, 8,481,125, 8,470,606, 8,460,528, 8,454,905, 8,440,392, 8,426,213, 8,394,641, 8,389,297, 8,388,909, 8,364,315, 8,349,276, 8,317,990, 8,313,895, 8,313,698, 8,304,253, 8,268,246, 8,208,146, 8,202,686, 8,137,917, 8,093,062, 8,088,578, 8,048,628, 8,041,463, 8,007,739, 7,998,436, 7,943,030, 7,939,021, 7,919,330, 7,901,947, 7,851,184, 7,822,510, 7,816,121, 7,815,871, 7,763,471, 7,727,723, 7,439,014, 7,255,780, 6,773,566, and 6,565,727, all of which are incorporated by reference in their entirety for the Figures and Legends and accompanying description associated with electrowetting configurations, techniques and formation of electrowetting grids.

Thus, the substrates of the invention contain a grid of electrodes such that discrete processing zones are created, including pathways or routes for the droplets as appropriate for the assays being run. In general, a "spot" or "location" or "pad" (sometimes referred to as an "electrowetting pad" or (EWP")) is generally depicted in the present figures and those of the incorporated ALL patents as a square surrounded by electrodes, such that a droplet moves along a path in discrete steps, from pad to pad, similar to game pieces on a game board. By manipulating the electronic grid, the droplets can move in four directions as needed, forward (north), backward (south), left (west) and right (east), relative to a starting position.

Figure 25A:
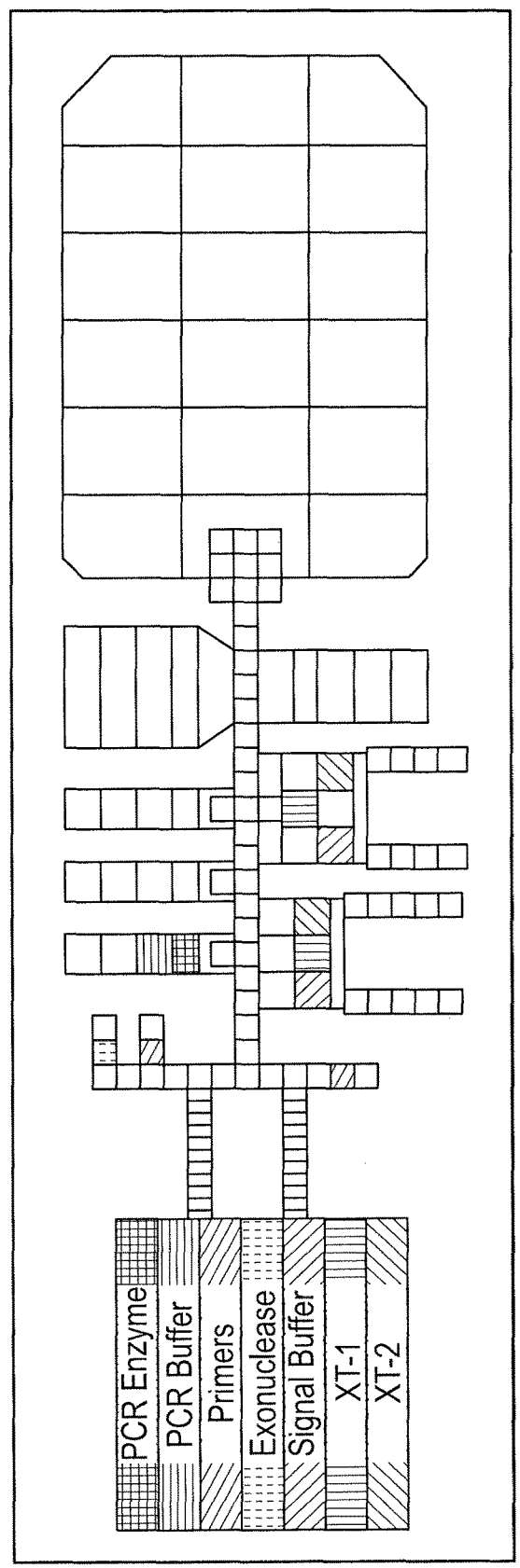
FIGS. 25A, 25B, 25C, 25D and 25E show a number of possible configurations of the electrowetting electrode grid, the dried reagent pad locations and the reagent pathways.
Figure 25B:
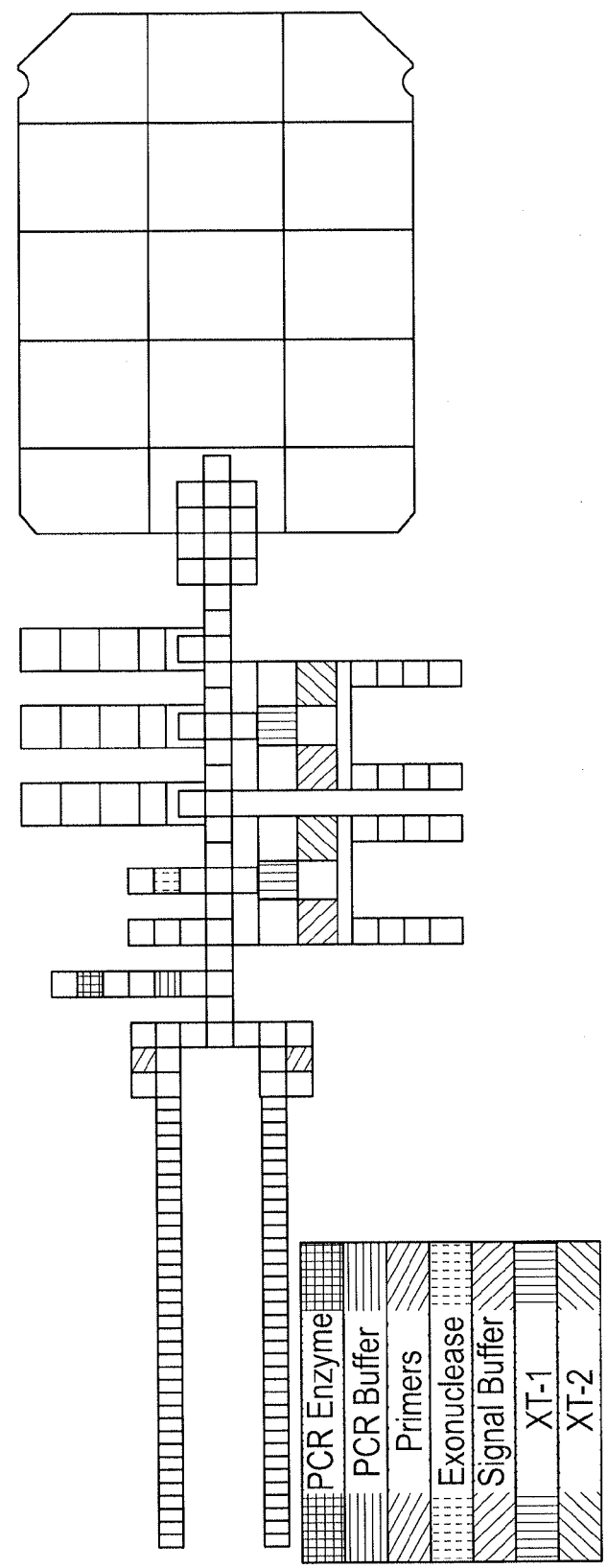
Figure 25C:
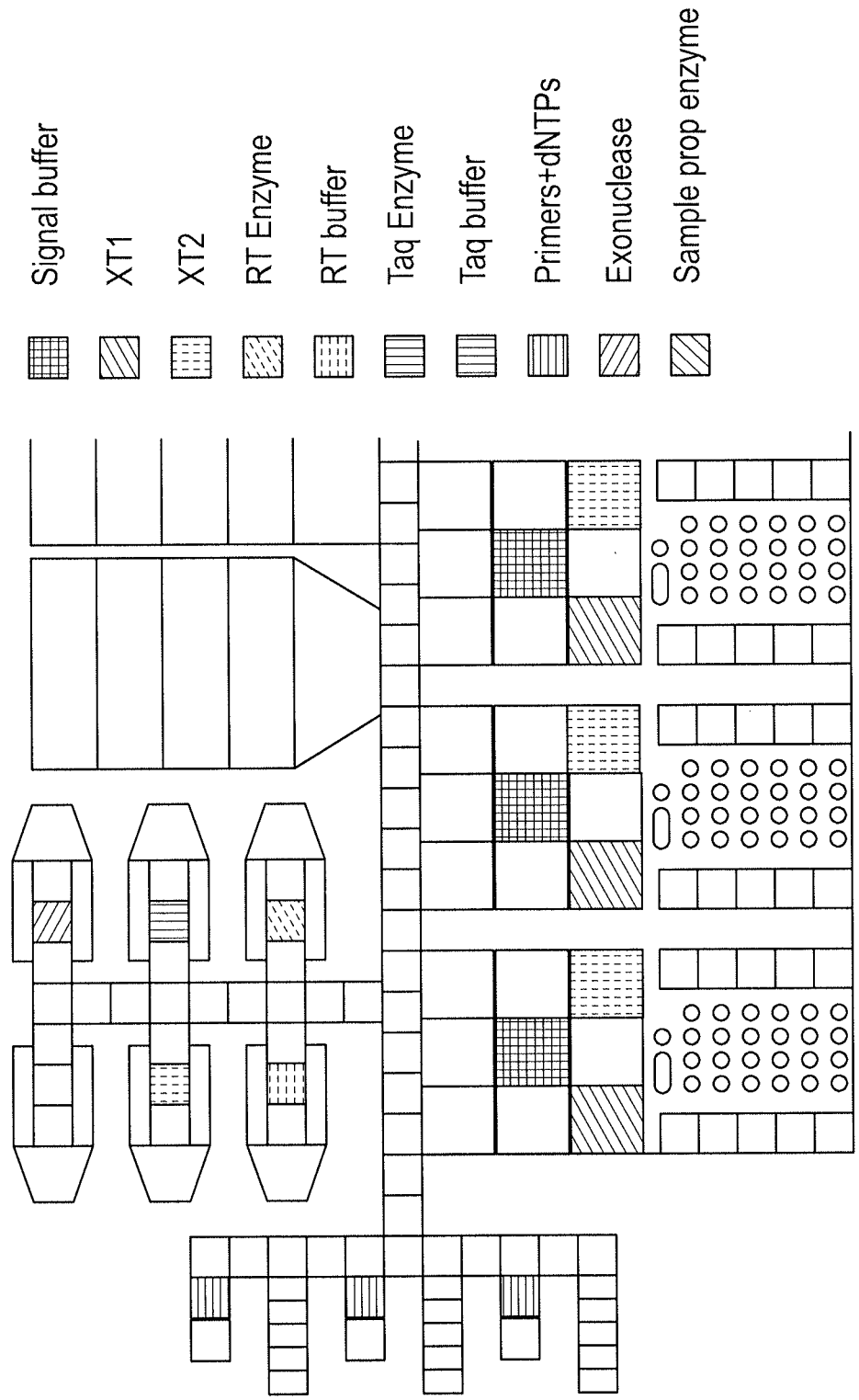
Figure 25D:
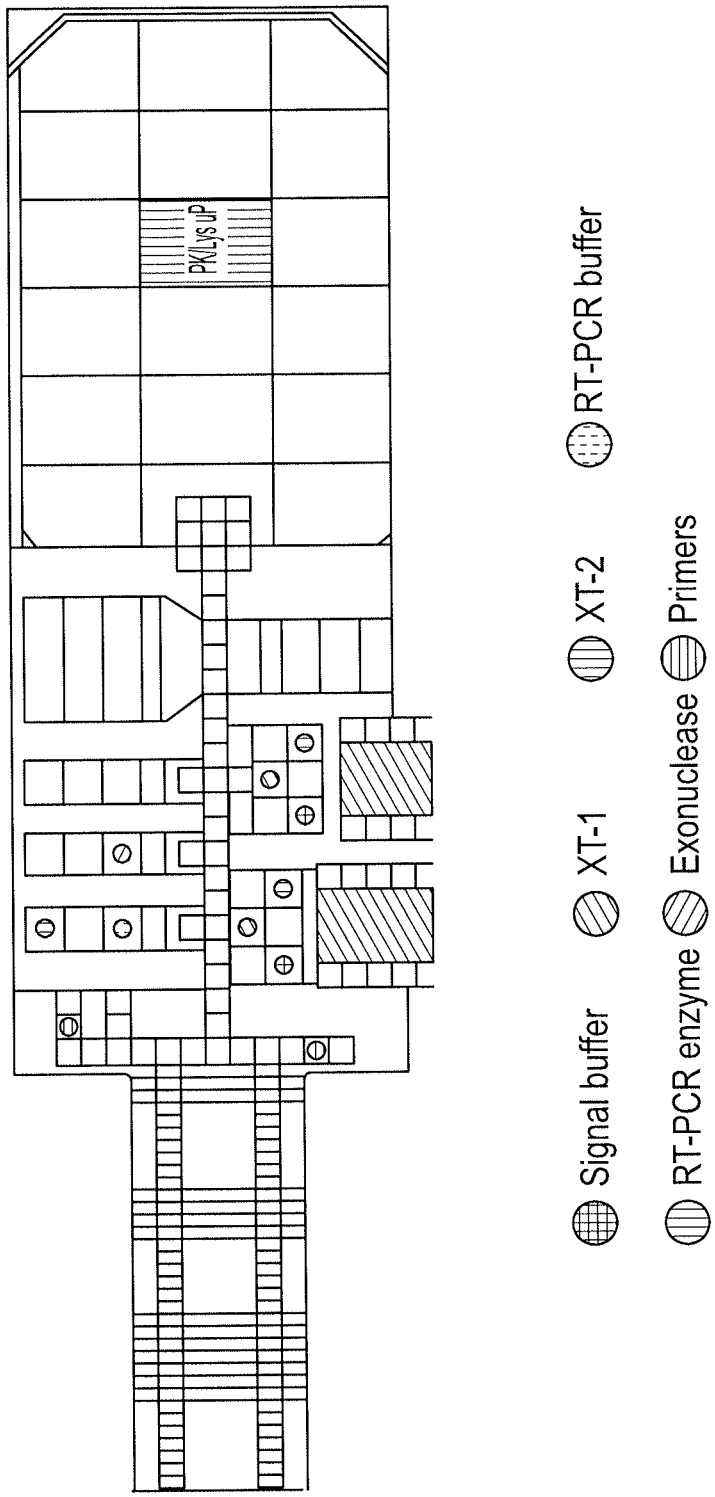
Figure 25E:
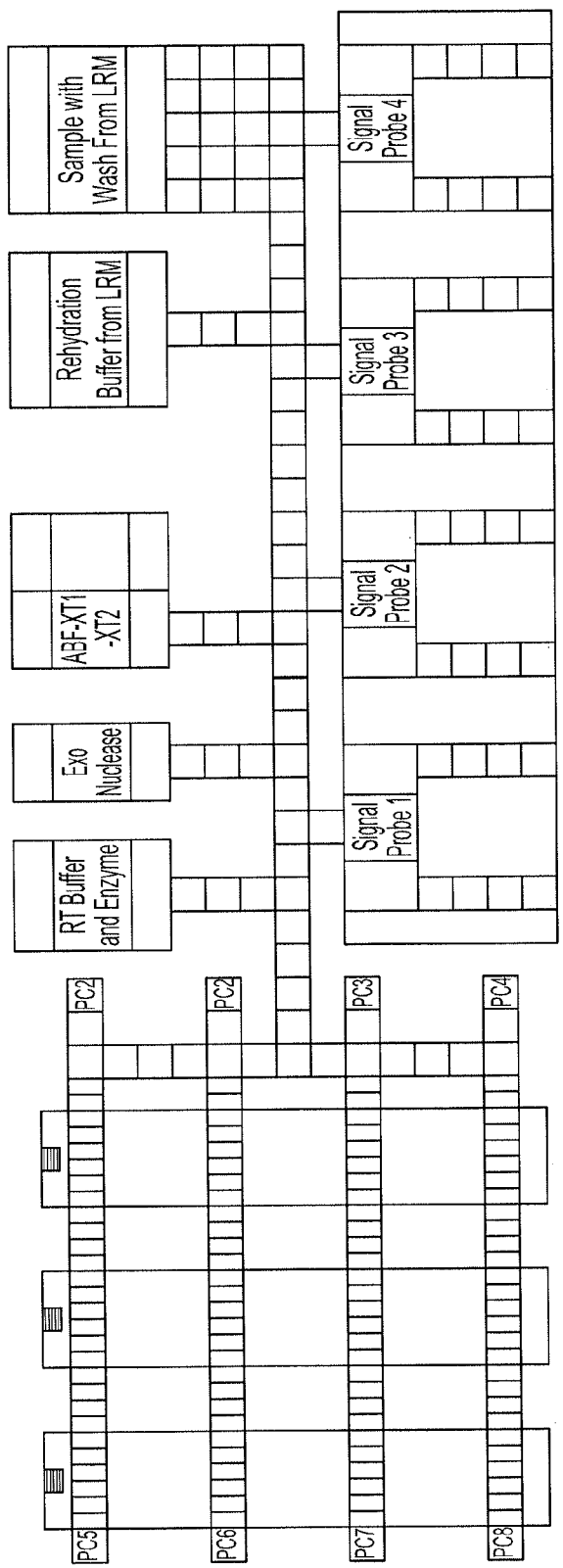

As will be appreciated by those in the art, there are a wide number of electrode grid configurations that can be used to generate the multiplex cartridges of the present invention. Exemplary of an embodiment of particular use are FIGS. 21-22, which depict a system a system with a three track amplification pathway and 5 detection subarrays in the detection zone. FIG. 25B depicts a similar embodiment with a two track amplification pathway. In some alternative embodiments, a four or five track amplification pathway can be employed. As noted above, each amplification track can accommodate more than one droplet (e.g., 2, 3 or more), resulting in enhanced multiplexing. In particularly preferred embodiments, three or four tracks will handle six to eight different amplification reactions (two droplets per track).

However, there are a wide variety of other useful configurations for different utilities. For example the Figures of U.S. Pat. No. 8,541,176 shows a variety of ways the electrowetting electrode grid and top plates can be arranged to allow movement of samples (depicted as "slugs") past a location that contains magnetic beads for example.

Thus, the bottom substrate contains a grid of etched electrodes forming a network of pads for moving sample droplets from sample preparation through detection of target analytes.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane, "edge card connectors") or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

In one embodiment, as depicted in the Figures, the connections from both the electrowetting electrode grids and the detection electrodes, described below, are made by passing through the substrate to produce a so called land grid array that can interface to a pogo pin or like connector to make connections from the chip to the instrument.

In some embodiments, the surface of the bottom substrate (e.g. the PCB with the electrode grids) is coated with a film of chemical functionality to facilitate the electrowetting mechanism and clean transport from pad to pad. In a particularly useful embodiment, the surface is coated with a polyimide film such as KAPTON® from DuPont (e.g., black or yellow Kapton®), which forms a dielectric layer. The surface properties of the dielectric layer are important to facilitate electrowetting and to attenuate the voltage being used in order to prevent electrolysis in the aqueous droplet. In addition, the Kapton® or similar surface such as a solder mask must be coated with a hydrophobic coating to render the surface hydrophobic, which is required for electrowetting to function.

Sample Preparation Zone

Sample preparation is a key component of a "sample to answer" system, to reduce exposure of lab technicians to biological materials, particular those containing pathogens, as well as avoiding the use of highly trained lab personnel. In general, the cartridges of the invention are designed to receive either liquid or solid samples.

The sample is loaded through a sample entry port in the housing, which ports down onto the bottom substrate (as will be appreciated by those in the art, this is through the top plate, and, depending on the configuration of the LRM, through this layer as well). Once loaded, the sample entry port is then sealed, for example with a hinge top as shown in the figures. In some embodiments, the sealing mechanism includes a clip, lock or tab that, once closed, will permanently prevent accidental reopening without compromising the integrity of the cartridge. In other embodiments, the cap can be re-opened, allowing shipment of the cap in the closed state and subsequent opening by the operator. Once loaded and sealed, the cartridge is inserted into the apparatus and all subsequent steps are done in the assay run in a completely contained system that does not require additional user handling.

Liquid samples are generally blood, serum, plasma, urine, saliva, cerebral spinal fluid, lymph, perspiration, semen or epithelial samples such as cheek, nasopharyngeal, anal or vaginal swabs to which lysis buffer has been added to resuspend the cells. Solid samples, such as feces or tissue samples (e.g. tumor biopsies) generally need to be resuspended and diluted in a buffer, e.g., the Cary Blair medium. Some organisms, such as viruses and most bacteria, can be lysed chemically by the addition of a lysis buffer with or without elevated temperature or proteolytic enzymes. Some organisms are difficult to lyse by chemical and/or enzymatic methods and require mechanical disruption or shearing of the cell membranes. As such, an optional component of the sample preparation zone is an impeller component, wherein the solid sample is added to the impeller component, buffer added (for example, lysis buffer) and the impeller activated to grind or break up the solid sample such that individual cells are more accessible to lysis buffer such that more target analytes are released. The impeller imparts turbulent action to the fluid, wherein beads are contained. The primary lysis action is due to bead collisions with target organisms, which are thereby lysed, breaking them open and exposing the target nucleic acids. The presence of the lysis buffer inhibits the DNases or RNases which may destroy the RNA or DNA targets once the cells are disrupted. The impeller is like a paddle wheel that rotates very fast.

In some embodiments, rather than lysis buffer being added as a liquid, lysis reagents can be dried onto certain pads as is generally described below for other assay reagents.

Thus, the sample preparation zone optionally includes an impeller component and/or paddle mixer. The paddle mixer can be used to mix the sample with resuspension buffer without lysing the cells prior to addition of the lysis buffer. The sample is loaded into the sample entry port, mixed with lysis buffer in either a paddle mixer or an impeller, resulting in high levels of sample cells being lysed.

Once the cells are lysed, it is desirable to do at least a crude purification, to remove other cellular and sample debris from the sample to facilitate the downstream handling and processing. Research samples in buffer do not necessarily require purification, but even there purification is typically performed. A well-known technique relies on the use of capture beads, which capture the desired target analytes away from the cellular and sample debris. Thus, the sample preparation zone optionally includes sample capture beads to facilitate this first purification of the desired target with fluid access to binding buffer, used in conjunction with the capture beads. In this embodiment, capture beads and binding buffer are mixed with the sample in lysis buffer after the cells or viruses are disrupted by mechanical and/or chemical means. In general, the capture beads are magnetic to facilitate handling, although as will be appreciated by those in the art, other systems may use non-magnetic beads, such as polystyrene or silica beads (for example, beads may be captured in a zone by size or on an affinity column).

The capture beads are coated with a functionality that facilitates capture of the target analytes. For example, for the capture of nucleic acids, the beads can be coated with a negatively charged coating to facilitate the adsorption of positively charged nucleic acids to the surface, which are then washed with buffer, optionally transported on the substrate and then treated with elution buffer to remove the purified nucleic acids for further handling. As will be appreciated by those in the art, there are a number of commercially available bead systems, such as MagaZorb® Beads from Promega, MagMax from Life Tech, or beads from Qiagen, MoBio, BioRad, etc.

Alternatively, capture beads may be functionalized with capture nucleic acid probes in order to either specifically or non-specifically pull out nucleic acids. For example, the beads may be functionalized with random 6-mers, to generally pull out nucleic acids, or with capture probes specific to the desired target nucleic acids. In some cases, for example when mRNA is the target, beads coated with poly-T capture probes can be used.

As described below, the beads with the captured target analytes are generally mixed and washed prior to elution of the target analytes from the beads to begin the assay process. As part of this process, beads bound with the target analytes are manipulated using magnets and electrowetting to remove residual fluids and/or amplification inhibitors prior to target elution.

Reagent Zone

Once the target analytes have been eluted and thus released from the beads, the sample containing the target analytes is then ready for amplification (in the case of nucleic acid assays, or other reactions as necessary for other analytes such as proteins).

Droplets of sample are dispensed into the reagent zone, which optionally have dry or solid reagents at specific locations on the grid. No particular dispenser structure is required in this step, as the elution volume is split into a desired number of droplets using electrowetting. For instance, if the elution volume is 6 µl and each PCR reaction requires a 1 µl droplet, then three 1 µl droplets can be "pinched off" in a consecutive fashion. As will be appreciated by those in the art, the form of the reagent will depend on the reagent. Some reagents can be dried or in solid form (for example when particular buffers are to be used), others can be lyophilized, etc. Particularly useful embodiments utilize dried reagents with added stabilizers, such as salts, sugars, polysaccharides, polymers or proteins such as gelatins, etc. as will be appreciated by those in the art. For example, Biomatrica produces commercial stabilizers for use in the present system.

As will be appreciated by those in the art, if used, the dried reagents can be rehydrated in one of two general ways. Either liquid from the LRM is introduced at the appropriate pad or the sample itself serves as an aqueous solvent to put the solid reagents into solution. For example, the appropriate resuspension buffer (which can be water, in some cases) can be added through the top plate from the LRM to a particular pad to rehydrate the reagent(s), and then the reagent droplet can be merged with the sample droplet. Alternatively, the droplets containing the target analyte (for example, in elution buffer used to liberate the target analytes from the capture beads) may be transported to a pad containing the dried reagent(s), which are then suspended in the droplet itself. One benefit of this embodiment is that the ultimate volume of a droplet does not increase significantly, as it does when a droplet of reagent is merged with a droplet of sample. This may be particularly useful in situations where multiple reagent additions are required.

As shown in the Figures, a number of embodiments for nucleic acid amplification and detection include a plurality of pads containing dried reagents. See for example FIGS. 24 and 25A-E.

The number, type and quantity of the different reagents will depend on sample, the target analyte and the desired reaction. For example, for nucleic acid target sequences in a standard PCR reaction, when the starting sample is DNA, the on-board dried reagents include RT-PCR buffer, PCR enzyme (e.g. a Taq polymerase), dNTPs, PCR primers, exonuclease, signal probes, signal buffer and detection buffers (with the lysis buffer, the binding buffer, the elution buffer, the (optional) reconstitution buffer(s), and magnetic bead suspension all being contained in the LRM rather than dried on the substrate). Several specific embodiments are outlined below. However, as will be appreciated by those in the art, any number of configurations of dried reagents and liquid reagents in the LRM can be used.

The chamber formed from the "bottom" substrate and the top plate, more fully described below, is generally filled with a fluid in which the target analyte droplets (usually aqueous solutions) are immiscible, and this immiscible fluid is generally less polar than the solution of the droplet. As described in U.S. Pat. No. 8,541,177, columns 60-63, there are two general ways of isolating droplets on pads including filling the chamber with an immiscible fluid including immiscible liquids and immiscible gases, or by using the immiscible liquid as a droplet encapsulant, for example giving the droplet a shell of oil by passing the droplet through an air/oil interface, with the former generally being preferred.

Particularly suitable immiscible fluids for use in the nucleic acid detection assays described herein include, but are not limited to, silicone oils, mineral oil, fluorosilicone oils; hydrocarbons, including for example, alkanes, such as decane, undecane, dodecane, tridecane, tetradecane, pentadecane, hexadecane; aliphatic and aromatic alkanes such as dodecane, hexadecane, and cyclohexane, hydrocarbon oils, mineral oils, paraffin oils; halogenated oils, such as fluorocarbons and perfluorocarbons (e.g. 3M Fluorinert liquids) as well as mixtures of the above. Examples of suitable gas filler fluids include, without limitation, air, argon, nitrogen, carbon dioxide, oxygen, humidified air, any inert gases. In one embodiment, the primary phase is an aqueous solution, and the secondary phase is air or oil, which is relatively immiscible with water. In another embodiment, the filler fluid includes a gas that fills the space between the plates surrounding the droplets. A preferred filler fluid is low-viscosity oil, such as silicone oil. Other suitable fluids are described in U.S. Patent Application No. 60/736,399, entitled "Filler Fluids for Droplet-Based Microfluidics" filed on Nov. 14, 2005, the entire disclosure of which is incorporated herein by reference. The fluid may be selected to prevent any significant evaporation of the droplets.

Sample Manipulation Zone

As will be understood by those in the art, the movement of droplets from pad to pad, with the addition of reagents as needed, can be used for any number of sample manipulations. In the case of the nucleic acid manipulations for nucleic acid detection, these manipulations generally include the addition of reagents such as PCR enzymes, PCR buffer, primers, exonuclease, reverse transcriptase (RT) enzymes, RT-PCR buffers, signal buffers, signal probes, etc.

In one embodiment, on-chip thermal components, e.g. resistive heaters for PCR thermocycling, are used. In this embodiment, resistive heater(s) can be placed underneath the electrode grid pathway of pads to result in thermal zones for amplification, exonuclease digestion, reverse transcription, target elution, and the electrochemical detection. As will be appreciated by those in the art, some manipulations such as PCR amplification requires from 2 to 3 different temperatures (primer binding, extension and denaturation), while others require a uniform temperature for best results, e.g. enzymatic processes such as the use of exonuclease and reverse transcriptase, specific temperature(s) for improved elution and/or reagent resuspension, or binding/assay temperatures in the case of the electrochemical detection. Isothermal amplification techniques and other PCR alternatives typically require precise temperature control.

Alternatively, these thermal components such as heaters are found off-chip in the bays of the instrument into which the cartridge is placed.

In one embodiment, the sample manipulation zones on the substrate can optionally include sensors, for example to monitor and control thermal zone temperatures, particularly in the case where specific temperatures are desirable. These sensors can include, but are not limited to, thermocouples and resistance temperature detectors (RTDs). Again, for many embodiments, as for the thermal elements, these can also be "off chip" in the bays.

Amplification Zone

As shown in the figures, in the embodiments for detecting nucleic acid targets, the substrate comprises one or more amplification pathways. As shown in a number of the figures, a bottom substrate can contain 1, 2, 3 or more amplification pathways of pads. These can be used for individual PCR reactions (e.g. one droplet is moved up one path and down another, etc.) or for multiplexing (e.g. for three pathways, three different droplets can be moved up and down a single pathway).

As will be appreciated by those in the art, each PCR reaction can additionally be multiplexed. That is, for target specific amplification, the use of multiple primer sets in a single PCR reaction can be unwieldy, and thus the present invention allows multiple reactions to achieve higher levels of multiplexing. For example, for the evaluation of 21 different target sequences (for example, in screening of respiratory viruses), it may be desirable to run 3 different reactions of seven primer sets; e.g. a first PCR sample droplet (e.g. the bottom pathway) picks up a first set of 7 primer pairs (e.g. "Primer Mix A"), a second droplet picks up a second set of 7 primer pairs ("Primer Mix B"), and a third droplet picks up a third set ("Primer Mix C"). In some embodiments, the primers will be completely different in each set; in others, redundancy and/or internal controls are built into the system by adding the same primer sets to different tracks. The multiplexing flexibility represents one of the key advantageous and distinguishing features of the present invention. The number of multiplexes can vary easily through software without the need to modify any physical components of the system. Traditional channel based microfluidic devices lack such flexibility.

In general, the amplification reactions (as more fully described below) for use in the present systems use sets of primers wherein one primer of each set has a blocked end that is impervious to standard exonucleases. That is, it is desirable to remove one strand of the double stranded amplicons that are generated in the PCR reaction, so as to simplify the detection reactions and remove background signal. Thus, by running a first PCR reaction and then adding exonuclease, one strand of the double stranded amplicon is digested, leaving only the detection strand.

Figure 34:
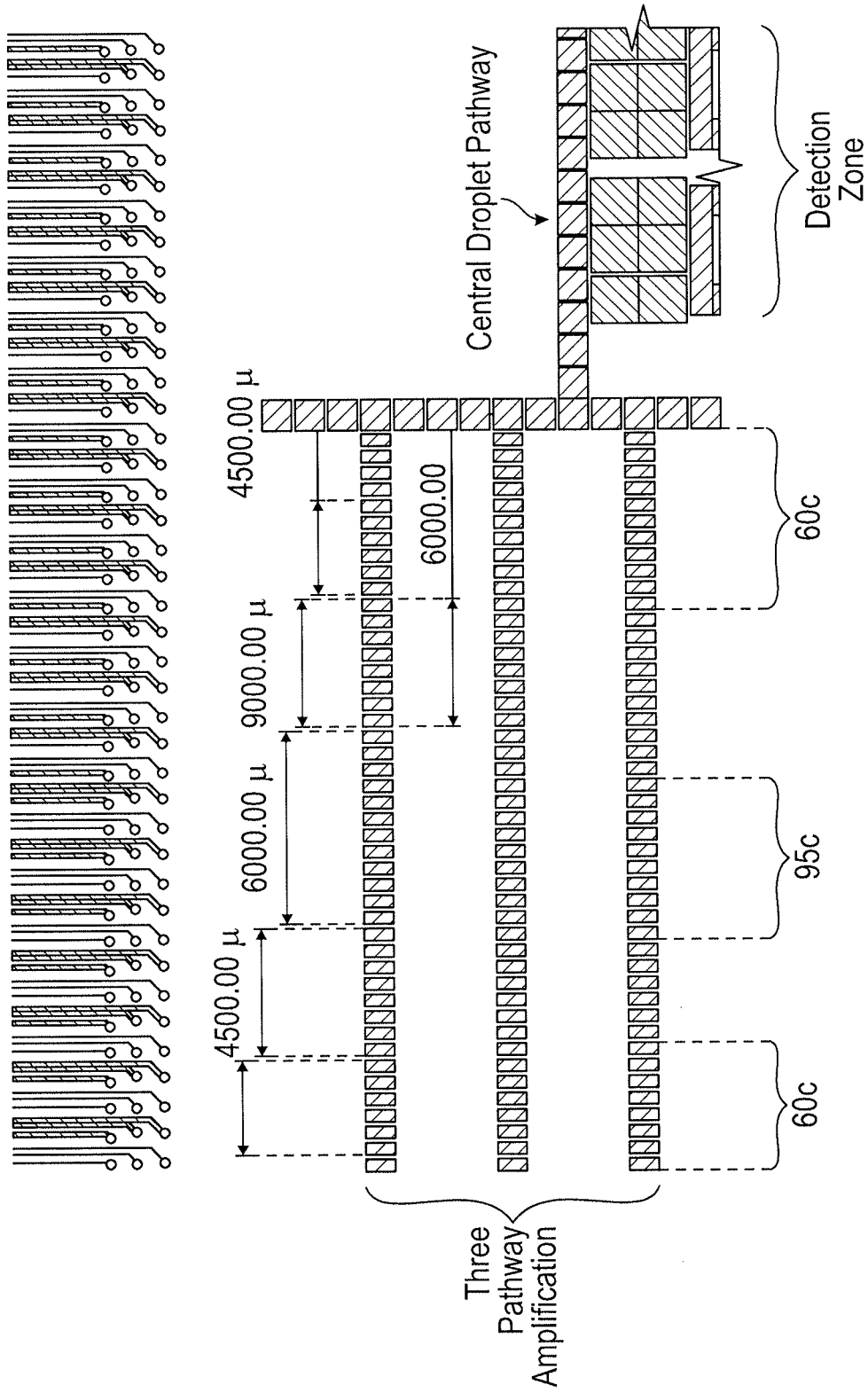
FIG. 34 depicts a schematic a three pathway amplification zone for use in "tandem amplification".

The use of heating zones perpendicular to the amplification pathway, as generally depicted in FIG. 23A, allows the droplets to travel through the appropriate thermal zones. As shown in FIG. 24, three amplification pathways are shown with three perpendicular thermal zones (in this case, the thermal elements are off chip Peltier heaters and show desired temperatures of 95 C, 72 C and 64 C for use in PCR thermocycling). In some embodiments, two different temperature zones (e.g., about 95 C for denaturation and about 60 C for annealing and extension) can be used for a two-step PCR reaction. In other embodiments, a three-zone, two-temperature configuration may be employed, wherein a middle heater controls the denaturation temperature (e.g., about 95 C), and additional heaters on each side of the denaturation heater provide substantially the same annealing and extension temperature (e.g., about 60 C) as shown in FIG. 34. In this configuration, two-step amplification cycles can be performed with more than one droplet in each PCR track, sometimes referred to herein as "tandem amplification" or "typewriter amplification". For example, two droplets may be positioned in each PCR track and spaced in such a way that when one droplet is in the denaturation zone, the other is in one of combined annealing and extension zones, and vice versa. By shuttling the droplets in tandem back and forth between the denaturation and annealing/extension zones, one can amplify both of them in the same amount of time it would normally take to amplify a single droplet. In a three-track PCR configuration, this means that six droplet can be amplified simultaneously instead of three.

Detection Zones

The biochips of the present invention rely on the use of electrodes and electrochemical labels for the detection of target analytes. Generally, the electrode surface (optionally coated with a self-assembled monolayer (SAM), as outlined below) has capture ligands which bind the target. A second label ligand, which also binds to the target, is included, such that in the presence of the target, the label ligand is bound near the surface of the electrode, and can be detected electronically.

Thus, the detection zone of the bottom substrate comprises one or more separate arrays of detection electrodes. By "electrode" herein is meant a composition, which, when connected to an electronic device, is able to sense a current or charge and convert it to a signal. Alternatively an electrode can be defined as a composition which can apply a potential to and/or pass electrons to or from species in the solution. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred. In a particularly useful embodiment, both the electrowetting electrode grid and the detection electrodes are gold, and are fabricated simultaneously on the PCB.

The present system finds particular utility in array formats, i.e. wherein there is a matrix of addressable detection electrodes (herein generally referred to "pads", "addresses" or "micro-locations"). By "array" herein is meant a plurality of capture ligands on electrodes in an array format; the size of the array will depend on the composition and end use of the array. Arrays containing from about 2 different capture ligands to about 50 to 100 can be made. In some preferred embodiments, 80 or 100 working detection electrodes are split into four or five distinct zones of 20, with each zone having up to 60 capture probes (three different capture probes per electrode).

The detection zone of the substrate comprises one or more arrays of electrodes that is in fluid communication with the droplet pathway. That is, the droplets containing the amplicons will pick up necessary detection reagents such as label probes and then be dispersed on the detection zone. In general, each detection zone receives one or more sample droplets which are generally dispersed on the array of electrodes, which is considered one larger "pad".

Each detection electrode comprises an independent lead (interconnect) to transmit input and electronic response signals for each electrode of the array. In contrast to previous systems which require the ability to independently alter only input signals to each electrode but not electronic response signals, it is important in the present invention that both input and electronic response signals be independently monitorable for each electrode; that is, each electrode is independently addressable.

Additional Components

In addition to the components of the bottom substrate described above, the bottom substrate can also optionally comprise an EPROM, EEPROM or RFID to identify the cartridge, for example containing information about the batch, treatment or contents of the biochip. This can include information about the identification of the assay, for example.

Top Plate

The bottom substrate, described above, together with a top plate form a chamber or chambers for the reactions and processing described herein. In most embodiments, the top plate is substantially parallel to the bottom plate, to form a reaction chamber of uniform depth. In some embodiments the top plate may be optionally slanted, for example to drive air bubbles to the highest point of the chamber to avoid interference with the reactions on the surface or for access to an air vent as discussed herein. As outlined herein, and as will be appreciated by those in the art, the top plate can take on a number of configurations and can be made of a variety of materials. Suitable materials include, but are not limited to, fiberglass, Teflon®, ceramics, glass, silicon, mica, plastic (including acrylics, polystyrene and copolymers of styrene and other materials, polypropylene, polyethylene, polybutylene, polycarbonate, polyurethanes, Teflon®, and derivatives thereof, etc.), etc. A particularly preferred top plate material is polycarbonate.

In one embodiment, the top plate and bottom substrate mated together form a single chamber that is filled with the immiscible fluid and through which the droplets are moved, merged, split, etc. Generally, this is accomplished by three dimensional ridges formed on the top plate to form the sides of the chamber(s). In alternate embodiments, the top plate and the bottom substrate can be separated into more than one chamber as needed. For example, the top plate can define two chambers, one for general sample handling and purification, and a second chamber, connected through a fluid passageway in the top plate, for the reagent loading, amplification reactions and detection. This approach could be valuable for keeping different parts of the reaction separated. In addition, top plate design can include varied gap heights to allow for expected fluid volumes within different areas of the cartridge, i.e. higher gap heights where a larger volume of fluid is present (e.g. over the sample handling zone) and lower gap heights where smaller volumes of fluid are present (e.g. over the amplification and/or detection zones).

The top plate generally includes a seal to confine liquids (and particularly any biological samples) to the chamber(s). This can also be used to mate the top and bottom plates together, and can include gaskets (e.g. silicone, rubber, etc.), adhesives and glues, etc. The seal comprises an epoxy polymer that is curable by ultraviolet (UV) light. The present inventors discovered that plasma treatment of the PCB helps to improve the sealing and reduce leakage of the immiscible liquid from the chamber.

The top plate is designed with a plurality of entry ports to the bottom substrate that define delivery locations for sample, reagents, and the immiscible fluids (e.g. oil(s)). These entry ports, also referred to herein as "fluid passages", "fluid passageways" or "fluid ports" are in fluid connection with the pads which they serve. That is, whether abutting or remote, two elements will have a fluid passageway between them; in some cases this is the droplet pathway of the electrowetting grid, while in others it is a fluidic channel between two components of the system. In many embodiments, these entry ports are perpendicular to the bottom substrate, allowing the fluids to flow downward onto the pads (via either gravity or the pressure used for the blister pack delivery discussed below). This can be referred to as a type of "one-to-one spatial correspondence". Alternatively, some ports may be channels within the top plate such that delivery of the fluid can occur remotely, e.g. at a location distant from the actual reagent storage blister, such that the blister exit port is connected to a fluid channel whose exit vents at the desired corresponding pad location for delivery of the fluid (that is, the blister volume (once ruptured) and the pad are in "fluid communication").

In optional embodiments, passive one way valves can be used to prevent backflow.

In addition, the top plate may optionally include one or more vents to reduce air bubble formation and/or remove any air bubbles that do form. In some embodiments featuring three heater zones, the vents can span a distance from the outermost 95 C denaturation heater to the middle heater, with an individual vent for each amplification track. However, those skilled in the art that positioning of the vents is flexible and will depend on the particular layout of the amplification zone.

In some embodiments, all or part of the top plate can be coated with a hydrophilic, oleophobic material to absorb excess aqueous reagents while excluding oil, such that the oil in the chamber stays evenly distributed through the chamber(s). In some embodiments, this hydrophilic and oleophobic material prevents oil from flowing into select regions but allows passage of aqueous fluids and air, for example surrounding the entry ports, such that oil is prevented from venting up through the entry ports.

While in most cases, the top and bottom plates are electronically insulated from each other, in some optional embodiments, materials, such as one or more conductive sponges, can be used to electrically connect the top plate to the bottom PCB substrate.

The contacts between the bottom and top plates are generally bonded together with an oil and temperature resistant adhesive as is generally known in the art. That is, the bottom surface of all or part of the top plate is bonded with the edges and dividers of the PCB bottom plate. Similarly an adhesive on the top surface of the top plate is used to bond the top plate with the LRM.

Liquid Reagent Modules

In addition to the bottom substrate and the top plate, the cartridges of the invention additionally comprise a liquid reagent module (LRM) for the delivery of liquid reagents to the reaction chamber(s) of the cartridge. This fits on top of the top plate for delivery down through the entry ports in the top plate to deliver fluids to the bottom substrate, with the housing covering some or all of these three layers. As is generally described herein, the present systems rely on a combination of dried reagents on the bottom substrate combined with liquid buffers that are dispensed by the activation of deformable storage compartments, generally referred to herein as "blisters", "blister packs" or "blister vessels". The activation of the blisters is generally done using actuators that exert pressure (e.g. mechanical pressure, air pressure, etc.) on the blisters to force liquid out of the blister, through the top plate and onto one or more locations (e.g. one or more electrowetting pads) on the bottom substrate as is more fully outlined below. In some embodiments, the actuators for blister activation are contained in the bays of the instrument into which the cartridges fit, e.g. a mechanical actuator or an air pump that puts pressure on the deformable blisters. The instant Figures shows a biochip cartridge with the blister zones exposed, as well as one with a trademark label (which can include a barcode) on the top that hides the blister pressure zones. In general, the blisters can be either sealed at a specific location, generally at the site of the fluid channel leading to the holes in the top plate, such that the seal can be broken. Other embodiments use a uniform blister material that can only rupture in a particular location (e.g. above a hole in the top plate, for example). The blisters can also be ruptured using contained lances that are triggered by the external mechanism. In addition, the blisters can be ruptured and the reagents held in place as needed until dispensing; e.g. the release of the reagents can be time separated from dispensing the reagents.

Air motivation of fluid can be supplied by an air pump external to the cartridge, or alternately supplied by an air blister within the cartridge. In either configuration, air or an inert gas is used to push fluid through the system.

In general, the LRM contains a plurality of blisters that are made of a deformable material that preferentially collapses upon the application of suitable pressure; that is, the materials used to form blisters do not return to their starting shape when the pressure is removed, as this could cause backflow of the applied reagents. In addition, the blisters may be used once (a single application of pressure is done during the assay) or a number of times (e.g. multiple aliquots of reagent are delivered to either a single location or multiple locations during the assay run). For example, one of the blisters contains the immiscible fluid(s), as described herein, which is applied generally as a first step after the sample has been loaded and the cartridge has been inserted into the instrument. In some embodiments, the cartridge can be fabricated with the oil already dispersed on the surface, although this may not be preferable for storage considerations. Alternatively, some blisters are actuated repeatedly for dispensing of the suitable liquid reagent to different pads on the substrate; for example, when the sample droplet is not used to suspend the dried reagents, reconstitution buffer can be added to the different dried reagent pads prior to merging the reagent droplet with the sample droplet. Alternatively multiple blisters containing the same liquid reagent can be used, although this is not generally preferred. This redundancy may be used to deliver the same reagent to multiple locations in the rest of the disposable.

In addition to the immiscible fluid blister, other blisters are used as generally depicted in the Figures. As shown in FIG. 20 for example, lysis buffer (which in some cases can be water for hypotonic lysis, or can be a commercially available lysis buffer, such as those containing chiatropic salts such as guanidinium salts, and or high/low pH, and/or surfactants such as sodium dodecyl sulfate (SDS), Tween 20, Triton-X, etc.) is contained within a blister that is activated to add lysis buffer to the sample. In some cases, the lysis buffer optionally comprises reagents to disrupt undesired enzymatic activity, such as DNase and RNase activity, which are then removed during the bead capture/elution process (although these can be separate reagents, either dried or liquid, that can be added as needed depending on the target analytes and the assay). Other suitable blister vessels include, but are not limited to, blister(s) containing binding buffer for binding of nucleic acids or other target analytes to capture beads, blister(s) containing wash buffer, blister(s) containing the elution buffer (again, which can be water in some embodiments) to elute the adsorbed nucleic acids off the beads, blister(s) containing appropriate reconstitution buffer(s), etc. Air blisters (e.g. containing air or other gases) can also be used to exert pressure on either other blisters or down through ports to facilitate free liquid movement (e.g. liquid not subjected to electronic movement such as electrowetting). In some embodiments, blisters can dispense liquid reagents into other blisters, as one method of mixing reagents, or to recover the vast majority of a valuable reagent by flushing it out of a blister.

In some embodiments, the blisters of the LRM are located directly above the location for dispensing, where the exit port of the blister is aligned with the ports of the top plate such that the fluid is dispensed directly below the exit port of the blister. Alternatively, the LRM may include one or more channels to allow multiple aliquots of reagent liquid to be dispensed simultaneously or sequentially to different locations on the bottom substrate (again, through the ports in the top plate). That is, the channels put the exit port of the blister (however configured, as outlined below) in fluid communication with the appropriate electrowetting location on the substrate.

In addition to the blisters of the LRM, the LRM comprises a sample entry port to introduce a sample into the cartridge. This generally is configured to receive a standard pipette tip, used to add the appropriate volume of sample to the cartridge. Either the LRM or the housing, discussed below, contains a sealing mechanism such as a latched cover to both seal the cartridge so as not to introduce any contaminants as well as prevent the escape of biological materials. In general, as depicted in the figures, it is the housing that comprises the latched sealing cover.

The LRM optionally includes capture beads (e.g. magnetic capture beads) which can be dispensed into the chamber within the electrowetting grid. The beads are the preferred mechanism of transfer between the LRM and the PCB. Typically, beads bind DNA/RNA in the LRM, are washed in the LRM, and then transferred to the PCB with a volume of wash buffer (e.g., 100-200 µl), where electrowetting facilitates elution of the DNA/RNA in a small volume. Once delivered to the cartridge, the beads are collected over an area of the electrowetting grid which has a magnet applied underneath from the bottom part of the bay. Beads with elution buffer are subsequently subjected to electrowetting to mix for elution. The elution volume of a few microliters would be difficult to achieve on the LRM or in any other non-electrowetting setup.

In some embodiments, the LRM can contain pumps to facilitate movement of the reagents and/or sample from the LRM to the bottom substrate, although in general the "no moving parts" principle dictates that these pumps, if necessary, would be off chip. A number of microfluidic pumps are known. In a typical embodiment, however, the pump is not contained in the cartridge. A notable exception is where a pump, such as a pair of umbrella valves or other type of one-way valve, is contained in the LRM but driven by an external mechanism.

In some optional embodiments, some of the ports and/or channels comprise one or more valve(s) to control the flow of reagents and/or samples. In many cases, one way valves find use, such that a fluid is moved from the LRM into the chamber volume and cannot backflow or return to the LRM. Generically, these include normally-open valves and normally-closed valves. There are a variety of one way valves known, e.g., duck bill valves.

In some optional embodiments, the LRM/top plate components contain one or more vent(s) to reduce air bubbles, which are particularly undesirable in the detection zone, and can be formed in some instances during the thermocycling. In these embodiments, the vent(s) can simply be holes or vias that connect certain areas of the reaction chamber with a reservoir in the LRM. Alternatively, the vents may use valves (particularly one way valves), or can be coated or filled with materials that allow air to pass but prevent liquid exit (such as GORTEX® or other hydrophobic materials). In a typical embodiment, a Teflon® membrane with about 0.2 µm pores can be used. Generally, any sufficiently hydrophobic material with pores roughly in the 0.1-1 micron range could be used.

In addition to the deformable blisters used to dispense liquids during the assay protocols, the LRM can also comprise one or more chambers that are generally not deformable but are used for specific sample or reagent handling. For example, as outlined herein, the LRM can also optionally comprise one or more mixing chambers that facilitate mixing of the sample with reagents. For example, as described herein, chamber(s) containing impeller(s) can be used, particularly to grind up solid samples, maximize exposure of sample to capture beads, mix sample with chemical lysis buffer, mix magnetic beads with binding buffer (typically magnetic beads cannot be stored in their binding buffer), etc. Alternatively, mixing can be done within the reaction chamber by moving the sample droplets back and forth between pads, and/or splitting and merging sample droplets to maximize mixing. In some embodiments, one or more chambers of the LRM. Similarly, the LRM can comprise one or more waste chambers in which to place excess or used fluids.

In some optional embodiments, the LRM comprises one or more opening(s) that allow one or more optical sensor(s) to monitor the progress of reagents and sample through the LRM, e.g., to detect a transition point between air and liquid when air is employed to motivate the sample and/or a liquid reagent. The sensor itself is preferably located in the bay. The openings provide the sensor with optical access to "see" into the LRM. Other fluid sensors could be used, notably inductive, capacitive, resistive, or other electrical sensors.

In some embodiments, the LRM can include one or more porous filters to remove particulates from the sample prior to downstream processing. For example, there may be a filter between the capture beads and the elution chamber, such that the eluent flows through a filter to remove particulates prior to the amplification step. The filter is preferably located as early as possible in the process flow to keep particulate matter out of system, or immediately after lysis to remove anything that did not get lysed.

Particular and specific embodiments of the LRM utilize deformable fluid vessels, or blisters, as described in more detail below.

Manipulation of Deformable Fluid Vessels

In the present invention, one LRM embodiment that finds use in a variety of systems and assays relies on the use of deformable fluid vessels, sometimes referred to herein as "blisters" or "blister packs". There are a number of configurations and embodiments, as generally outlined in FIGS. 1-19.

An actuator mechanism for compressing deformable fluid vessels—such as blisters on a liquid reagent module—embodying aspects of the present invention is shown at reference number 50 in FIG. 2. The actuator mechanism 50 will reside in the top part of the bay and may include an articulated blister actuator platen assembly 52 and a sliding actuator plate 66. The sliding actuator plate 66 is configured to be movable in a direction that is generally parallel to the plane of the liquid reagent module—horizontally in the illustrated embodiment—and may be driven by a linear actuator, a rack and pinion, a belt drive, or other suitable motive means. Sliding actuator plate 66, in the illustrated embodiment, has V-shaped edges 76 that are supported in four V-rollers 74 to accommodate movement of the plate 66 in opposite rectilinear directions, while holding the sliding actuator plate 66 at a fixed spacing from the actuator platen assembly 52. Other features may be provided to guide the actuator plate 66, such as rails and cooperating grooves. A component 40—which may comprise liquid reagent module described above—having one or more deformable fluid vessels, such as blisters 36 and 38, is positioned within the actuator mechanism 50 beneath the articulated blister actuator platen assembly 52.

Further details of the configuration of the articulated blister actuator platen assembly 52 and the operation thereof are shown in FIGS. 3A-6B.

Figure 3A:
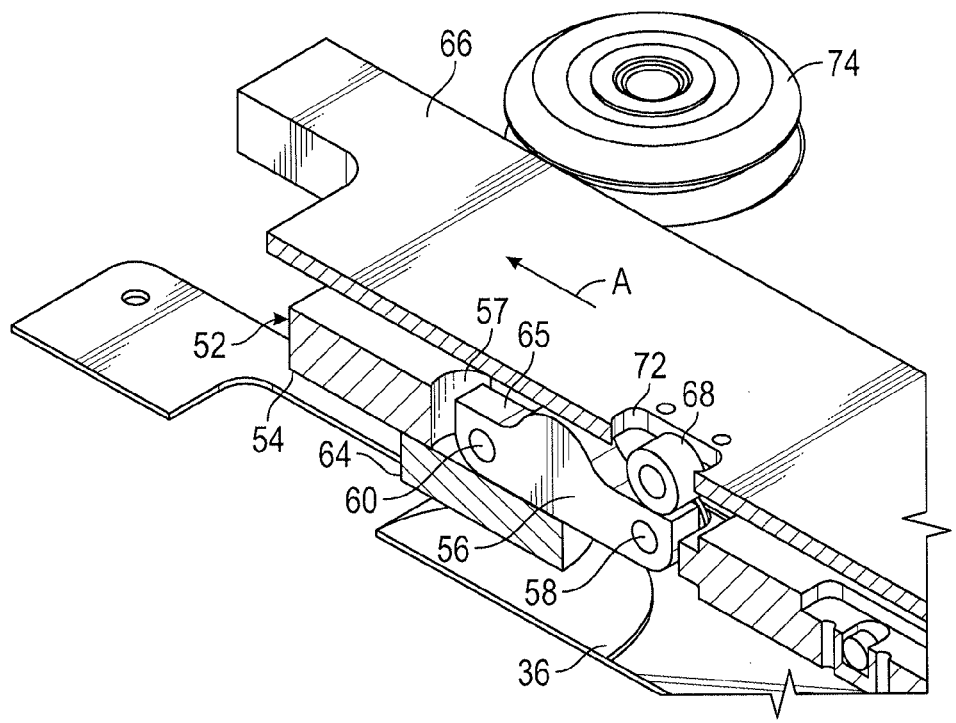
FIG. 3A is a partial, cross-sectional perspective view of the articulated blister actuator platen assembly in an initial, unactuated state.
Figure 3B:
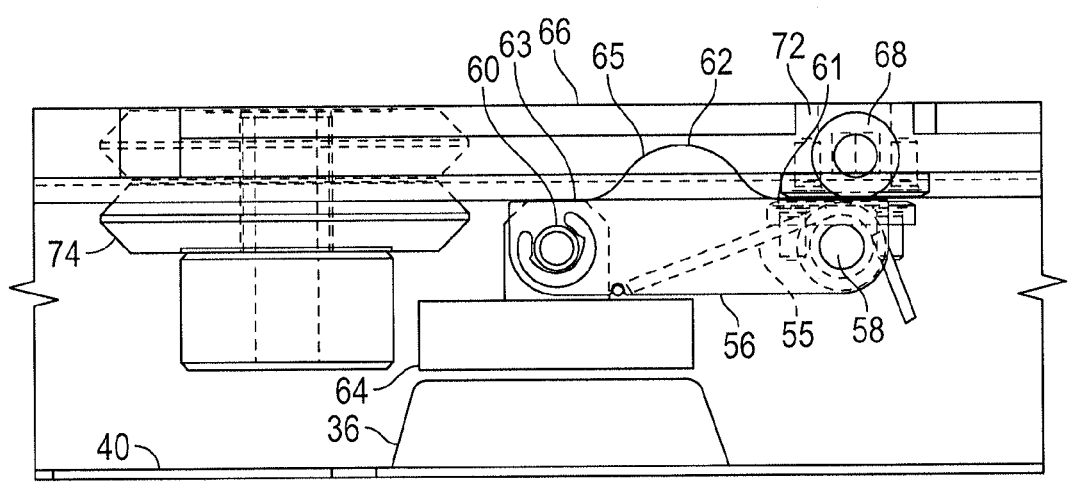
FIG. 3B is a partial, cross-sectional side view of the articulated blister actuator platen assembly in the initial unactuated state.

As shown in FIGS. 3A and 3B, the actuator platen assembly 52 includes a chassis 54. A cam body 56 is disposed within a slot 57 of the chassis 54 and is attached to the chassis 54 by a first pivot 58. A platen 64 is pivotally attached to the cam body 56 by means of a second pivot 60. The cam body 56 is held in a horizontal, unactuated position within the slot 57 by means of a torsional spring 55 coupled around the first pivot 58.

Cam body 56 further includes a cam surface 65 along one edge thereof (top edge in the figure) which, in the exemplary embodiment shown in FIG. 3B, comprises an initial flat portion 61, a convexly-curved portion 62, and a second flat portion 63. The sliding actuator plate 66 includes a cam follow 68 (a roller in the illustrated embodiment) rotatably mounted within a slot 72 formed in the actuator plate 66. In an embodiment of the invention, one cam body 56 and associated platen 64 and cam follower 68 are associated with each deformable vessel (e.g. blister 36) of the liquid reagent module 40.

The actuator platen assembly 52 and the sliding actuator plate 66 are configured to be movable relative to each other. In one embodiment, the actuator platen assembly 52 is fixed, and the actuator plate 66 is configured to move laterally relative to the platen assembly 52, supported by the V-rollers 74. Lateral movement of the sliding actuator plate 66, e.g., in the direction "A", causes the cam follower 68 to translate along the cam surface 65 of the cam body 56, thereby actuating the cam body 56 and the platen 64 attached thereto.

Figure 4A:
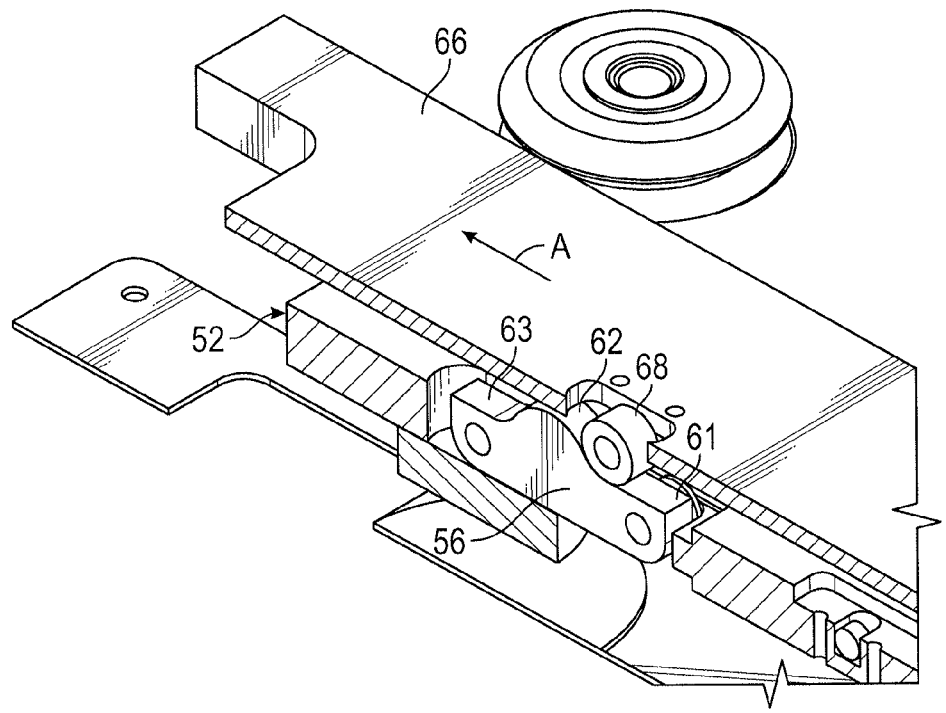
FIG. 4A is a partial, cross-sectional perspective view of the articulated blister actuator platen assembly as the platen is about to be actuated.
Figure 4B:
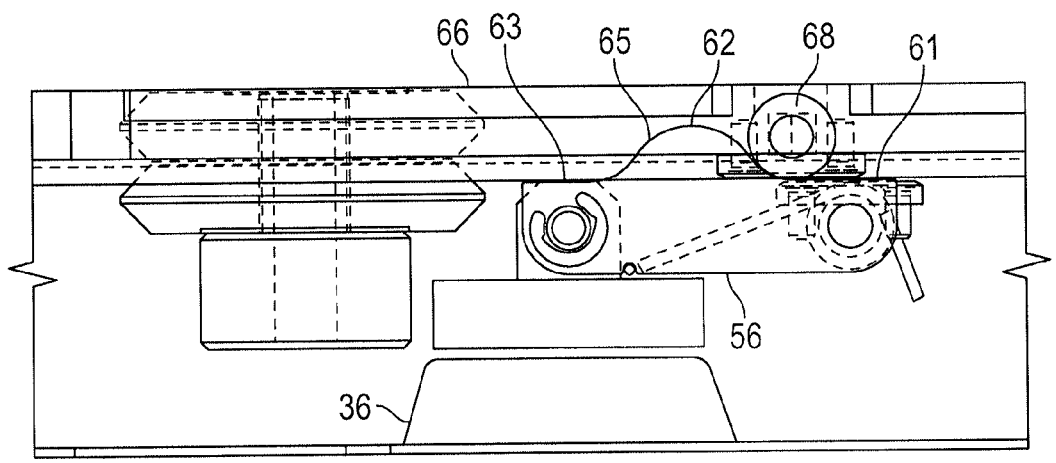
FIG. 4B is a partial, cross-sectional side view of the articulated blister actuator platen assembly as the platen is about to be actuated.

In FIGS. 3A and 3B, before the sliding actuator plate 66 has begun to move relative to the actuator platen assembly 52, the cam follower 68 is disposed on the initial flat portion 61 of the cam surface 65 of the cam body 56. In FIGS. 4A and 4B, the sliding actuator plate 66 has moved relative to the actuator platen assembly 52 in the direction "A" so that the cam follower 68 has moved across the initial flat portion 61 of the cam surface 65 and has just begun to engage the upwardly curved contour of the convexly-curved portion 62 of the cam surface 65 of the cam body 56.

Figure 5A:
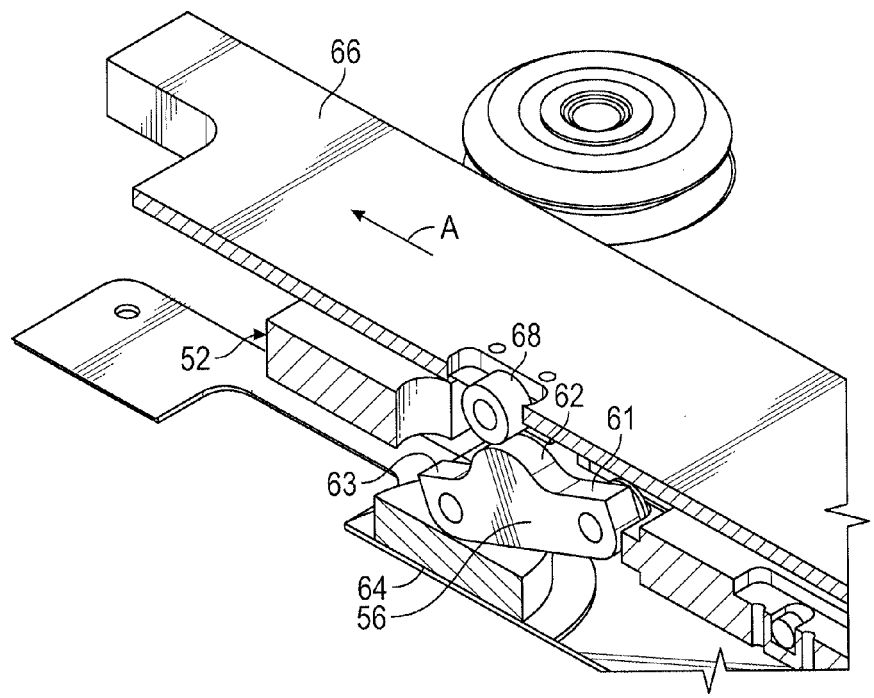
FIG. 5A is a partial, cross-sectional perspective view of the articulated blister actuator platen assembly with the platen in a fully actuated state.
Figure 5B:
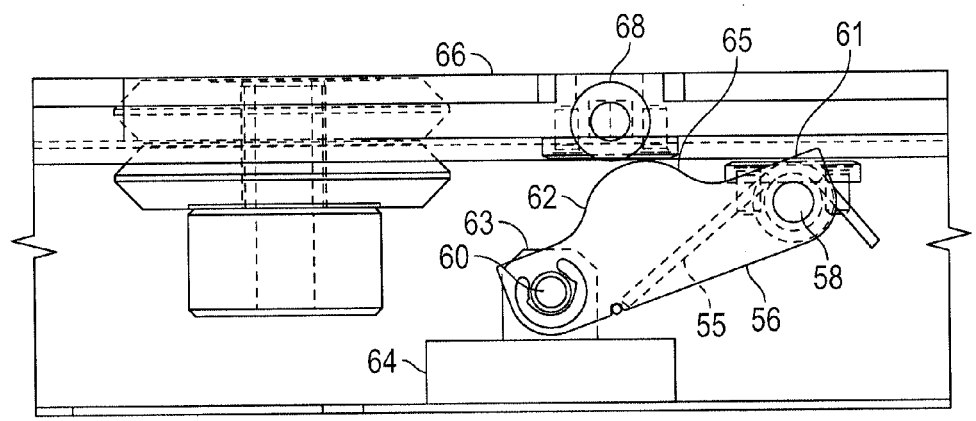
FIG. 5B is a partial, cross-sectional side view of the articulated blister actuator platen assembly with the platen in a fully actuated state.

In FIGS. 5A and 5B, the sliding actuator plate 66 has proceeded in the direction "A" to a point such that the cam follower 68 is at the topmost point of the convexly-curved portion 62 of the cam surface 65, thereby causing the cam body 56 to rotate about the first pivot 58. The platen 64 is lowered by the downwardly pivoting cam body 56 and pivots relative to the cam body 56 about the second pivot 60 and thereby compresses the blister 36.

Figure 6A:
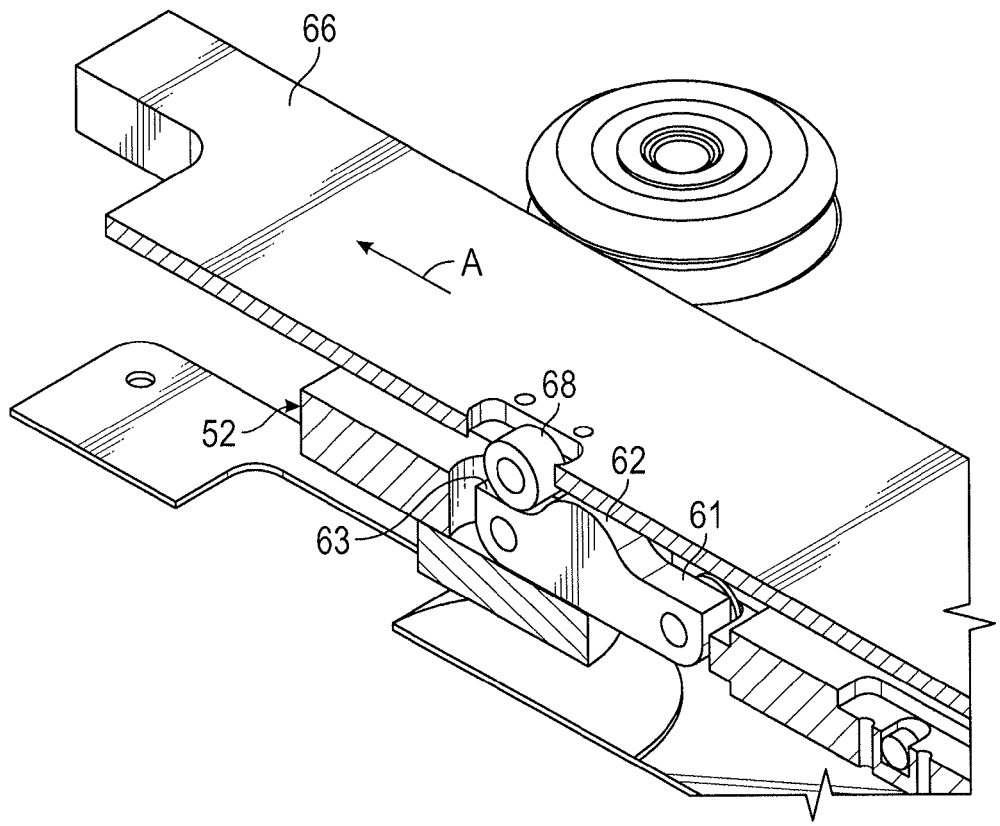
FIG. 6A is a partial, cross-sectional perspective view of the articulated blister actuator platen assembly with the platen returned to the unactuated state.
Figure 6B:
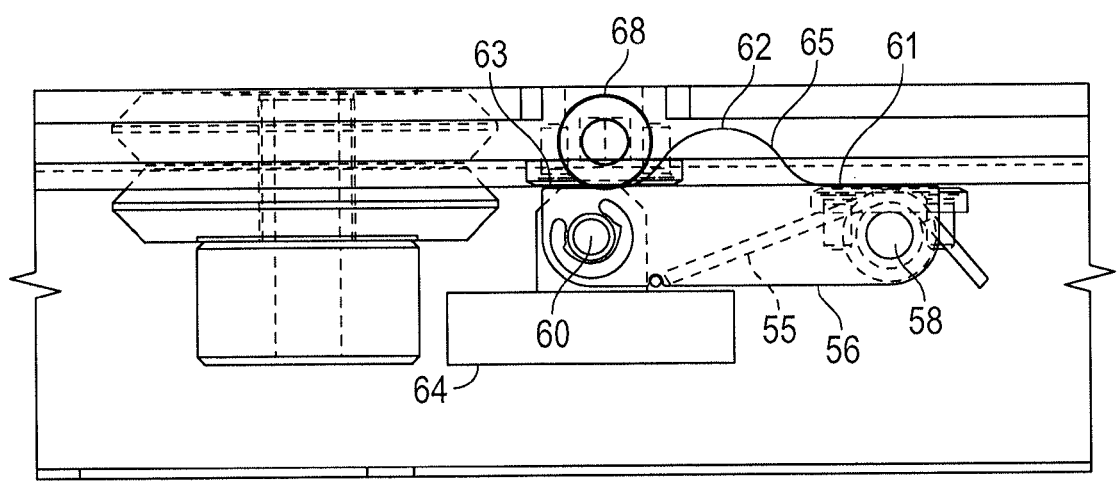
FIG. 6B is a partial, cross-sectional side view of the articulated blister actuator platen assembly with the platen returned to the unactuated state.

In FIGS. 6A and 6B, sliding actuator plate 66 has moved to a position in the direction "A" relative to the actuator platen assembly 52 such that the cam follower 68 has progressed to the second flat portion 63 of the cam surface 65. Accordingly, the cam body 56, urged by the torsion spring 55, pivots about the first pivot 58 back to the unactuated position, thereby retracting the platen 64.

Thus, the articulated blister actuator platen assembly 52 is constructed and arranged to convert the horizontal movement actuator plate 66 into vertical movement of the platen 64 to compress a blister, and movement of the platen does not require pneumatic, electromechanical, or other components at larger distances above and/or below the liquid module.

An alternative embodiment of a blister compression actuator mechanism is indicated by reference number 80 in FIGS. 7A and 7B. Actuator 80 includes a linear actuator 82 that is coupled to a cam rail 84. Cam rail 84 is supported for longitudinal movement by a first support rod 96 extending transversely through slot 86 and a second support rod 98 extending transversely through a second slot 88 formed in the cam rail 84. The first support rod 96 and/or the second support rod 98 may include an annular groove within which portions of the cam rail 84 surrounding slot 86 or slot 88 may be supported, or cylindrical spacers may be placed over the first support rod 96 and/or the second support rod 98 on opposite sides of the cam rail 84 to prevent the cam rail 84 from twisting or sliding axially along the first support rail 96 and/or the second support rail 98.

Cam rail 84 includes one or more cam profile slots. In the illustrated embodiment, cam rail 84 includes three cam profile slots 90, 92, and 94. Referring to cam profile slot 90, in the illustrated embodiment, slot 90 includes, progressing from left to right in the figure, an initial horizontal portion, a downwardly sloped portion, and a second horizontal portion. The shapes of the cam profile slots are exemplary, and other shapes may be effectively implemented. The actuator mechanism 80 also includes a platen associated with each cam profile slot. In the illustrated embodiment, actuator 80 includes three platens 100, 102, 104 associated with cam profile slots 90, 92, 94, respectively. First platen 100 is coupled to the cam profile slot 90 by a cam follower pin 106 extending transversely from the platen 100 into the cam profile slot 90. Similarly, second platen 102 is coupled to the second cam profile slot 92 by a cam follower pin 108, and the third platen 104 is coupled to the third cam profile slot 94 by a cam follower pin 110. Platens 100, 102, 104 are supported and guided by a guide 112, which may comprise a panel having openings formed therein conforming to the shape of each of the platens.

In FIG. 7A, cam rail 84 is in its furthest leftmost position, and the platens 100, 102, 104 are in their unactuated positions. Each of the cam follower pins 106, 108, 110 is in the initial upper horizontal portion of the respective cam profile slot 90, 92, 94. As the cam rail 84 is moved longitudinally to the right, in the direction "A" shown in FIG. 7B, by the linear actuator 82, each cam follower pin 106, 108, 110 moves within its respective cam profile slot 90, 92, 94 until the cam follower pin is in the lower, second horizontal portion of the respective cam profile slot. Movement of each of the pins 106, 108, 110 downwardly within its respective cam profile slot 90, 92, 94 causes a corresponding downward movement of the associated platen 100, 102, 104. This movement of the platens thereby compresses a fluid vessel (or blister) located under each platen. Each platen may compress a vessel directly in contact with the platen or it may contact the vessel through one or more intermediate components located between the vessel and the corresponding platen.

Thus, the blister compression actuator mechanism 80 is constructed and arranged to convert the horizontal movement cam rail 84, driven by the linear actuator 82, into vertical movement of the platens 100, 102, 104 to compress blisters, and movement of the platens does not require pneumatic, electromechanical, or other components at larger distances above and/or below the liquid module.

When compressing a fluid vessel, or blister, to displace the fluid contents thereof, sufficient compressive force must be applied to the blister to break, or otherwise open, a breakable seal that is holding the fluid within the vessel. The amount of force required to break the seal and displace the fluid contents of a vessel typically increases as the volume of the vessel increases. This is illustrated in the bar graph shown in FIG. 11, which shows the minimum, maximum, and average blister burst forces required for blisters having volumes of 100, 200, 400, and 3000 microliters. The average force required to burst a blister of 400 or less microliters is relatively small, ranging from an average of 10.7 lbf to 11.5 lbf. On the other hand, the force required to burst a blister of 3000 microliters is substantially larger, with an average burst force of 43.4 lbf and a maximum required burst force of greater than 65 lbf. Generating such large forces can be difficult, especially in low profile actuator mechanisms, such as those described above, in which horizontal displacement of an actuator is converted into vertical, blister-compressing movement of a platen.

Accordingly, aspects of the present invention are embodied in methods and apparatus for opening a fluid vessel, or blister, in a manner that reduces the amount of force required to burst the vessel and displace the fluid contents of the vessel.

Such aspects of the invention are illustrated in FIGS. 8A and 8B. As shown in FIG. 8A, a fluid vessel (or blister) 122 is mounted on a substrate 124 and is connected by means of a channel 130 to a sphere blister 128. In certain embodiments, channel 130 may be initially blocked by a breakable seal. A film layer 129 may be disposed on the bottom of the substrate 124 to cover one or more channels formed in the bottom of the substrate 124 to form fluid conduits. An opening device, comprising a sphere 126 (e.g., a steel ball bearing) is enclosed within the sphere blister 128 and is supported, as shown in FIG. 8A, within the sphere blister 128 by a foil partition or septum 125. The foil partition 125 prevents fluid from flowing from the vessel 122 through a recess 127 and fluid exit port 123. Upon applying downward force to the sphere 126, however, a large local compressive stress is generated due to the relatively small surface size of the sphere 126, and the foil partition 125 can be broken with relatively little force to push the sphere 126 through the partition 125 and into the recess 127, as shown in FIG. 8B. With the foil partition 125 broken, a relatively small additional force is required to break a seal within channel 130 and force the fluid to flow from the vessel 122 through the fluid exit port 123.

In FIG. 8B, the sphere blister 128 is shown intact. In some embodiments, a force applied to the sphere 126 to push it through the foil partition 125 would also collapse the sphere blister 128.

An apparatus for opening a vessel by pushing a sphere 126 through foil partition 125 is indicated by reference number 120 in FIGS. 9A, 9B, 9C, 9D. In the illustrated embodiment, the apparatus 120 includes a ball actuator 140 extending through an opening formed through a blister plate, or platen, 132. With the blister plate 132 and an actuator 138 configured for moving the blister plate 132 disposed above the vessel 122, the ball actuator 140 is secured in a first position, shown in FIG. 9A, by a detent 136 that engages a detent collar 144 formed in the ball actuator 140.

Figure 9A:
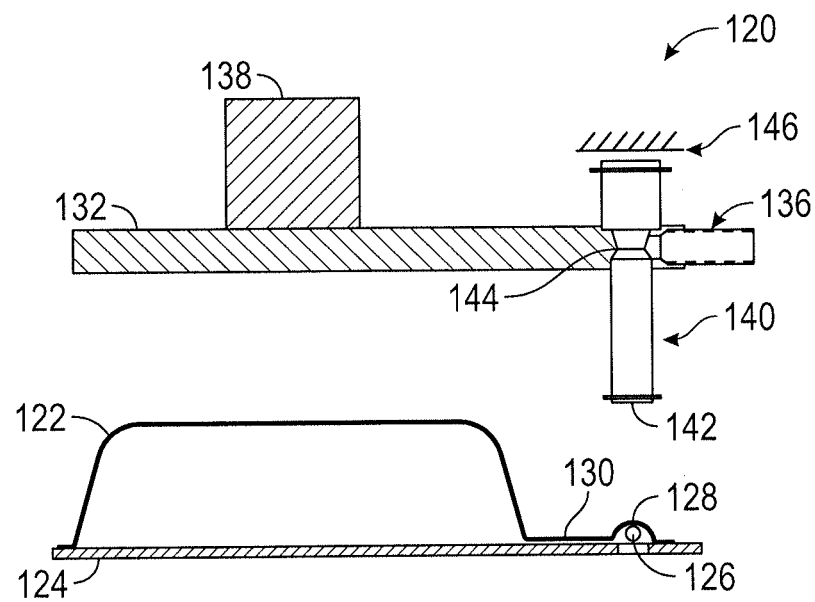
FIGS. 9A-9D are side views showing an apparatus for opening a collapsible vessel configured to facilitate opening of the vessel in various states.
Figure 9B:
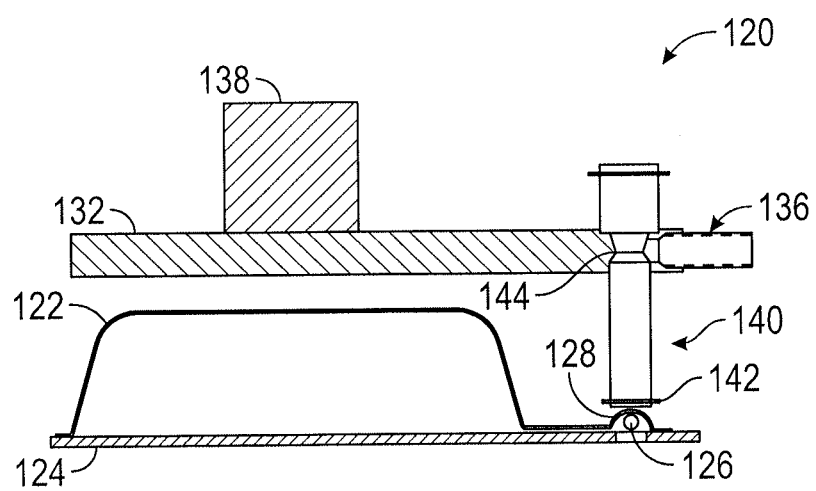

As shown in FIG. 9B, the blister plate 132 is moved by the actuator 138 down to a position in which a contact end 142 of the ball actuator 140 contacts the top of the of the sphere blister 128. Actuator 138 may comprise a low profile actuator, such as actuator mechanisms 50 or 80 described above.

Figure 9C:
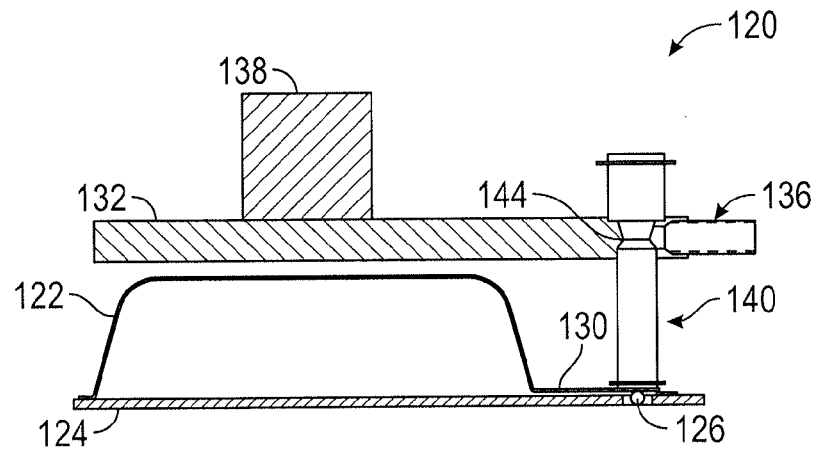

As shown in FIG. 9C, continued downward movement of the blister plate 132 by the actuator 138 causes the ball actuator 140 to collapse the sphere blister 128, thereby pushing the opening device, e.g., sphere 126, through a partition blocking fluid flow from the vessel 122. In this regard, it will be appreciated that the detent must provide a holding force sufficient to prevent the ball actuator 140 from sliding relative to the blister plate 132 until after the sphere 126 has pierced the partition. Thus, the detent must provide a holding force sufficient to collapse the sphere blister 128 and push the sphere 126 through a partition.

Figure 9D:
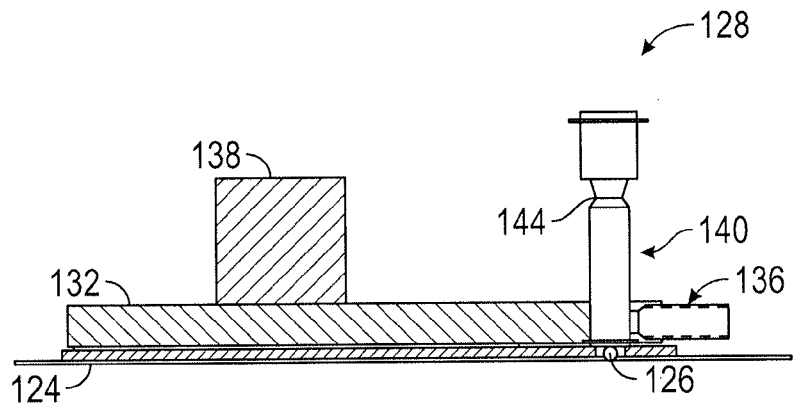

As shown in FIG. 9D, continued downward movement of the blister plate 132 by the actuator 138 eventually overcomes the holding force provided by the detent 136, and the ball actuator 140 is then released to move relative to the blister plate 132, so that the blister plate can continue to move down and collapse the vessel 122.

After the vessel 122 is collapsed, the blister plate 132 can be raised by the actuator 138 to the position shown in FIG. 9A. As the blister plate 132 is being raised from the position shown in FIG. 9D to the position shown in 9A, a hard stop 146 contacts a top end of the ball actuator 140 to prevent its continued upward movement, thereby sliding the ball actuator 140 relative to the blister plate 132 until the detent 136 contacts the detent collar 144 to reset the ball actuator 140.

Figure 10:
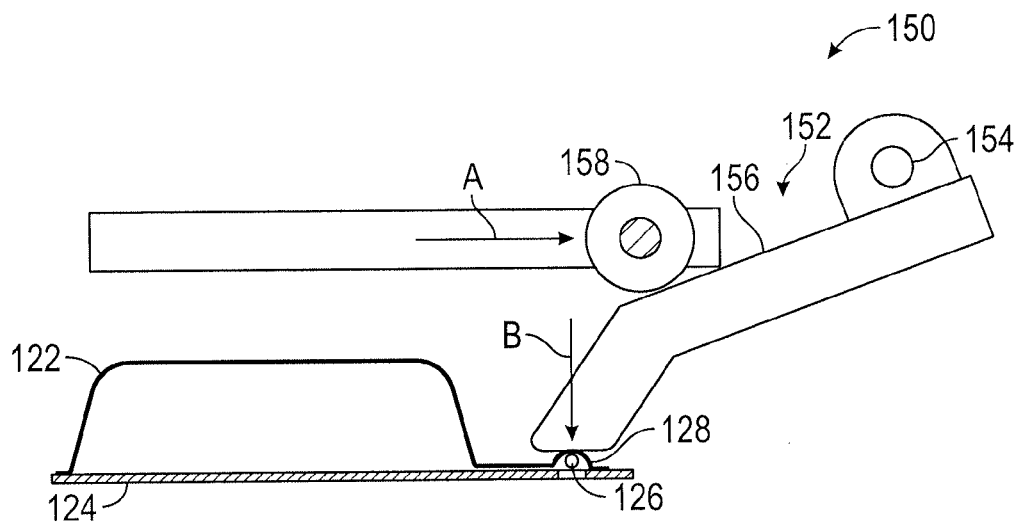
FIG. 10 is a side view of an alternative embodiment of an apparatus for opening a collapsible vessel configured to facilitate opening of the vessel.
Figure 11:
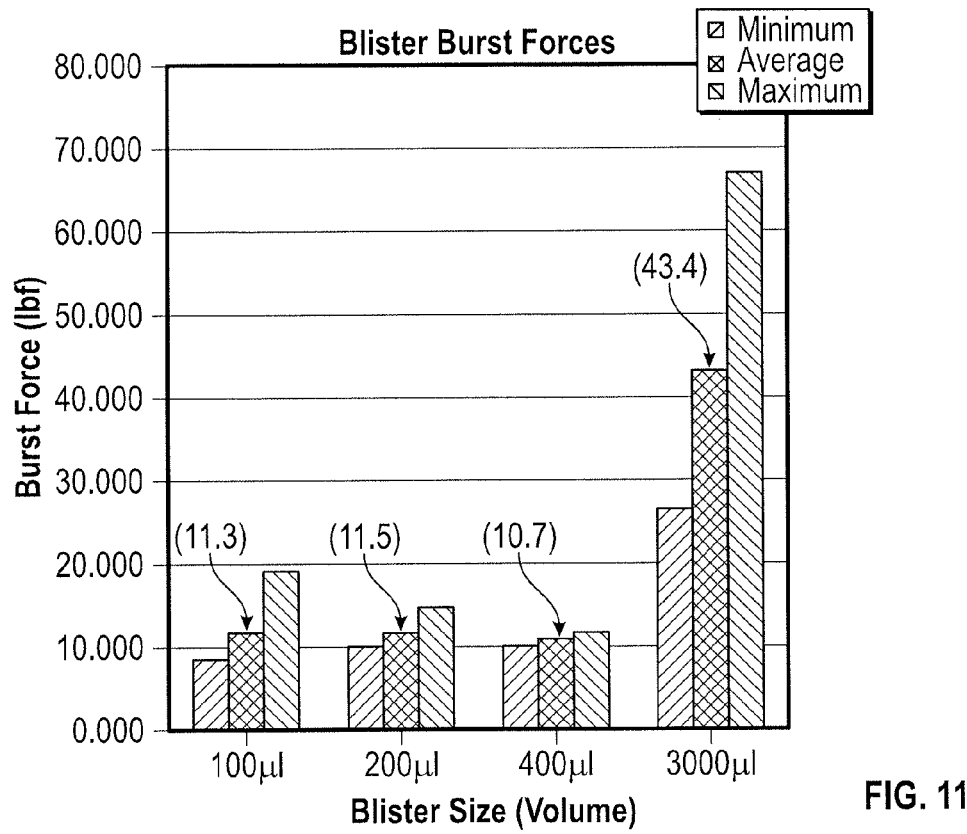
FIG. 11 is a bar graph showing exemplary burst forces for fluid-containing blisters of varying volumes.

An alternative embodiment of an apparatus for opening a vessel embodying aspects of the present invention is indicated by reference number 150 in FIG. 10. Apparatus 150 includes a pivoting ball actuator 152 configured to pivot about a pivot pin 154. A top surface 156 of the pivoting ball actuator 152 comprises a cam surface, and a cam follower 158, comprising a roller, moving in the direction "A" along the cam surface 156 pivots the actuator 152 down in the direction "B" to collapse the sphere blister 128 and force the sphere 126 through the foil partition 125. Pivoting actuator 152 may further include a torsional spring (not shown) or other means for restoring the actuator to an up position disengaged with the sphere blister 128 when the cam follower 158 is withdrawn.

Figure 12:
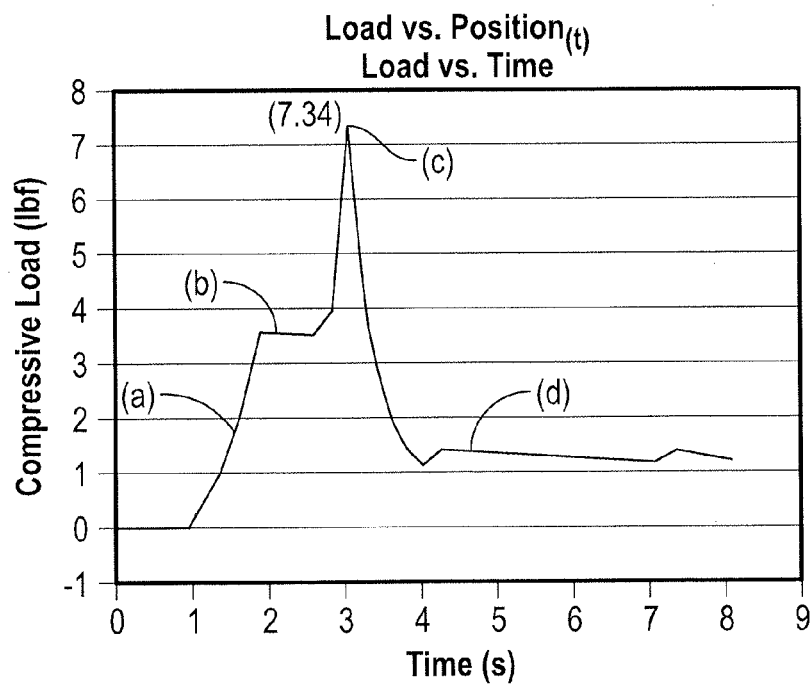
FIG. 12 is a load versus time plot of the compression load versus time during a blister compression.

FIG. 12 is a plot of compressive load versus time showing an exemplary load versus time curve for an apparatus for opening a vessel embodying aspects of the present invention. As the apparatus contacts and begins to compress the sphere blister 128, the load experiences an initial increase as shown at portion (a) of the graph. A plateau shown at portion (b) of the graph occurs after the sphere 126 penetrates the foil partition 125. A second increase in the force load occurs when the blister plate 132 makes contact with and begins compressing the vessel 122. A peak, as shown at part (c) of the plot, is reached as a breakable seal within channel 130 between the vessel 122 and the sphere blister 128 is broken. After the seal has been broken, the pressure drops dramatically, as shown at part (d) of the plot, as the vessel 122 is collapsed and the fluid contained therein is forced through the exit port 123 (See FIGS. 8A, 8B) supporting the sphere 126.

Figure 13A:
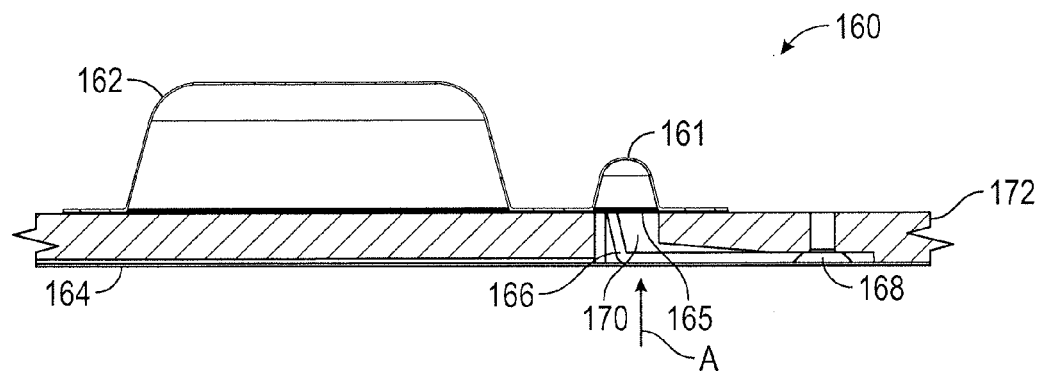
FIG. 13A is a partial, cross-sectional side view of an alternative apparatus for opening a collapsible vessel configured to facilitate opening of the vessel.
Figure 13B:
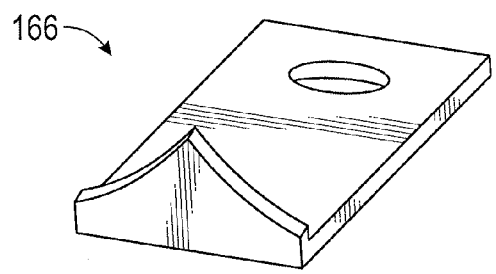
FIG. 13B is a perspective view of a cantilever lance used in the embodiment of FIG. 13A.

An alternative apparatus for opening a vessel is indicated by reference number 160 in FIG. 13A. As shown in FIG. 13A, a fluid vessel (or blister) 162 is mounted on a substrate 172 and is connected by means of a channel—which may or may not be initially blocked by a breakable seal—to a dimple 161. A film layer 164 may be disposed on the bottom of the substrate 172 to cover one or more channels formed in the bottom of the substrate 172 to form fluid conduits. An opening device comprising a cantilevered lance 166 is positioned within a lance chamber 170 formed in the substrate 172 where it is anchored at an end thereof by a screw attachment 168.

A foil partition or septum 165 seals the interior of the dimple 161 from the lance chamber 170. An actuator pushes the lance 170 up in the direction "A" into the dimple 161, thereby piercing the foil partition 165 and permitting fluid to flow from the blister 162 out of the lance chamber 170 and a fluid exit port. The spring force resilience of the lance 166 returns it to its initial position after the upward force is removed. In one embodiment, the lance 166 is made of metal. Alternatively, a plastic lance could be part of a molded plastic substrate on which the blister 162 is formed. Alternatively, a metallic lance could be heat staked onto a male plastic post. A further option is to employ a formed metal wire as a lance.

Figure 14:
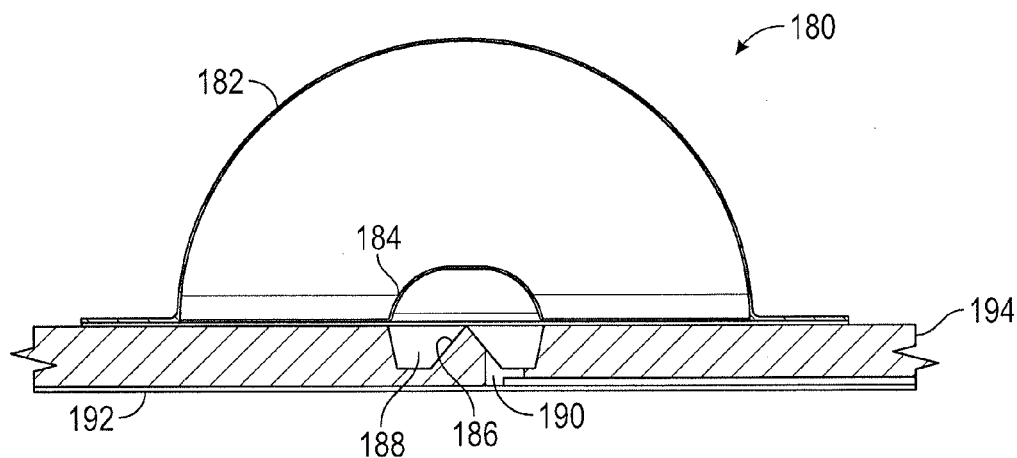
FIG. 14 is a partial, cross-sectional side view of an alternative apparatus for opening a collapsible vessel configured to facilitate opening of the vessel.

A further alternative embodiment of an apparatus for opening a vessel is indicated by reference number 180 in FIG. 14. A component having one or more deformable vessels includes at least one blister 182 formed on a substrate 194. In the arrangement shown in FIG. 14, an internal dimple 184 is formed inside the blister 182. Internal dimple 184 encloses an opening device comprising a fixed spike 186 projecting upwardly from a spike cavity 188 formed in the substrate 194. A film layer 192 is disposed on an opposite side of the substrate 194. As an actuator presses down on the blister 182, internal pressure within the blister 182 causes the internal dimple 184 to collapse and invert. The inverted dimple is punctured by the fixed spike 186, thereby permitting fluid within the blister 182 to flow through an exit port 190.

Figure 15A:
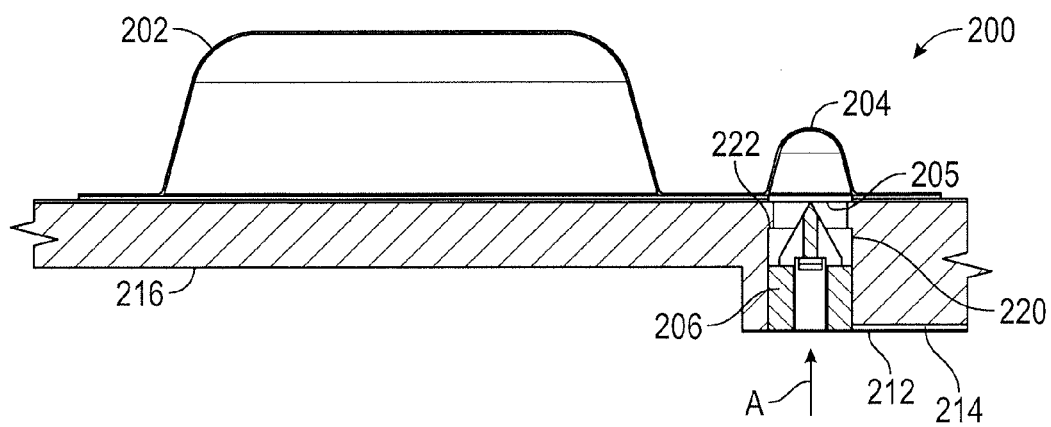
FIG. 15A is a partial, cross-sectional side view of an alternative apparatus for opening a collapsible vessel configured to facilitate opening of the vessel.
Figure 15B:
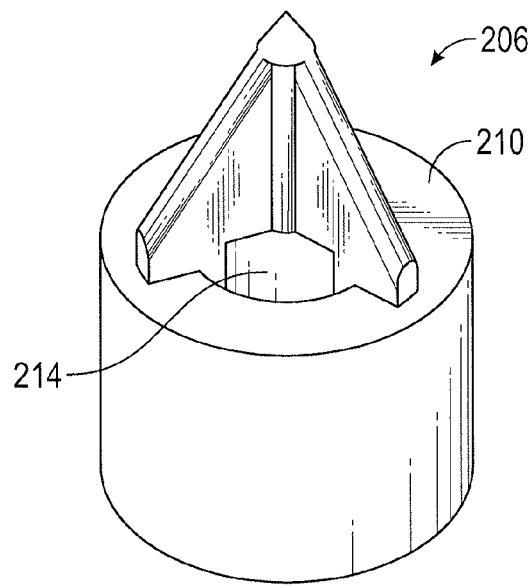
FIG. 15B is a perspective view of a lancing pin used in the apparatus of FIG. 15A.

An alternative apparatus for opening a vessel is indicated by reference number 200 in FIG. 15A. As shown in FIG. 15A, a fluid vessel (or blister) 202 is mounted on a substrate 216 and is connected by means of a channel—which may or may not be initially blocked by a breakable seal—to a dimple 204. An opening device comprising a lancing pin 206 having a fluid port 208 formed through the center thereof (see FIG. 15B) is disposed within a segmented bore 220 formed in the substrate 216 beneath the dimple 204. A partition or septum 205 separates the dimple 204 from the bore 246, thereby preventing fluid from exiting the blister 202 and dimple 204. An actuator (not shown) presses on a film layer 212 disposed on a bottom portion of the substrate 216 in the direction "A" forcing the lancing pin 206 up within the segmented bore 220 until a shoulder 210 formed on the lancing pin 206 encounters a hard stop 222 formed in the segmented bore 246. A lancing point of the pin 206 pierces the partition 205 thereby permitting fluid to flow through the fluid port 214 in the lancing pin 206 and out of a fluid exit channel 214.

Figure 16A:
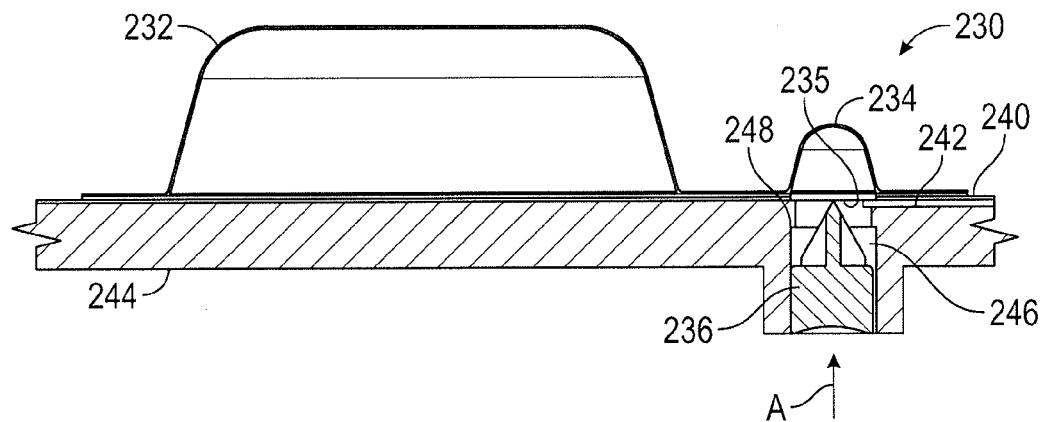
FIG. 16A is a partial, cross-sectional side view of an alternative apparatus for opening a collapsible vessel configured to facilitate opening of the vessel.
Figure 16B:
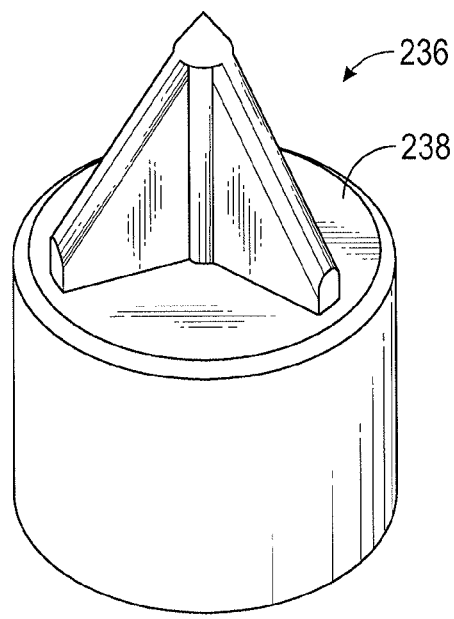
FIG. 16B is a perspective view of a lancing pin used in the apparatus of FIG. 16A.

An alternative embodiment of an apparatus for opening a vessel is indicated by reference number 230 in FIGS. 16A and 16B. As shown in FIG. 16A, a fluid vessel (or blister) 232 is mounted on a substrate 244 and is connected by means of a channel—which may or may not be initially blocked by a breakable seal—to a dimple 234. An opening device comprising a lancing pin 236 is disposed within a segmented board 246 formed in the substrate 244 beneath the dimple 234. A partition or septum 235 separates the dimple 234 from the segmented bore 246. The upper surface of the substrate 244 is sealed with a film 240 before the blister 232 and dimple 234 are adhered. An actuator (not shown) pushes up on the lancing pin 236 in the direction "A" until a shoulder 238 formed on the lancing pin 236 encounters hard stop 248 within the bore 246. The pin 236 thereby pierces the partition 235 and remains in the upper position as fluid flows out along an exit channel 242 formed on an upper surface of the substrate 244. A fluid tight seal is maintained between the pin 238 and the bore 246 by a slight interference fit.

As the collapsible fluid vessels of a liquid reagent module are configured to be compressed and collapsed to displace the fluid contents from the vessel(s), such vessels are susceptible to damage or fluid leakage due to inadvertent exposures to contacts that impart a compressing force to the vessel. Accordingly, when storing, handling, or transporting a component having one or more collapsible fluid vessels, it is desirable to protect the fluid vessel and avoid such inadvertent contact. The liquid reagent module could be stored within a rigid casing to protect the collapsible vessel(s) from unintended external forces, but such a casing would inhibit or prevent collapsing of the vessel by application of an external force. Thus, the liquid reagent module would have to be removed from the casing prior to use, thereby leaving the collapsible vessel(s) of the module vulnerable to unintended external forces.

Figure 17:
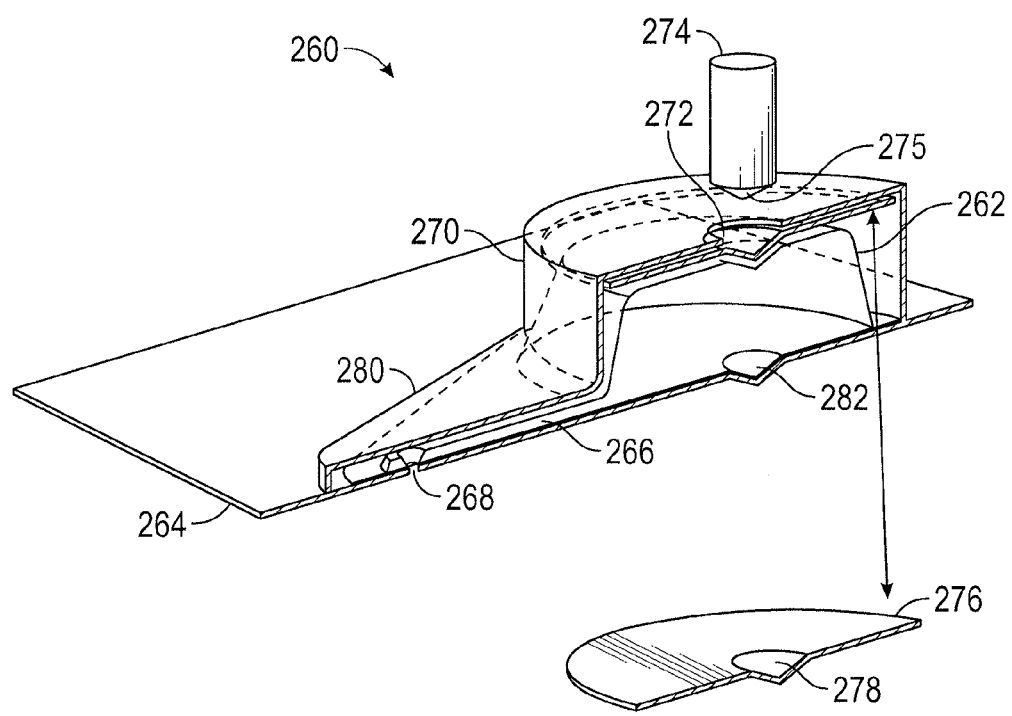
FIG. 17 is an exploded, cross-sectional, perspective view of an apparatus for protecting and interfacing with a collapsible vessel.
Figure 18:
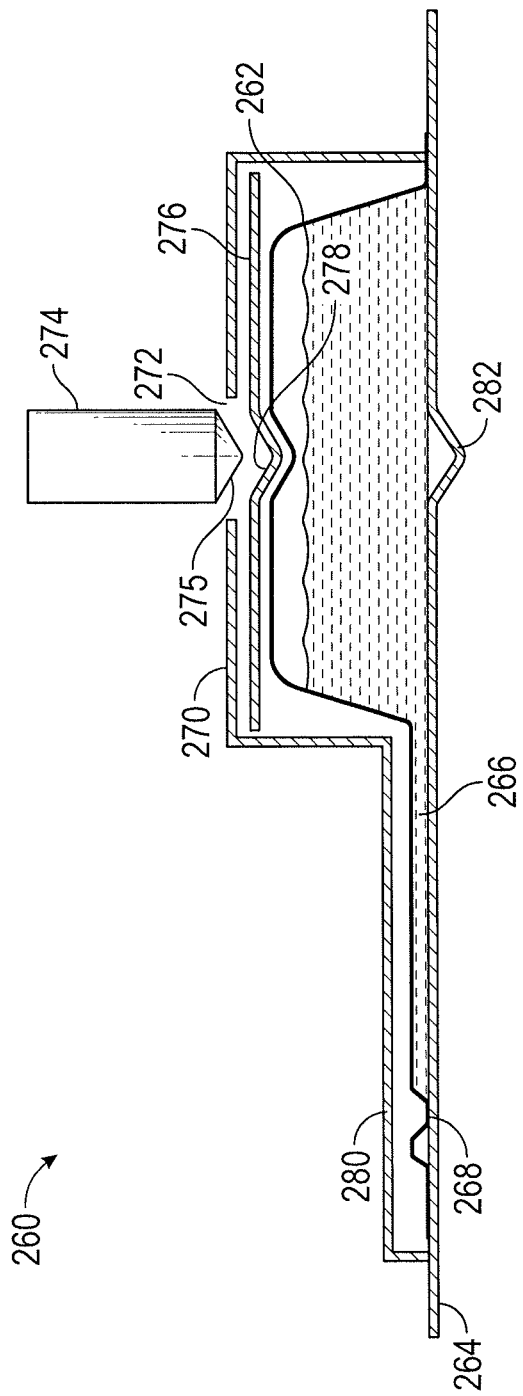
FIG. 18 is a cross-sectional, side view of the apparatus for protecting and interfacing with a collapsible vessel in an unactuated state.
Figure 19:
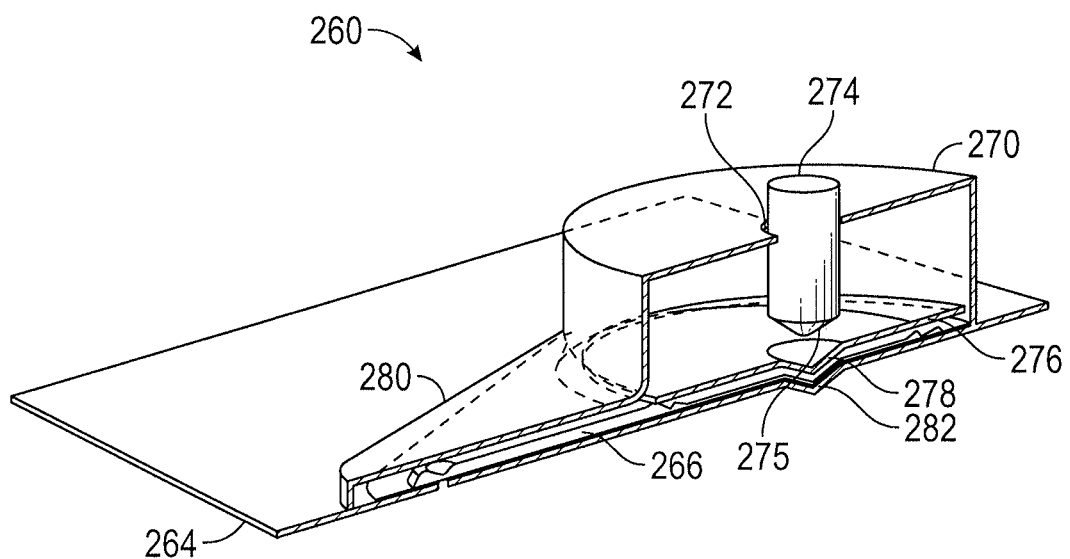
FIG. 19 is a cross-sectional, perspective view of the apparatus for protecting and interfacing with a collapsible vessel in fully actuated state.

An apparatus for protecting and interfacing with a collapsible vessel is indicated by reference number 260 in FIGS. 17, 18, and 19. A component with one or more collapsible vessels includes a collapsible blister 262 formed on a substrate 264. A dispensing channel 266 extends from the blister 262 to a frangible seal 268. It is understood that, in some alternative embodiments, the dispensing channel 266 may be substituted with a breakable seal, providing an additional safeguard against an accidental reagent release.

Frangible seal 268 may comprise one of the apparatuses for opening a vessel described above and shown in any of FIGS. 8-16.

A rigid or semi-rigid housing is provided over the blister 262 and, optionally, the dispensing channel 266 as well, and comprises a blister housing cover 270 covering the blister 262 and a blister housing extension 280 covering and protecting the dispensing channel 266 and the area of the frangible seal 268.

A floating actuator plate 276 is disposed within the blister housing cover 270. In the illustrated embodiments, both the blister housing cover 270 and the floating actuator plate 276 are circular, but the housing 270 and the actuator plate 276 could be of any shape, preferably generally conforming to the shape of the blister 262.

The apparatus 260 further includes a plunger 274 having a plunger point 275 at one end thereof. Plunger 274 is disposed above the blister housing cover 270 generally at a center portion thereof and disposed above an aperture 272 formed in the housing 270.

The floating actuator plate 276 includes a plunger receiver recess 278, which, in an embodiment, generally conforms to the shape of the plunger point 275.

The blister 262 is collapsed by actuating the plunger 274 downwardly into the aperture 272. Plunger 274 may be actuated by any suitable mechanism, including one of the actuator mechanisms 50, 80 described above. Plunger 274 passes into the aperture 272 where the plunger point 275 nests within the plunger receiver recess 278 of the floating actuator plate 276. Continued downward movement by the plunger 274 presses the actuator plate 276 against the blister 262, thereby collapsing the blister 262 and displacing fluid from the blister 262 through the dispensing channel 266 to a fluid egress. Continued pressure will cause the frangible seal at 268 to break, or an apparatus for opening the vessel as described above may be employed to open the frangible seal. The plunger point 275 nested within the plunger point recess 278 helps to keep the plunger 274 centered with respect to the actuator plate 276 and prevents the actuator plate 276 from sliding laterally relative to the plunger 274. When the blister is fully collapsed, as shown in FIG. 19, a convex side of the plunger receiver recess 278 of the floating actuator plate 276 nests within a plunger recess 282 formed in the substrate 264.

Accordingly, the blister housing cover 270 protects the blister 262 from inadvertent damage or collapse, while the floating actuator plate inside the blister housing cover 270 permits and facilitates the collapsing of the blister 262 without having to remove or otherwise alter the blister housing cover 270. In components having more than one collapsible vessel and dispensing channel, a blister housing cover may be provided for all of the vessels and dispensing channels or for some, but less than all vessels and dispensing channels.

In addition to the bottom substrate, the top plate and the LRM, the cartridges of the invention comprise an external housing that holds these three components in appropriate fluid communication with each other as applicable as well as provide interconnects to the instrument bays.

External Housing

Thus, the cartridges of the invention include an external housing, which is essentially a protective shell or casing to completely or partially enclose the PCB, top plate, and LRM assembly, yet allow access to functional components such as the electronic connections and the sample port. In general, the external housing is made of a molded material, including, but not limited to, acrylics and plastics, polystyrene and copolymers of styrene and other materials, polypropylene, polyethylene, polybutylene, polyimide, polycarbonate, polyurethanes, etc.

The external housing (and thus the corresponding bays of the devices) is optionally configured to allow only asymmetrical insertion into the apparatus, preferably both "top up" as well as "correct end in". That is, the cartridges can only be inserted in one direction and in one orientation (due to physical design, for example any or all of a housing curved only on one side (depicted in the Figures as curved on the bottom, for example, which allows the insertion only in a "top up" fashion), grooves or fittings in either or both of the cartridge and the bay such that the cartridge can only be inserted in one orientation, e.g. "front to back". See for example the Figures for cartridge and bay grooving. A variety of such techniques are well known in the art.

The external housing can completely encase the other three components or can provide physical access to parts of the LRM, as is generally shown in FIG. 20, depicting general open areas over the blisters. As will be appreciated by those in the art, the access to the blisters, depending on the mechanism to deform the blisters, can also be a smaller access area, for example just a general hole in the housing. In some preferred embodiments, the blister area of the housing will be sealed with a protective cover comprising an easily breakable material (e.g., paper or equivalent) that contains perforated traces corresponding to the outline of each blister. Such a cover will generally protect the cartridge against accidental damage to the blisters during transportation and handling, yet it is not sufficiently resilient to impede efficient reagent dispensing by the blister actuation mechanism as described herein. The housing generally comprises a sealing, latch cover for the sample entry port. In some embodiments, this cover is irreversibly engaged such that once a biological sample has been put in the cartridge and closed no further user access to the cartridge is possible.

In one optional embodiment, the housing comprises a unique cartridge identifier tag, such as an optically readable barcode, that contains information about such things as the specific assay type of the cartridge, lot, batch or manufacturing information, date of manufacturing, storage conditions, etc.

In one optional embodiment, the housing comprises a surface suitable for the attachment of a unique sample identification tag (again, generally an optically readable barcode) to identify the patient that is affixed by the user. As will be appreciated by those in the art, while this could be specific patient information, in general this will be an identifying number or code to preserve patient confidentiality.

III. Devices

Figure 26:
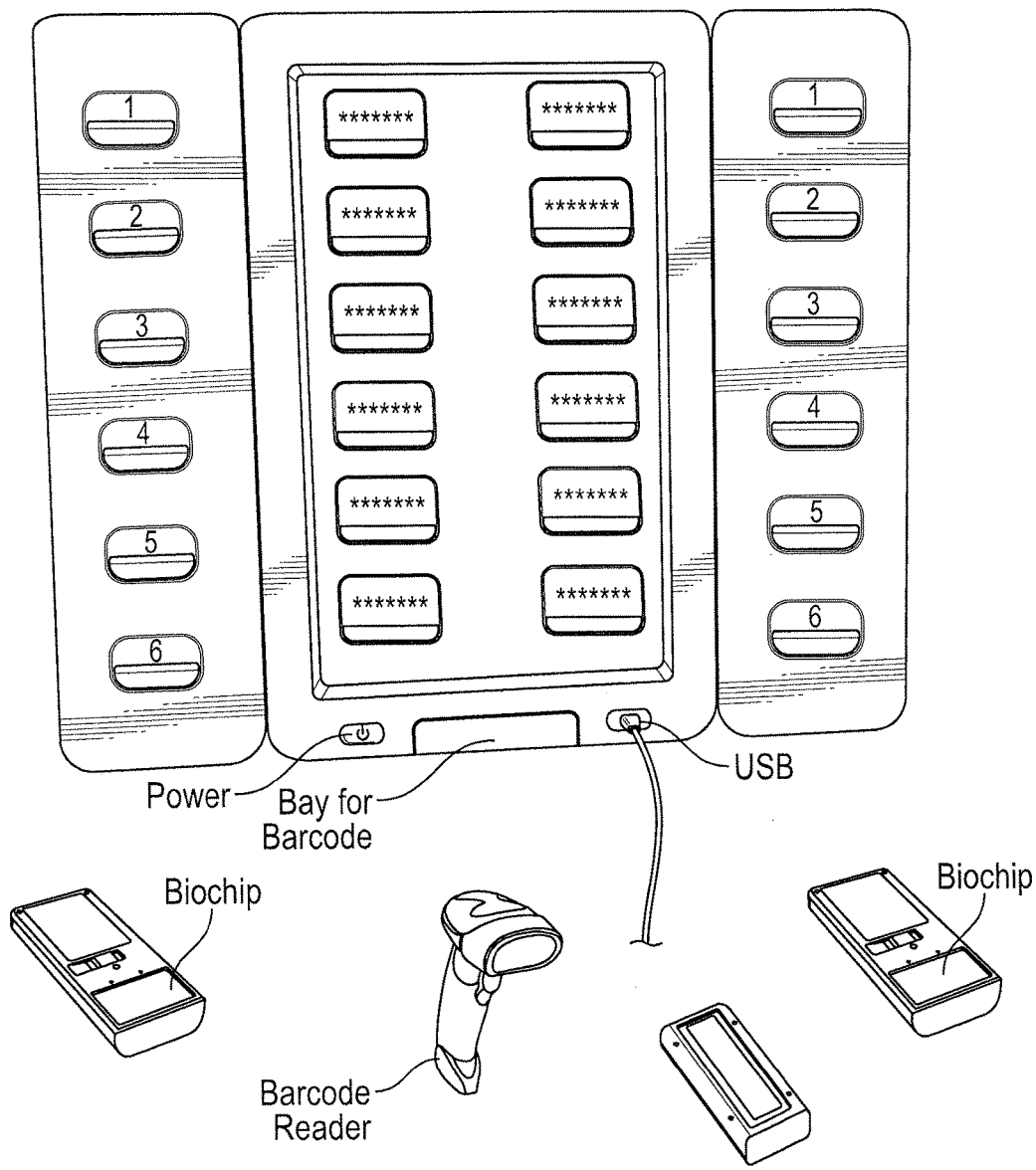
FIG. 26 is a front perspective view of an instrument of the invention, including depictions of several biochip cartridges.
Figure 31B:
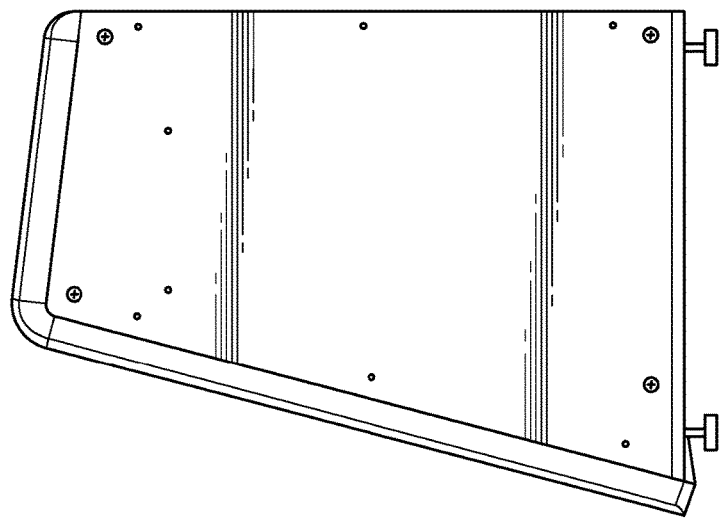
FIG. 31B is a side view of the instrument.
Figure 31A:
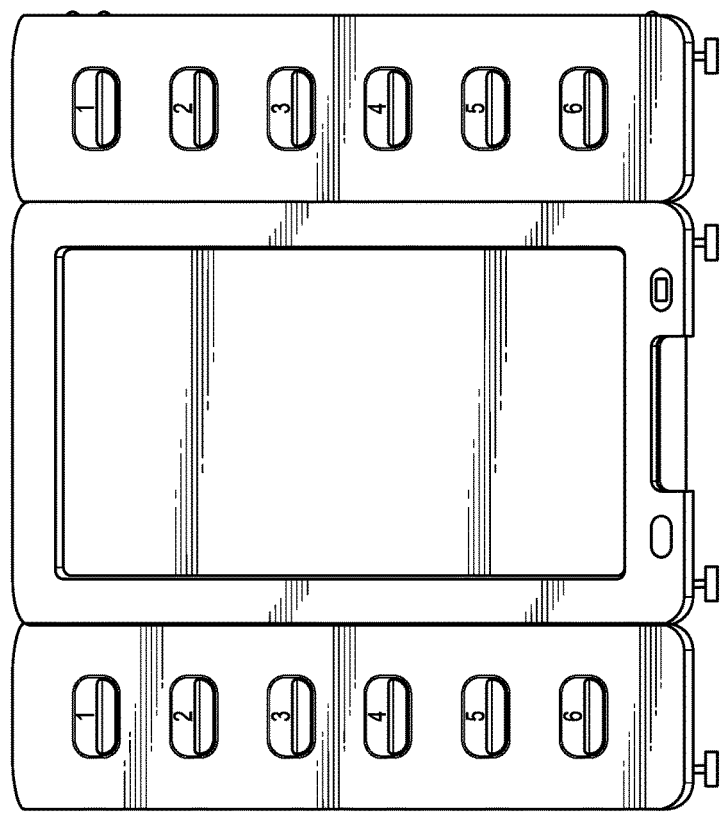
FIG. 31A is a front view of an instrument of the invention.

FIG. 26 depicts one embodiment of an instrument of the invention and several biochip cartridges. The apparatus shows the base station with a touch screen display with biochip icons with a one-to-one spatial correspondence to the biochip cartridge bays (shown here in two towers, one on each side of the display). FIG. 31A shows a front view of an instrument comprising a base station with a display screen with one tower on each side of the base station, and FIG. 31B shows a side view of the instrument. As discussed herein, the apparatus can e made with one rack, or tower, of bays, two (as shown or both on one side), three (two on one side and one on the other, or three on one side), four (two on each side), etc. In addition to the biochip icons, there are optional function icons on the bottom of the screen as described herein, along with an optional display of the time and date. Each bay has an insertion slot, configured to only allow asymmetric insertion (both requiring "right side up" insertion as depicted here by the half-moon shape, e.g. the bottom of the biochip is rounded in this embodiment although other such shapes can be used) as well as a groove/protrusion system in both the chip and the bay that allows only one end of the cartridge to be inserted into the bay ("right end in"; depicted herein where the groove is in the cartridge and the protrusion is in the bay, although this can be reversed and/or other well-known techniques for asymmetrical insertion can be used). Above the insertion slot is a curved light display, configured to show the status of the bay using any combination of colors, flashing lights or the absence of light to depict the status of the individual bay (e.g. empty, ready to load, assay underway, assay complete, cartridge ready to remove, error, etc.). A USB port is depicted with an attached barcode reader (although as will be appreciated, more than one USB port can be included). A power button is shown. In addition, the bottom of the middle component shows a cover, which conceals a built-in barcode scanner if a hand held design is not preferred. In addition, several biochip cartridges are shown, with the housing with the blister actuator sites covered by a label (optionally including one or more trademarks, barcodes, identifying labels, etc.) for example or in one case with the housing on one side removed (as described herein, in some cases the housing does not completely cover the components, for example being only on the sides and the top (this finds particular utility for the heating elements of the bottom bay, to reduce the amount of layers between the heater and the PCB board).

Figure 27A:
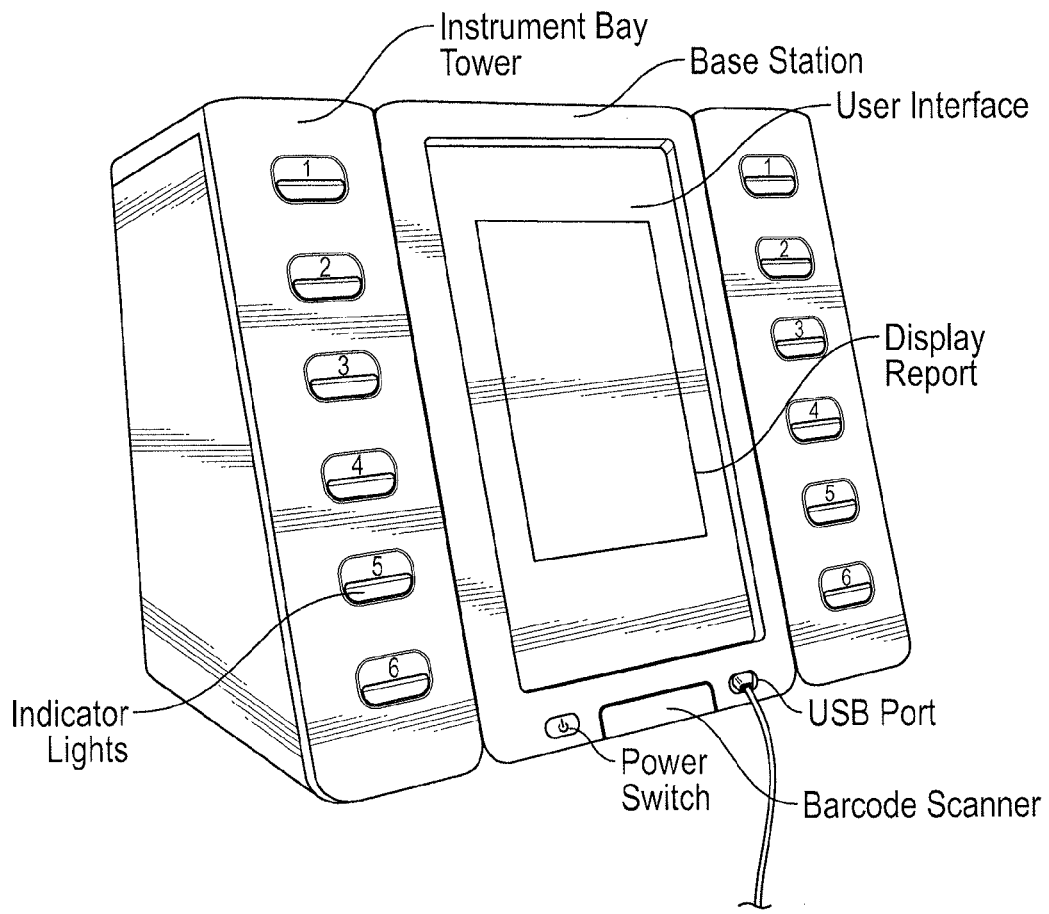
FIG. 27A is a front perspective view of an instrument of the invention including an integral barcode scanner.
Figure 27B:
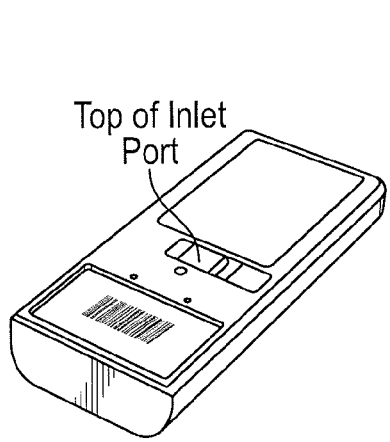
FIGS. 27B and 27C are top perspective views of two biochip embodiments with barcode labels.
Figure 27C:
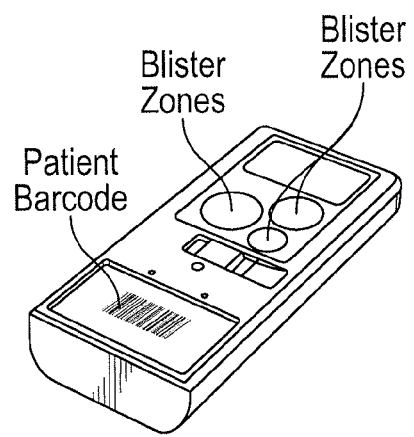

FIGS. 27A, 27B and 27C depict an additional schematic of the systems of the invention, with an integral barcode scanner and two biochips with barcode labels. FIG. 27A shows the two instrument bays and the base station with a user interface.

The devices of the invention have a number of functionalities, including the cartridge bays (optionally organized into instrument banks), a processor with an appropriate user interface, all of which are further described below.

As described herein, the invention includes cartridges that are inserted into a device containing a plurality of bays (formed from a top bay and a bottom bay) into which the cartridges fit. The devices of the invention include a least one instrument bank comprising a plurality of biochip cartridge bays for insertion and analysis of biochip cartridge(s). These instrument banks can be configured in a variety of ways, as will be appreciated by those in the art. Exemplary configurations are shown in the accompanying figures, with banks of 6 or 8 being preferred, arranged in a linear vertical fashion. As outlined herein, apparatus can include more than one instrument bank, with 1, 2, 3 or 4 banks all finding use in the present invention. In some cases, more instrument banks are used.

The Cartridge Bays

Figure 28:
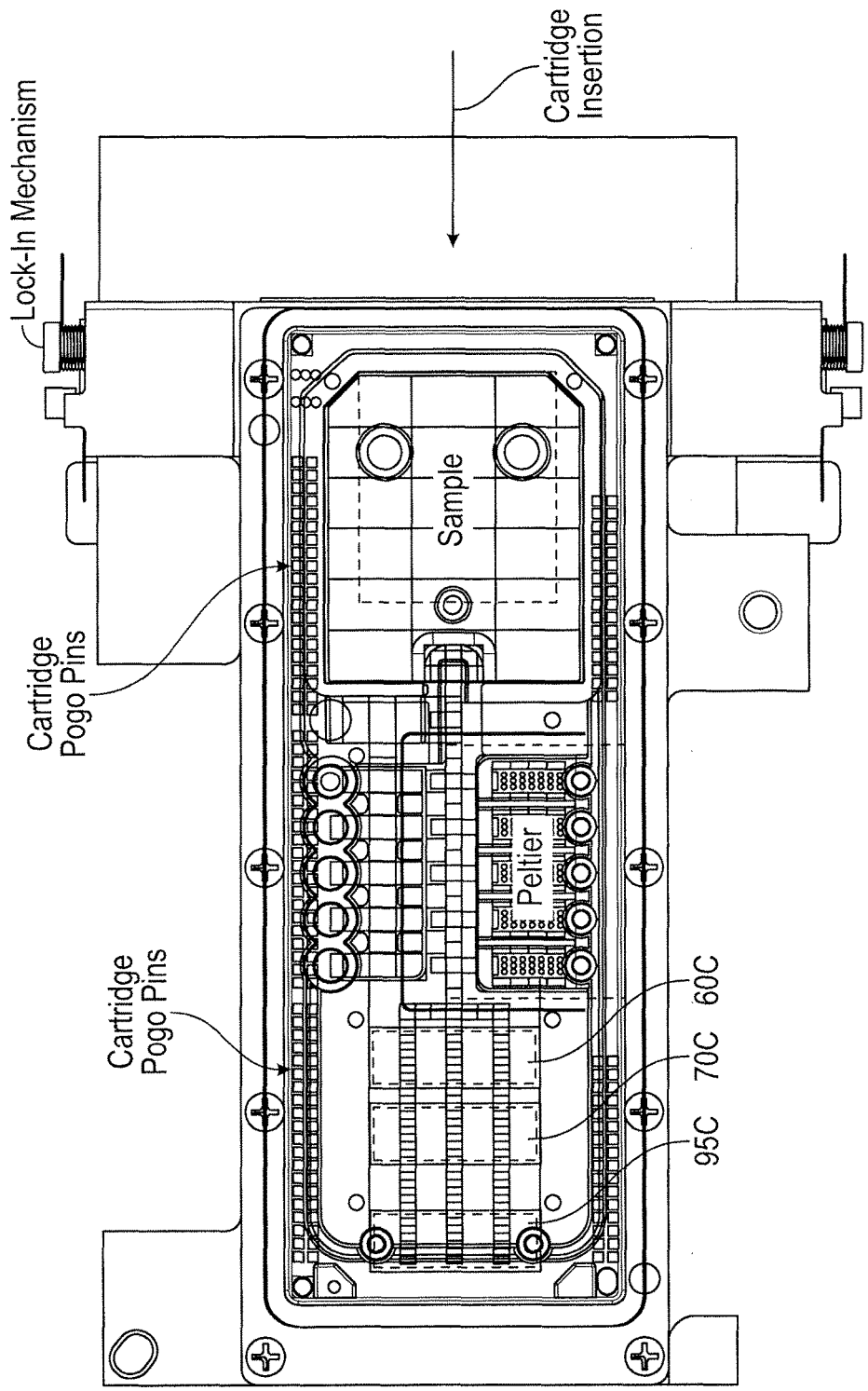
FIG. 28 is a top plan view of one embodiment showing thermal and electrical connections between a bay of the instrument and the biochip.
Figure 29:
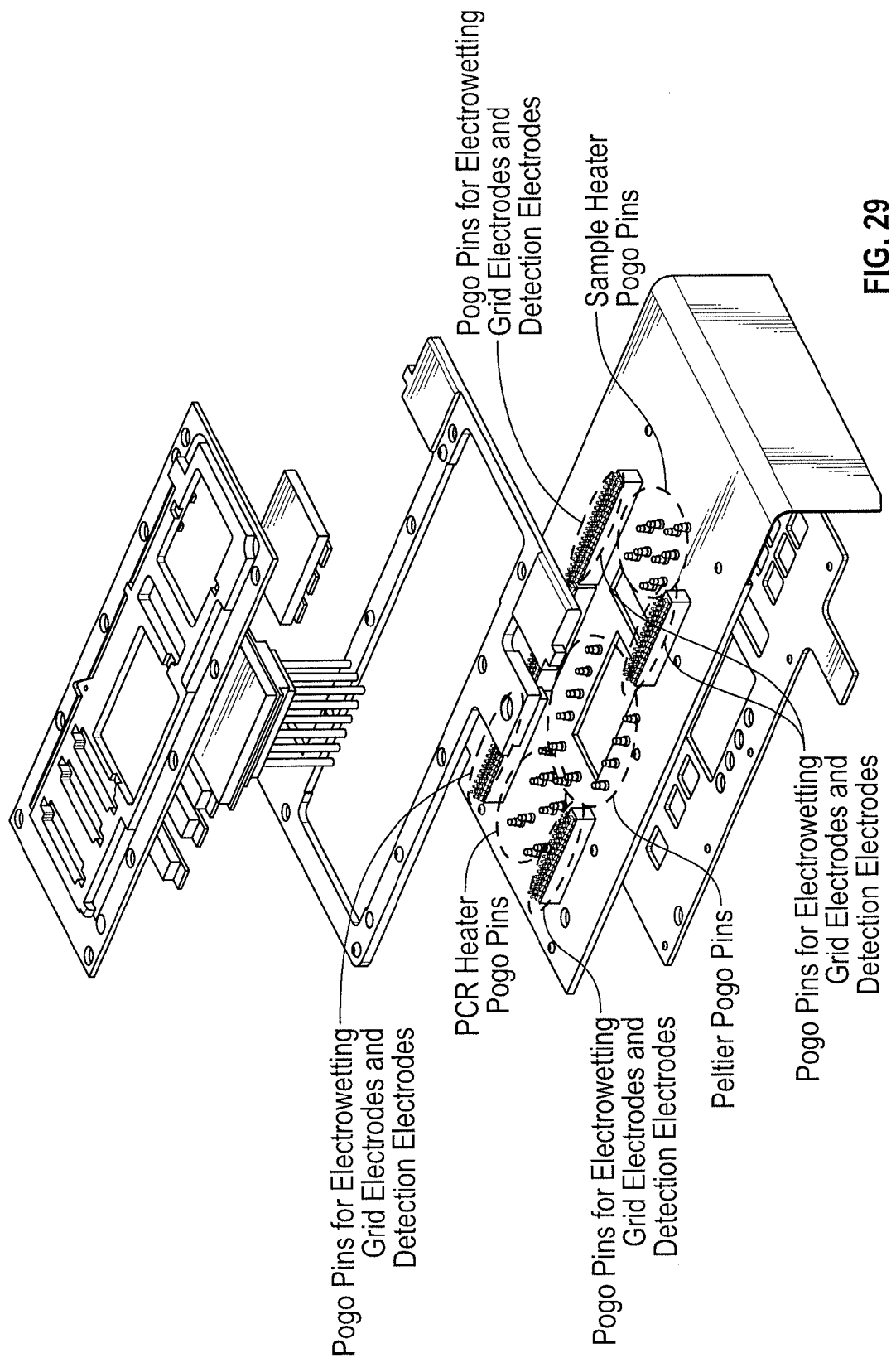
FIG. 29 is an exploded perspective view showing the electrical and thermal connections of a bottom bay of the instrument.

FIG. 28 shows one embodiment of some of the thermal and electrical connections between a bay of the apparatus and the bio chip. FIG. 29 shows an embodiment of the electrical and thermal connections of the bottom bay. There are pogo pin connectors for the PCR amplification zone heaters, pogo pin connectors for the optional heating of the sample zone, pogo pin connectors for the Peltier heater of the detection zone (again, detection is optionally and preferably done at a uniform temperature), and the edge connector pogo pins to connect the electrowetting grid electrodes and the detection electrodes. As shown in FIG. 28, the cartridge has electrode pads that connect with pogo pins in the bay (see FIG. 29). The three thermal zones (95 C, 70 C, 60 C) are shown as well as the thermal zone for uniform control of the detection zone, depicted herein as the Peltier zone; the resistive heating elements and the actual Peltier are contained in the bottom bay as shown in FIG. 29. One embodiment for a lock in mechanism for the insertion of the cartridge is also shown in FIG. 28.

The individual bays are configured to allow asymmetrical access to the biochip cartridges. That is, the cartridges can only be inserted in one direction and in one orientation (due to physical design as outlined herein, for example any or all of a housing curved only on one side (depicted in the Figures as curved on the bottom, for example, which allows the insertion only in a "top up" fashion), grooves or fittings in either or both of the cartridge and the bay such that the cartridge can only be inserted in one orientation, e.g. "front to back". A variety of such techniques are well known in the art.

Figure 32A:
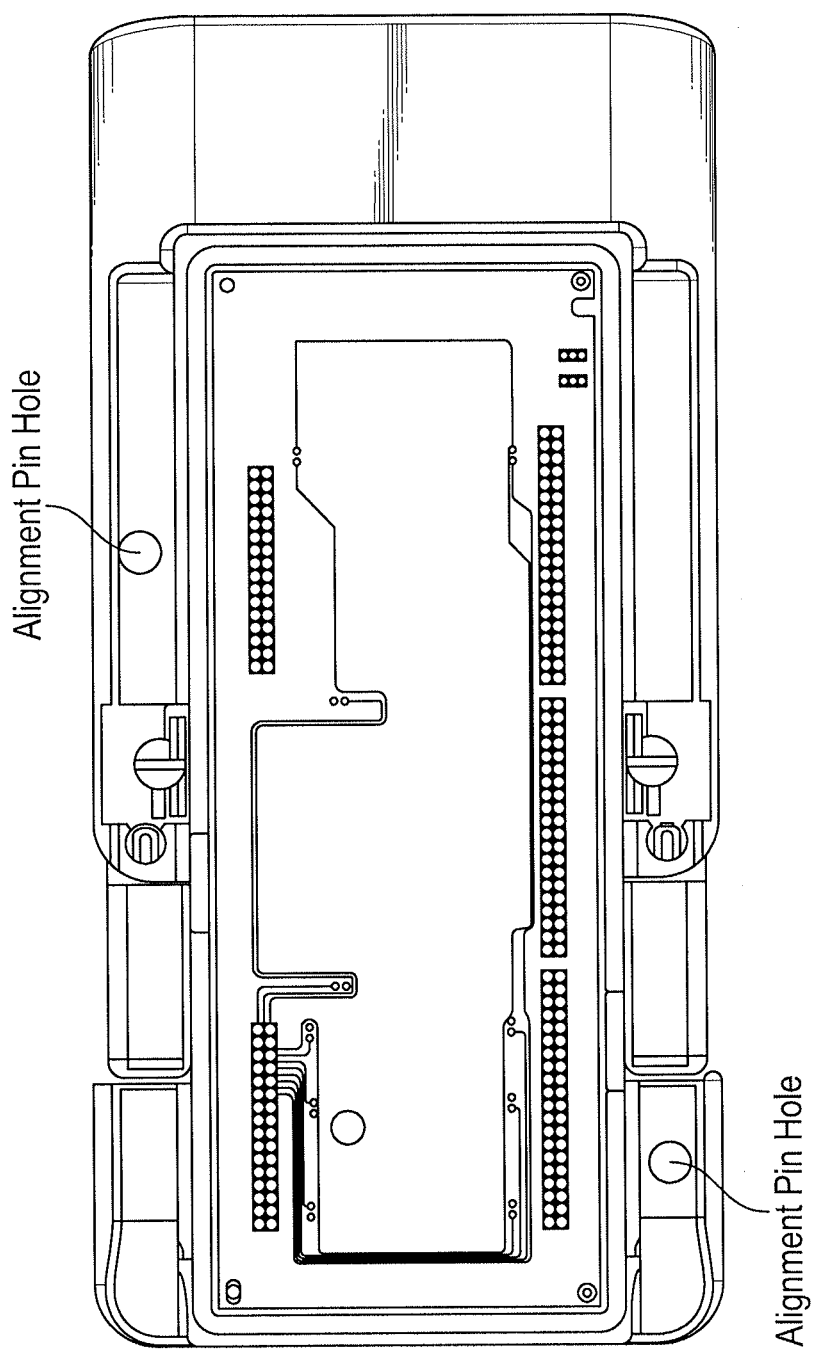
FIG. 32A is a bottom plan view of an embodiment of a biochip cartridge of the invention.
Figure 32B:
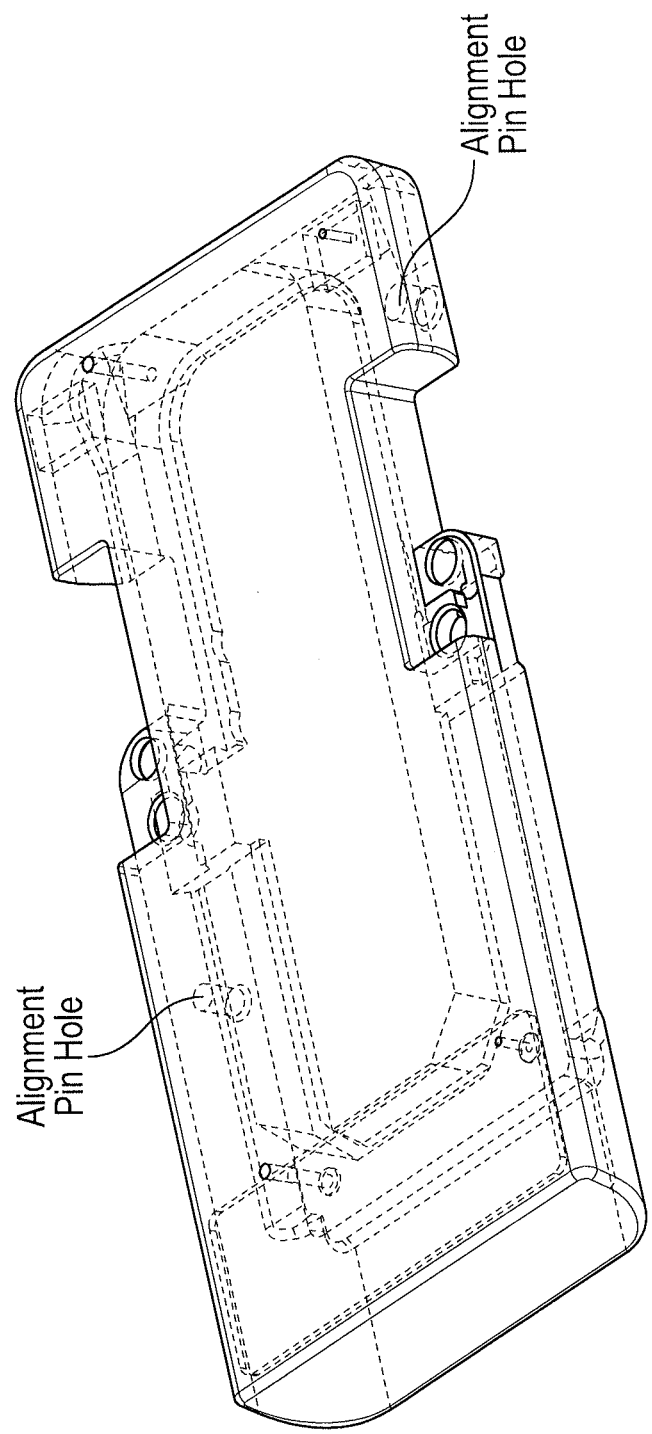
FIG. 32B is a top perspective view of an embodiment of a biochip cartridge of the invention.

FIGS. 32A and 32B depict suitable alignment mechanisms for locking the chip into the bay. FIGS. 32A and 32B show two views of an embodiment comprising alignment pin holes in a biochip cartridge to "lock in' the electrode/pogo connectors.

The bays each include a processor with memory with at least one program stored in the memory and executable by the processor comprising instructions for steps of the assay including, but not limited to, blister package actuators, heating programs, electrowetting transport steps, mixing steps, magnetic bead capture steps, washing steps, detection steps, reporting steps, exporting data steps, etc.

One important embodiment of the present invention is that each bay is individually controlled and can be used to run any assay. For example, rather than have a user load a plurality of chips and then insert them sequentially into a bay, the present system allows the user to load a cartridge, scan and insert it into the instrument, start the assay and then load the next sample.

When an optional EPROM, EEPROM or RFID tag is contained within the cartridge, for example on the bottom substrate, which encodes the identification of the assay, the bays can optionally include an EPROM, EEPROM or RFID reader, such that the instrument reads the tag and loads the appropriate assay protocol for that particular assay. In some embodiments, some or all of the executable step program is stored on the EPROM and not on the bay processor.

This may also be accomplished using a barcode reader and barcode on the cartridge itself.

The bays optionally include a lighting indicator system as well that is associated with bay status. That is, the lighting indicator system will indicate any number of optional steps, including but not limited to, whether the bay is empty, the presence or absence of a cartridge, whether the cartridge assay is underway, assay complete, and a process error. The lighting system can be different colored lights and/or flashing lights and/or absence of light or any combination thereof (e.g. "error in processing" could be red, or no light; "ready to load cartridge" could be green, "assay underway" could be flashing green, etc.).

The bays optionally include one or more "off chip" heaters for reactions such as PCR amplification reactions, isothermal amplification reactions, enzymatic reactions (e.g. the generation of enzyme substrates that are redox active), etc. These thermal elements can be positioned in a variety of ways depending on the assay requirements. Several designs are shown in the figures, including the use of pogo pins to power the thermal element(s).

The bays optionally include Peltier heaters that serve all or part of the biochip, to heat and/or cool reactions, allow isothermal reactions, or allow all the bays to keep a constant temperature no matter their location within a bank.

The bays optionally include magnetic actuators, to allow the generation of magnetic fields on all or part of the biochip as needed, for example to collect and wash magnetic beads that have adhered nucleic acid target samples. This technology includes the use of the Boom patents, including U.S. Pat. No. 5,234,809, hereby incorporated by reference in its entirety for the use of particles for the purification and/or isolation of nucleic acids.

The bays individually and optionally include components selected from the group consisting of thermal connections, spacing layers, framing layers, cartridge mechanisms, framing, fans, linear actuators, air flow systems, rotary dampers, spring loaded latches, lock-in mechanisms, etc., as depicted in the Figures. For example, cartridge mechanisms that lock a cartridge in during the assay and eject the cartridge when either an icon is pressed or an automatic ejection when the assay is done all can find use in the present invention.

The bays include electrical connections to power, monitor, and control various components, such as electrowetting and detection electrodes, heaters, thermometers, and motors, etc. Connections between the electrodes of the biochip and the corresponding electrodes in the bay can be typical "edge connector" configurations as well as pogo pin connectors; see for example FIGS. 28 and 29. In preferred embodiments, it is the bottom bay of the bays that contain the electrical connections. See FIGS. 1A, 10C and 73 of 7,172,897 and the accompanying discussion in the patent for "edge connectors" and "pogo pins" and the accompanying structure discussions for both the biochip and the bay, which document is incorporated by reference in its entirety for additional components and geometries as well as specifically including the material discussed above.

Top and Bottom Bays

"Top" and "bottom" in this sense means relative to ground. In general, as the samples and reagents are liquids, the LRM is at the top of the cartridge, and thus it is the top half of the bays that contain the mechanisms to activate the LRM.

The top bays contain the blister actuation mechanism to break open the blisters of the LRM and motivate liquid contents from them, as described above.

While one of the advantages of the present system is the lack of moving parts, in some optional embodiments valve systems are used, particularly passive "one way" valves within the LRM, such as "duck billed" one way valves. In some embodiments, active valves are utilized, and thus the bays (usually but not always the top bays) can optionally include valve actuation mechanism(s) to open and close valves as needed during the assay.

In some embodiments, for example when impeller mixing chambers are used, the bay (generally the top bay, although it could also be the bottom bay) comprises one or more mixing motor(s) to drive impeller(s) of the mixing chamber(s). The impellers can also be magnetically driven, removing the need to mechanically couple their movement. The rapidly rotating (thousands rpm) "impeller" is associated with a lysis "bead beating" chamber, (in contrast to the mixing chamber which usually employs a slowly rotating (about 100 rpm) "mixing paddle". The mixing paddle will mechanically engage a gear located proximal to the cartridge that is driven by a bay mechanism. In contrast, the impeller is a self-contained miniaturized rotor that is located inside a lysis chamber in the LRM and turned on/off by electric current creating a magnetic field. For clarity, the mixing chamber will be located upstream of the lysis chamber.

In the embodiment where magnetic capture beads are used, the bay further comprises one or more magnetic actuators to facilitate the movement or sequestration of the magnetic beads. In general, due to the proximity of the LRM, these magnetic actuator(s) are found in the top bay, although they may also be found in the bottom bays, or both. Thus, for example, the cartridge may mix the sample with lysis buffer and then deliver the lysed sample to a location comprising the magnetic capture beads (held in place either physically or by a magnetic field). The beads and the sample are mixed in the presence of binding buffer, which can utilize physical agitation by oscillating the magnetic field and/or moving the beads from one location to another and back, as needed, optionally using more than one magnetic actuator in more than one location in the top bay. Thus one or more magnetic actuators are resident in the top bay.

The bays each optionally comprise a capture and latching mechanism to control both the positioning of the cartridge (e.g. the loading of the cartridge in the correct orientation), the insertion of the cartridge into the bay sufficient to line up the LRM and the blister actuators, the electric connections, etc., as well as to prevent premature removal of the cartridge before the assay is complete and the results reported. This mechanism can be located on any part of the external housing (top, bottom, sides).

In some embodiments, as outlined herein, the bays can include sensors to monitor and control thermal zone temperatures (e.g., thermocouples, resistance temperature detectors, etc.).

The bays may comprise individual fan filters or a manifold with a single fan filter to keep dust and debris from the system, and can also include bay cooling fans in each bay compartment to help, with the aid of the individual bay heating elements to keep the bays and thus the assay at uniform temperature throughout a run.

The bays generally comprise a bay PCB to power, monitor, and control the bay, LRM, and the cartridge in general.

The Base Station

The base station of the instrument comprises a number of components, including a central processing unit that allows independent bay controllers and electric and network connections to each tower, an optional identification tag reading device as described herein, (e.g., a hand-held bar code scanner) and a touch screen user interface with individual icons corresponding to each bay.

The systems of the invention include at least one processor, and in many cases, as described herein, each bay of a bank has its own individual processor. The devices also include memory and at least one program stored in the memory and executable by the processor, comprising instructions to execute the assays (including the manipulation of droplets, reagents, blister ruptures, and detection programs) of the invention.

In some embodiments, each bay is independently controlled and processed. That is, after scanning a patient or sample barcode, the operator can choose to put the cartridge into any bay, in no particular order, and start the assay, independently of any other cartridge/bay combination and/or status. That is, the bays allow optional random and optional continuous access, such that a bank need not be run at the same time, and cartridges can be inserted into a bay at any time after they are loaded with sample.

The bays each include a processor with memory with at least one program stored in the memory and executable by the processor comprising instructions for steps of the assay including, but not limited to, blister package actuators, heating programs, electrowetting transport steps, mixing steps, magnetic bead capture steps, washing steps, detection steps, reporting steps, exporting data steps, etc.

In some embodiments, the bays optionally include EPROM readers to allow reading the EPROMs on the individual cartridges as discussed below, such that some or all of the executable step program is stored on the EPROM and not on the bay processor.

In addition to the processors for bay control, in general the devices have a processor, memory and executable programs to allow the creation and maintenance of operator profiles, such as log-in information, preferences, etc. In addition, one program that is optionally included allows the association of the assay reports to be tied to the operator who loaded the sample, and not the operator who unloads the cartridge. That is, one operator does not need to log off for a second one to log into any particular device.

The base station can also include technology to allow remote access, remote control, and remote servicing, such as that sold and distributed by Axeda technology (available at the Axeda website).

In a preferred embodiment, the base station comprises an identification tag reading component to allow identification and correlation of the patient sample to a result. In some embodiments, this identification tag reader is a barcode reader to read a corresponding barcode on the cartridge. The barcode reader can be a hand held scanner, which can be attached to the base station by use of a processor port, such as a USB port. Alternatively, the base station itself can be configured to contain a barcode reader, for example at the bottom of the base station, where the user can slide the cartridge under the station for reading. As outlined herein, these barcodes may be used for a wide variety of purposes, including, but not limited to, identifying the sample (e.g. patient number or code), the test being done, the batch number of the chip, calibration information, assay protocols including cycle time, signal processing requirements, etc.

In addition, in some embodiments the barcodes can be used to control the instrument. For example, instrument control may be through the use of a keyboard, a mouse or a barcode reader. Thus, for example, there may be barcodes on the cartridges to indicate the identity of the chip, but also on a card to scan for starting the assay, stopping the assay, downloading the data, etc. Thus for example a user would scan the cartridge prior to insertion into a bay, and then scan a barcode to start the assay protocol. In a preferred embodiment, the card of barcode commands are found in a drawer or storage compartment of the device, outlined herein.

In general, the base station includes a common electric and network hub to simplify cabling and tower connection to the base station.

User Interface

The devices of the invention further have at least one touch screen display having a plurality of bay icons, each icon uniquely corresponding to one of said plurality of bays. As shown in the figures, the bay icons share a one to one correspondence, including a spatial correspondence, with the biochip cartridge bays where the cartridges are inserted. That is, the upper left hand bay icon corresponds to the upper left hand bay, etc. Thus, depending on whether 1, 2, 3 or 4 banks of 6 bays are used, the touch screen display will have 6, 12, 18 or 24 bay icons, arranged by column and row in the same fashion as the bays.

The system optionally uses a launch pad interface that is icon-centric in order to support globalization, e.g. to avoid translation of general operating parameters into multiple languages.

In one embodiment, the insertion of a biochip cartridge into one of the bays causes the corresponding bay icon to be enlarged and/or exhibited, generally causing a panel of options to be exhibited. In general, the panel of options is a plurality of secondary icons that allow different data about the bay and the inserted chip to be shown. Thus, for example, the secondary icons include, but are not limited to, an icon to review biochip cartridge data or report, an icon for status of a biochip cartridge assay, an icon depicting the time remaining in a biochip cartridge assay (for example, as a clock face that when pressed shows a time bar that changes fill color as a result of assay progress); an icon to generate a data report of biochip cartridge data; an icon to print a data report of biochip cartridge data (e.g. a schematic of a printer); an icon to email a data report of biochip cartridge data (e.g. an envelope icon); an icon to export a data report of biochip cartridge data to another computer device; and an icon to display a virtual keyboard. Again, these secondary icons are generally selected to be "language neutral", such that they are easily comprehended by operators that speak different languages.

Alternatively, the panel of options is displayed by selecting and touching one of the bay icons without the need to load a cartridge.

Once an assay is complete, the bay icon can be pressed to result in the display of an assay report, detailing the results of the assay (which virus present, SNP status, etc.). This report can be printed by icon, emailed by icon, downloaded to an external memory device (e.g. flash memory device), etc.

IV. Assays

General Methods

The detection methods are based on capture binding ligands (capture probes when the target is nucleic acid) to bind the target analytes and solution binding ligands (label probes when the target is nucleic acid) that carry electron transfer moiety (ETM) electrochemical labels to form "sandwich hybridization complexes". See for example FIG. 2B of U.S. Pat. No. 7,935,481, incorporated by reference (as are all of the Figures, accompanying legends and the associated specification descriptions). That is, only in the presence of the target analyte will the ETM(s) be present at the surface of the detection electrode, thus giving rise to a signal. Suitable ETMs are outlined in the cited cases, and all discussions relating to ETMs are specifically incorporated independently and optionally by reference.

These techniques are generally described in U.S. Pat. Nos. 4,887,455; 5,591,578; 5,705,348; 5,770,365; 5,807,701; 5,824,473; 5,882,497; 6,013,170; 6,013,459; 6,033,601; 6,063,573; 6,090,933; 6,096,273; 6,180,064; 6,190,858; 6,192,351; 6,221,583; 6,232,062; 6,236,951; 6,248,229; 6,264,825; 6,265,155; 6,290,839; 6,361,958; 6,376,232; 6,431,016; 6,432,723; 6,479,240; 6,495,323; 6,518,024; 6,541,617; 6,596,483; 6,600,026; 6,602,400; 6,627,412; 6,642,046; 6,655,010; 6,686,150; 6,740,518; 6,753,143; 6,761,816; 6,824,669; 6,833,267; 6,875,619; 6,942,771; 6,951,759; 6,960,467; 6,977,151; 7,014,992; 7,018,523; 7,045,285; 7,056,669; 7,087,148; 7,090,804; 7,125,668; 7,160,678; 7,172,897; 7,267,939; 7,312,087; 7,381,525; 7,381,533; 7,384,749; 7,393,645; 7,514,228; 7,534,331; 7,560,237; 7,566,534; 7,579,145; 7,582,419; 7,595,153; 7,601,507; 7,655,129; 7,713,711; 7,759,073; 7,820,391; 7,863,035; 7,935,481; 8,012,743; 8,114,661, all of which are incorporated by reference in their entirety.

As outlined herein, the systems of the invention are used to detect the presence or absence of a target (e.g. viruses or bacteria) and/or the elucidation of a specific sequence such as a single nucleotide polymorphism (SNP). As is known in the art, there are a number of techniques that can be used to detect or determine the identity of a base at a particular location in a target nucleic acid, including, but not limited to, the use of temperature, competitive hybridization of perfect and imperfect probes to the target sequence, sequencing by synthesis, for example using single base extension techniques (sometimes referred to as "mini-sequencing"), the oligonucleotide ligase amplification (OLA) reaction, rolling circle amplification (RCA), allelic PCR, competitive hybridization and Invader™ technologies. In addition, the present invention is directed to a novel invention that capitalizes on novel properties of surface-bound arrays, and uses "competimers" to reduce non-specific binding.

These techniques in the present invention rely on the formation of assay complexes on a detection electrode surface, as a result of hybridization of a target sequence (either the target sequence of the sample or an amplicon sequence generated in the assay) to a capture probe on the surface. As is more fully outlined herein, this may be direct or indirect (e.g. through the use of sandwich type systems) hybridization. The assay complex further comprises at least one electron transfer moiety (ETM) that is also either directly or indirectly attached to the target. Once the assay complexes are formed, the presence or absence of the ETMs are detected as is described below and in U.S. Pat. Nos. 5,591,578; 5,824,473; 5,770,369; 5,705,348 and 5,780,234; U.S. Ser. No. 08/911,589 (U.S. Pat. No. 6,232,062); Ser. No. 09/135,183; 09/306,653 (U.S. Pat. No. 6,600,026); Ser. No. 09/134,058 (U.S. Pat. No. 6,290,839); Ser. No. 09/295,691 (U.S. Pat. No. 6,942,771); Ser. No. 09/238,351 (U.S. Pat. No. 7,090,804); Ser. No. 09/245,105 (U.S. Patent Application Publication No. 2003-0087228) and Ser. No. 09/338,726 (U.S. Pat. No. 6,264,825); and PCT Pub Nos. WO 98/20162; WO 00/16089; and PCT Application Nos. PCT/US99/01705 (WO 99/037819); PCT/US99/01703 (WO 99/57319); PCT/US00/10903 (WO 00/62931) and PCT/US99/10104 (WO 99/57317), all of which are expressly incorporated herein by reference in their entirety. Specific reference is made to the structures of the ETMs, the different assay methods and assay components, the methods of making the PCB component/detection electrodes, etc.

Specific SNP detection generally requires one or two primer nucleic acids (which may include the ETM labels as well as the use of nucleic acid analogs) that is hybridized to the target sequence to form a hybridization complex, and an enzyme is added that in some way modifies the primer to form a modified primer; generally, the occurrence of the modification depends on the presence or absence of a particular sequence, thus allowing sequence differentiation. For example, OLA requires two primers that hybridize (either directly adjacently or separated by one or more bases) to the target sequence and a ligase; Invader® requires two primers and a cleavage enzyme; etc. Thus, in general, a target nucleic acid is added to a reaction mixture that comprises the necessary amplification components, and a modified primer is formed, which is then either detected as an indication that the variation is present, or queried to determine the identity of the base at the position of interest.

In general, the modified primer (which can be an amplicon in the case of traditional PCR as is generally outlined herein) is incorporated into an assay complex that comprises a label, such as an electron transfer moiety (ETM), which is either incorporated by an enzyme, present on the original primer, or added via a label probe. As required, the unreacted primers can be removed in a variety of ways, as will be appreciated by those in the art, although in many embodiments this is not required. The hybridization complex is then optionally disassociated, and the modified primer is added to an electrode as is generally described herein and in the cited applications. Usually, the electrodes comprise capture probes that will hybridize to the modified primers although as outlined herein, a variety of configurations, including sandwich assays, can be used. Detection proceeds via detection of the ETM label as an indication of the presence, absence or amount of the target sequence.

The methods of the invention find particular use in genotyping assays, i.e. the detection of particular nucleotides at specific positions, although as will be appreciated by those in the art, amplification and/or quantification need not necessarily occur to do genotyping. In these embodiments, the assay generally relies on the use of two (or more, in the cases of three base alleles or four base alleles) label probes, each of which has ETMs with different redox potentials (E0) that can be distinguished in the assay. In this way homogeneous and heterogeneous alleles can be distinguished (the former being either all first label or all second label, and the latter showing two peaks at each label potential).

Thus the present invention provides "assay complexes" (referred to herein and in the cited patents as "hybridization complexes" when the targets are nucleic acids) that are formed as "sandwich assay complexes", as depicted in the Figures of many of the cited patents. See for example FIG. 2B of U.S. Pat. No. 7,935,481, incorporated by reference (as are all of the Figures, accompanying legends and the associated specification descriptions). That is, only in the presence of the target analyte will the ETM(s) be present at the surface of the detection electrode, thus giving rise to a signal. Suitable ETMs are outlined in the cited cases (particularly useful in some embodiments are metallocenes, with ferrocene and ferrocene derivatives as defined in the incorporated patents), and all discussions relating to ETMs are specifically incorporated independently and optionally by reference.

The detection electrodes comprise capture binding ligands, preferably covalently attached. By "binding ligand" or "binding species" herein is meant a compound that is used to probe for the presence of the target analyte, which will bind to the target analyte. In general, for most of the embodiments described herein, there are at least two binding ligands used per target analyte molecule; a "capture" or "anchor" binding ligand (also referred to herein as a "capture probe", particularly in reference to a nucleic acid binding ligand) that is attached to the detection electrode as described herein, and a soluble binding ligand (frequently referred to herein as a "signaling probe" or a "label probe" when the target is nucleic acid), that binds independently to the target analyte, and either directly or indirectly comprises at least one ETM.

Generally, the capture binding ligand allows the attachment of a target analyte to the detection electrode, for the purposes of detection. As is outlined in the cited patent list, attachment of the target analyte to the capture binding ligand may be direct (i.e. the target analyte binds to the capture binding ligand) or indirect (one or more capture extender ligands may be used).

In a preferred embodiment, the binding is specific, and the binding ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding that is not highly specific; for example, the systems may use different binding ligands, for example an array of different ligands, and detection of any particular analyte is via its "signature" of binding to a panel of binding ligands, similar to the manner in which "electronic noses" work. The binding should be sufficient to allow the analyte to remain bound under the conditions of the assay, including wash steps to remove non-specific binding. In some embodiments, for example in the detection of certain biomolecules, the binding constants of the analyte to the binding ligand will be at least about $10^{-4}$ to $10^{-6}$ $M^{-1}$, with at least about $10^{-5}$ to $10^{-9}$ $M^{-1}$ being preferred and at least about $10^{-7}$ to $10^{-9}$ $M^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand is generally a substantially complementary nucleic acid. Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins (particularly including antibodies or fragments thereof (FAbs, etc.)), small molecules, or aptamers, described above. Preferred binding ligand proteins include peptides. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences.

In this embodiment, when the binding ligand is a nucleic acid, preferred compositions and techniques are outlined in U.S. Pat. Nos. 5,591,578; 5,824,473; 5,705,348; 5,780,234 and 5,770,369; U.S. Ser. Nos. 08/873,598 08/911,589; PCT Pub. Nos. WO 98/20162; WO 98/12430; WO 98/57158; WO 00/16089) WO 99/57317; WO 99/67425; WO 00/24941; WO 00/38836; WO 99/37819; and WO 99/57319; PCT Application Nos. PCT/US00/10903 (WO 00/62931) and PCT/US00/20476; and related materials, all of which are expressly incorporated by reference in their entirety.

The method of attachment of the capture binding ligands to the attachment linker (either an insulator or conductive oligomer) will generally be done as is known in the art, and will depend on both the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups and thiol groups. These functional groups can then be attached, either directly or indirectly through the use of a linker as described in the list above.

In this way, capture binding ligands comprising proteins, lectins, nucleic acids, small organic molecules, carbohydrates, etc. can be added.

A preferred embodiment utilizes proteinaceous capture binding ligands. As is known in the art, any number of techniques may be used to attach a proteinaceous capture binding ligand to an attachment linker. A wide variety of techniques are known to add moieties to proteins.

In some embodiments, each detection electrode comprises a single type of capture probe. In others, a plurality of different capture probes (e.g. 2, 3 or 4, generally) can be used (with corresponding label probes with different redox potentials).

A preferred embodiment utilizes nucleic acids as the capture binding ligand. While most of the following discussion herein focuses on nucleic acids, as will be appreciated by those in the art, many of the techniques outlined below apply in a similar manner to non-nucleic acid systems as well, and to systems that rely on attachment to surfaces other than metal electrodes.

As outlined therein, the detection electrodes generally further include self-assembled monolayers (SAMs) as well. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. A majority of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer.

The present invention provides methods of detecting the presence or absence of target analytes in samples used generally for diagnosis of exogenous pathogens, nucleic acid based diseases and/or drug suitability, dosages, etc.

The general methods rely on loading the sample into the cartridge, closing the sample inlet port, and inserting the cartridge into the instrument (optionally adding a patient identifier barcode to the cartridge and scanning it in with a barcode reader). The instrument, comprising a CPU, then executes a number of operational steps to initiate and complete the appropriate assay and generate a patient report. FIGS. 33A, 33B, 33C, and 33D show an exemplary process run with the operational steps, also identifying the "actor" that accomplishes the steps. As will be appreciated by those in the art, there are a wide variety of assays that can be run on the systems of the invention.

The invention claimed is:

1. A biochip cartridge for detecting a target analyte, the biochip cartridge comprising:
   A) a bottom substrate
   B) a top plate;
   C) a liquid reagent module comprising a plurality of blisters; and
   D) an external housing having open areas over at least one of the plurality of blisters.

2. A biochip cartridge according to claim 1, wherein said top plate comprises a conductive surface.

3. A biochip cartridge according to claim 1, wherein said top plate comprises at least one fluid hole spatially corresponding to said bottom substrate.

4. A biochip cartridge according to claim 1, wherein said bottom substrate comprises a dried assay reagent.

5. A biochip cartridge according to claim 1, wherein said liquid reagent module further comprises an aliquot of magnetic capture beads.

6. A biochip cartridge according to claim 3, wherein at least one of said fluid holes is configured to dispense a fluid assay reagent at a location remote from a blister comprising said reagent.

7. A biochip cartridge according to claim 1, wherein said external housing is asymmetrically shaped.

8. A biochip cartridge according to claim 4, wherein said dried assay reagent is selected from the group consisting of:

dNTPs, PCR primers, a nucleic acid polymerase, an exonuclease, labelled signaling probes, and a combination thereof.

9. A biochip cartridge according to claim 1, wherein said external housing further comprises a cartridge identification tag.

10. A biochip cartridge according to claim 1, wherein the plurality of blisters comprise fluid assay reagents selected from the group consisting of: water, an immiscible fluid, a lysis buffer, a binding buffer, an elution buffer, and a reconstitution buffer.

11. A biochip cartridge according to claim 1, wherein all or part of the top plate is coated with a hydrophilic, oleophobic material.

12. A biochip cartridge according to claim 1, wherein said top plate comprises one or more entry ports configured to allow fluid flow into said reaction chamber.

13. A biochip cartridge according to claim 1, wherein said top plate further comprises one or more vents configured to reduce air bubble formation within the reaction chamber and/or remove any air bubbles that do form within the reaction chamber.

14. A biochip cartridge for detecting a target analyte, the biochip cartridge comprising:
    a) a liquid reagent module comprising a blister connected to a sphere blister by a channel;
    b) a top plate; and
    c) a bottom substrate comprising a printed circuit board.

15. A biochip cartridge according to claim 14, wherein the sphere blister comprises a steel ball bearing.

16. A biochip cartridge according to claim 14, wherein the sphere blister comprises a septum.

17. A biochip cartridge according to claim 14, wherein the blister is connected to the sphere blister by the channel blocked by a breakable seal.

18. A biochip cartridge according to claim 14, wherein the liquid reagent module further comprises magnetic capture beads.

19. A biochip cartridge according to claim 14, wherein the liquid reagent module further comprises a waste chamber.

20. A biochip cartridge according to claim 14, wherein the liquid reagent module further comprises a porous filter.

* * * * *